(12) United States Patent
Cohen et al.

(10) Patent No.: US 7,560,116 B2
(45) Date of Patent: Jul. 14, 2009

(54) COMPOSITIONS, METHODS AND KITS RELATING TO POXVIRUS SUBUNIT VACCINES

(75) Inventors: Gary H. Cohen, Havertown, PA (US); Roselyn J. Eisenberg, Haddonfield, NJ (US); John Charles Whitbeck, Glenside, PA (US); Lydia Aldaz-Carroll, Philadelphia, PA (US); Bernard Moss, Bethesda, MD (US); Shlomo Lustig, Ramat Gan (IL); Christiana Fogg, Germantown, MD (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 156 days.

(21) Appl. No.: 11/010,979

(22) Filed: Dec. 13, 2004

(65) Prior Publication Data

US 2006/0062800 A1  Mar. 23, 2006

Related U.S. Application Data

(63) Continuation of application No. 10/788,835, filed on Feb. 27, 2004, now abandoned.

(60) Provisional application No. 60/451,337, filed on Feb. 28, 2003.

(51) Int. Cl.
*A61K 39/38* (2006.01)
*A61K 39/12* (2006.01)
*A61K 39/295* (2006.01)
*A61K 39/285* (2006.01)
*C07K 17/00* (2006.01)
*A61K 39/187* (2006.01)

(52) U.S. Cl. .............. 424/202.1; 424/186.1; 424/232.1; 424/184.1; 530/350

(58) Field of Classification Search ..................... None
See application file for complete search history.

(56) References Cited

U.S. PATENT DOCUMENTS

| | | | |
|---|---|---|---|
| 6,451,309 B2 | 9/2002 | Hooper et al. | |
| 6,562,376 B2 | 5/2003 | Hooper et al. | 424/489 |
| 6,620,412 B2 | 9/2003 | Hooper et al. | 424/147.1 |
| 2006/0003316 A1* | 1/2006 | Simard et al. | 435/5 |

OTHER PUBLICATIONS

Ravanello et al., Conditional Lethal Expression of the Vaccinia Virus L1R Myristylated Protein Reveals a Role in Virion Assembly, 1994, vol. 68, No. 10, pp. 6401-6410.*
Martin et al., Identification and Analysis of Three Myristylated Vaccinia Virus Late Proteins, 1997, Journal of Virology, vol. 71, No. 7, pp. 5218-5226.*
Betakova et al., 1999, Virology 261: 347-356.
Colamonici et al., 1995, . Biol. Chem. 270: 15974-15978.
Franke et al., 1989, J. Virol. 63: 4479-4488.
Franke et al., 1990, J. Virol. 64: 5988-96.
Galmiche et al., 1999, Virology 254: 71-80.
Geraghty et al., 1998, Science 280: 1618-1620.
Hsiao et al., 1999, J. Virol. 73: 8750-8761.
Hutchinson et al., 1992, J. Virol. 66: 2240-2250.
Ichihashi et al., 1994, Virology 202: 834-843.
Ichihashi et al., 1996, Virology 217: 478-485.
Ichihashi et al., 1996, Virology 220: 491-494.
Hooper et al., 2000, Virology 266: 329-339.
Krummenacher et al., 1999, J. Virol. 73: 8127-8137.
Lin et al., 2000, J. Virol. 74: 3353-3365.
Lin et al., 2002, J. Biol. Chem. 277: 20949-20959.
Massung et al., 1994, Virology 201: 215-240.
Ramirez et al., 2002, J. Gen. Virol. 83: 1059-1067.
Ravanello et al., 1993, J. Biol. Chem. 268: 7585-93.
Ravanello et al., 1994, J. Gen. Virol. 75: 1479-83.
Rodriguez et al., 1987, J. Virol. 61: 395-404.
Rodriguez et al., 1993, J. Virol. 67: 3435-3440.
Rodriguez et al., 1995, J. Virol. 69: 4640-4648.
Sahu et al., 1996, J. Immunol. 157: 884-891.
Senkevich et al., 2000, Proc. Natl. Acad. Sci. U.S.A. 97: 12068-12073.
Sisk et al., 1994, J. Virol. 68: 766-775.
Vazquez et al., 1998, J. Virol. Methods. 72: 10126-10137.
Wallengren et al., 2001, Virology 290: 143-152.
White et al., 2002, J. Virol. 76: 467-472.
Wolfe et al., 1995, Virology 211: 53-63.
Liang et al., "Expression of a Biologically Active Antiviral Antibody Using a Sindbis Virus Vector System," *Molecular Immunology* 34:907-917 (1997).
Sanna et al., "Directed Selection of Recombinant Human Monoclonal Antibodies to Herper Simplex Virus Gylcoproteins from Phage Display Libraries," *Proc. Natl. Acad. Sci. USA* 92:6439-6443 (1995).
Law et al., 2001 Virology 280:132-142.
Mathew et al., 2001 J. of Gen. Virology 82:1199-1213.
Lorenzo et al., 1998 Virology 252:450-457.
Herrera et al., 1998 J. of Virology 78:10230-10237.
Fogg et al., 2004 J. of Virology 78:10230-10237.
Aldaz-Carroll et al., 2005 J. of Virology 79:6260-6271.
Chen et al., 2006 PNAS 103:1882-1887.

* cited by examiner

*Primary Examiner*—Bruce Campell
*Assistant Examiner*—Benjamin P Blumel
(74) *Attorney, Agent, or Firm*—Drinker Biddle & Reath, LLP

(57) ABSTRACT

The invention is directed to a poxvirus vaccine comprising a soluble truncated poxvirus envelope protein. The invention is also directed to a vaccine comprising a nucleic acid encoding such proteins. Also included is an antibody which specifically binds to the proteins and nucleic acid encoding the same, as well as methods of preventing and treating a poxvirus infection using the afore-mentioned vaccine, antibody, protein, and nucleic acid encoding them.

18 Claims, 43 Drawing Sheets

FIGURE 1

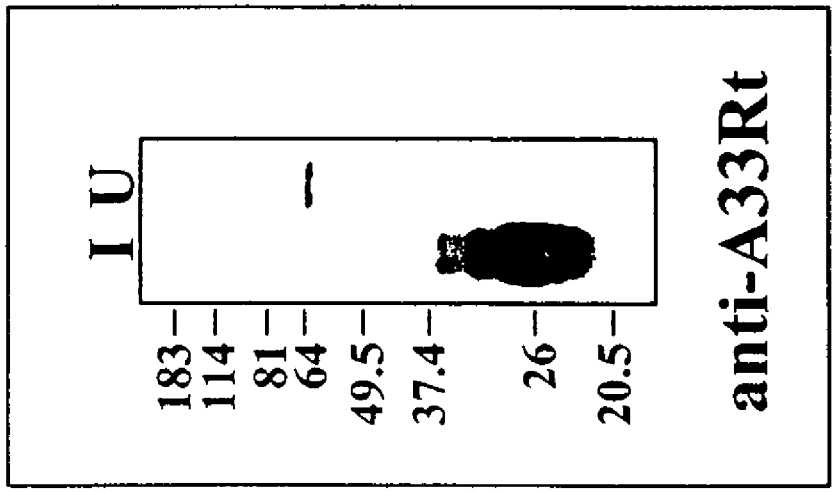
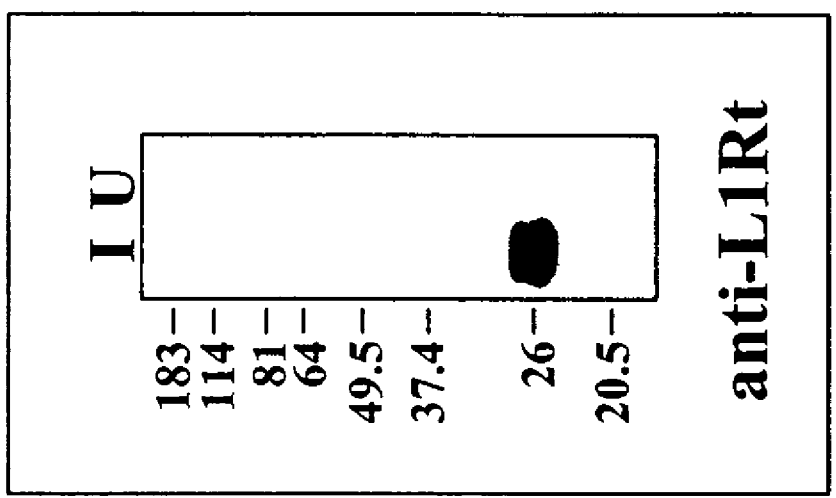
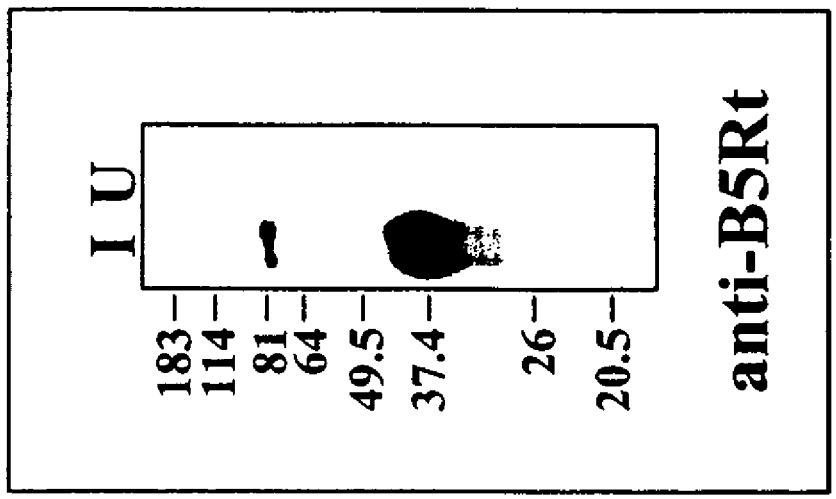

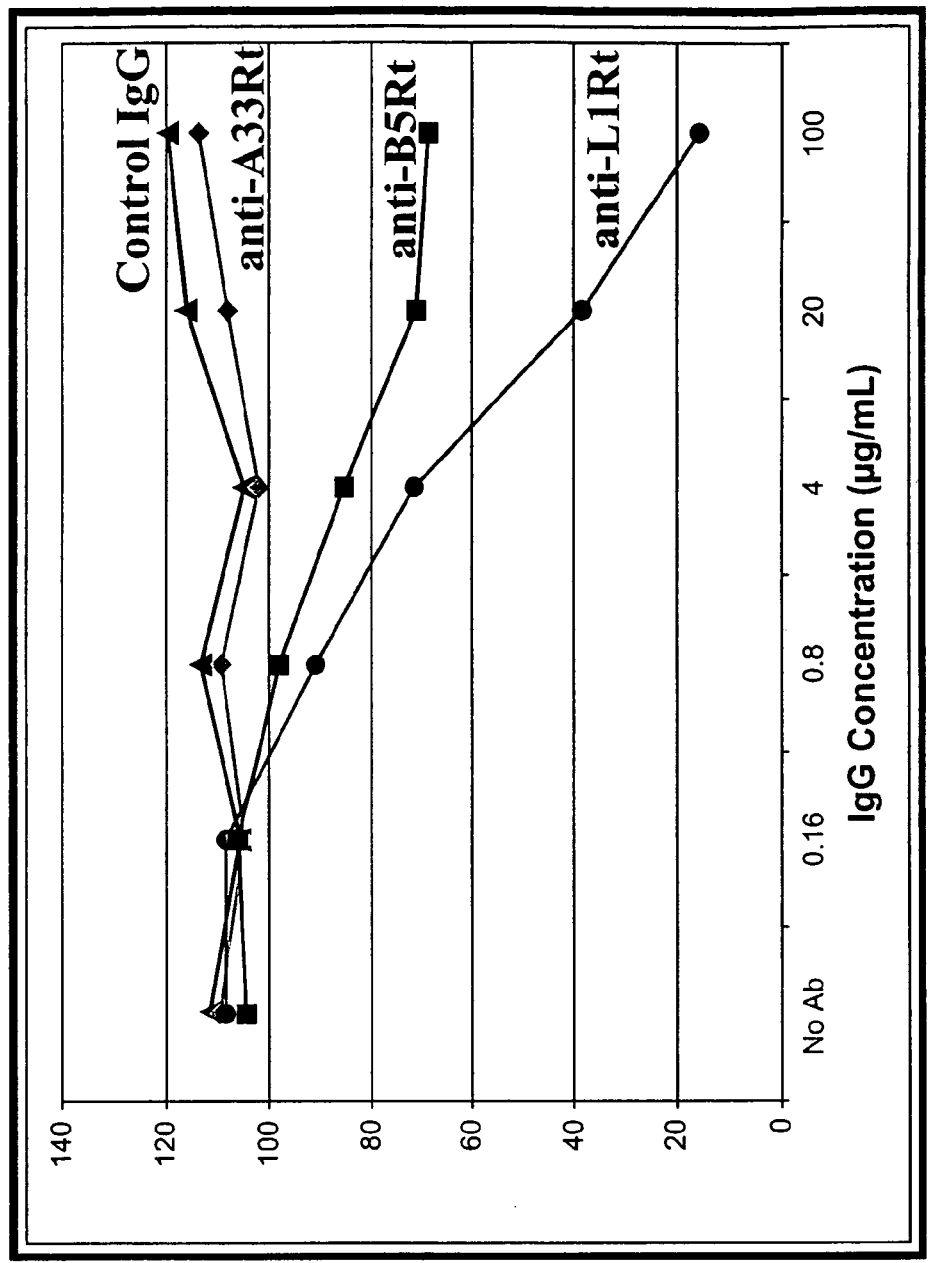
FIGURE 9B
FIGURE 9A
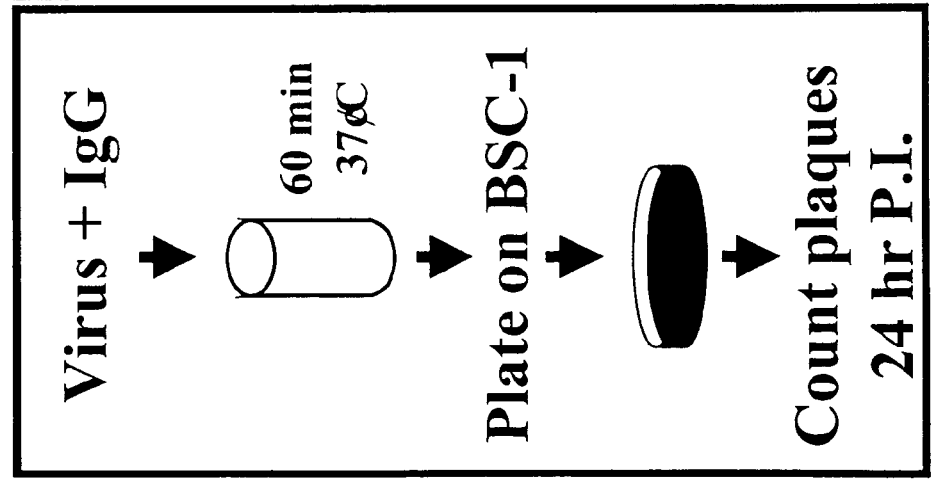

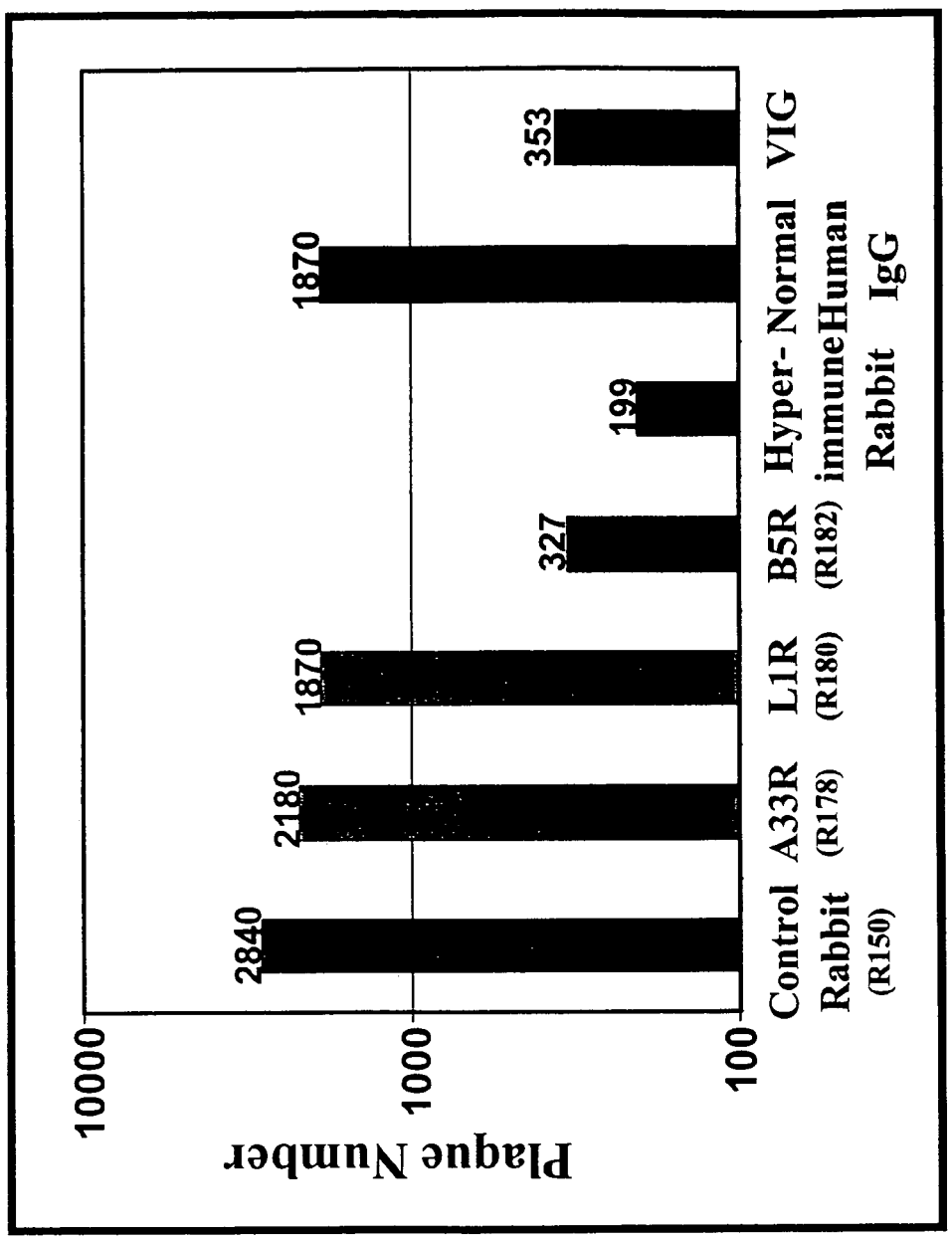
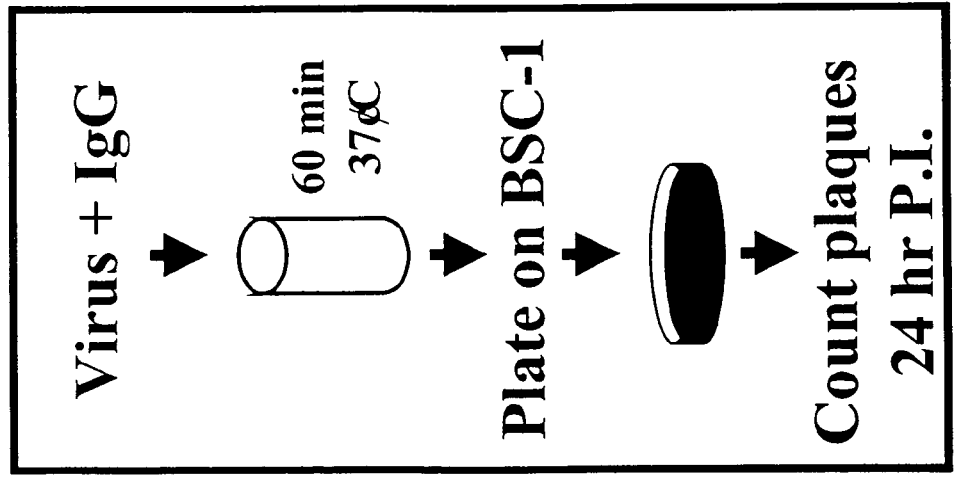
FIGURE 10B
FIGURE 10A

| | Plaque reduction | Comet tail inhibition |
|---|---|---|
| VMC-20 | + | - |
| VMC-21 | + | - |
| VMC-22 | + | - |
| VMC-25 | ++ | + |
| VMC-26 | ++ | - |
| VMC-29 | + | ++ |
| VMC-33 | + | NT |

| SEQ ID. NO | Name | Sequence (SGSG-) | Range aa |
|---|---|---|---|
| 7 | B5R pep#1 | TCTVPTMNNAKLTSTETSFN | 20-39 |
| 8 | B5R pep#2 | AKLTSTETSFNDKQKVTFTC | 29-48 |
| 9 | B5R pep#3 | FNDKQKVTFTCDQGYHSSDP | 38-57 |
| 10 | B5R pep#4 | TCDQGYHSSDPNAVCETDKW | 47-66 |
| 11 | B5R pep#5 | DPNAVCETDKWKYENPCKKM | 56-75 |
| 12 | B5R pep#6 | KWKYENPCKKMCTVSDYISE | 65-84 |
| 13 | B5R pep#7 | KMCTVSDYISELYNKPLYEV | 74-93 |
| 14 | B5R pep#8 | SELYNKPLYEVNSTMTLSCN | 83-102 |
| 15 | B5R pep#9 | EVNSTMTLSCNGETKYFRCE | 92-111 |
| 16 | B5R pep#10 | CNGETKYFRCEEKNGNTSWN | 101-120 |
| 17 | B5R pep#11 | CEEKNGNTSWNDTVTCPNAE | 110-129 |
| 18 | B5R pep#12 | WNDTVTCPNAECQPLQLEHG | 119-138 |
| 19 | B5R pep#13 | AECQPLQLEHGSCQPVKEKY | 128-147 |
| 20 | B5R pep#14 | HGSCQPVKEKYSFGEYMTIN | 137-156 |
| 21 | B5R pep#15 | KYSFGEYMTINCDVGYEVIG | 146-165 |
| 22 | B5R pep#16 | INCDVGYEVIGASYISCTAN | 155-174 |
| 23 | B5R pep#17 | IGASYISCTANSWNVIPSCQ | 164-183 |
| 24 | B5R pep#18 | ANSWNVIPSCQQKCDMPSLS | 173-192 |
| 25 | B5R pep#19 | CQQKCDMPSLSNGLISGSTF | 182-201 |
| 26 | B5R pep#20 | LSNGLISGSTFSIGGVIHLS | 191-210 |
| 27 | B5R pep#21 | TFSIGGVIHLSCKSGFTLTG | 200-219 |
| 28 | B5R pep#22 | LSCKSGFTLTGSPSSTCIDG | 209-228 |
| 29 | B5R pep#23 | TGSPSSTCIDGKWNPVLPIC | 218-237 |
| 30 | B5R pep#24 | DGKWNPVLPICVRTNEEFDP | 227-246 |
| 31 | B5R pep#25 | ICVRTNEEFDPVDDGPDDET | 236-255 |
| 32 | B5R pep#26 | DPVDDGPDDETDLSKLSKDV | 245-264 |
| 33 | B5R pep#27 | ETDLSKLSKDVVQYEQEIES | 254-273 |
| 34 | B5R pep#28 | DLSKLSKDVVQYEQEIESLE | 256-275 |

|              | First Mab |        |        |        |        |        |        |        |        |        |        |     |
| ------------ | ------ | ------ | ------ | ------ | ------ | ------ | ------ | ------ | ------ | ------ | ------ | --- |
| 2nd Mab | VMC-11 | VMC-19 | VMC-21 | VMC-20 | VMC-22 | VMC-25 | VMC-24 | VMC-32 | VMC-15 | VMC-29 | VMC-23 | rat |
| VMC-11 | 0 |   |   |   |   |   |   |   |   |   |   |   |
| VMC-19 | 109 | 0 | 101 |   |   |   |   |   |   |   |   |   |
| VMC-21 |   |   | 0 | 79 |   |   |   |   |   |   |   |   |
| VMC-20 | 95 | 84 | 5 | 50 |   |   | 48 |   |   | 97 | 96 | 93 |
| VMC-22 | 128 | 101 |   | 103 | 0 |   | 2 |   |   |   | 93 | 17 |
| VMC-25 | 106 | 102 |   | 95 | 102 | 0 | 102 | 81 |   |   |   |   |
| VMC-24 | 81 | 94 | 2 | 10 | 90 | 119 | 0 | 0 |   | 112 |   |   |
| VMC-32 | 119 | 2 |   | 94 | 106 | 107 | 97 |   |   | 117 | 76 |   |
| VMC-15 | 112 | 102 | 70 | 103 | 99 | 94 | 104 | 99 |   |   |   |   |
| VMC-29 | 82 | 88 | 84 | 90 | 76 | 100 | 97 | 100 | 0 | 0 | 72 | 81 |
| VMC-23 | -7 | 91 |   | 89 | 88 |   | 70 | 110 | 82 | 73 | 0 |   |
| rat | 105 | 102 | 95 | 96 | 115 |   | 104 |   | 96 | 53 | 96 | 0 |

MGAAASIQTTVNTLSERISSKLEQEANASAQTKCDIEIGNFYIRQNHGCNLTVKNMCSA
DADAQLDAVLSAATETYSGLTPEQKAYVPAMFTAALNIQTSVNTVVRDFENYVKQTCNS
SAVVDNKLKIQNVIIDECYGAPGSPTNLEFINTGSSKGNCAIKALMQLTTKATTQIAPK
QVAGTGVQ

FIG. 33B

ATGGGTGCCGCGGCAAGCATACAGACGACGGTGAATACACTCAGCGAACGTATCTCGTC
TAAATTAGAACAAGAAGCGAATGCTAGTGCTCAAACAAAATGTGATATAGAAATCGGAA
ATTTTTATATCCGACAAAACCATGGATGTAACCTCACTGTTAAAAATATGTGCTCTGCG
GACGCGGATGCTCAGTTGGATGCTGTGTTATCAGCCGCTACAGAAACATATAGTGGATT
AACACCGGAACAAAAGCATACGTGCCAGCTATGTTTACTGCTGCGTTAAACATTCAGA
CGAGTGTAAACACTGTTGTTAGAGATTTTGAAAATTATGTGAAACAGACTTGTAATTCT
AGCGCGGTCGTCGATAACAAATTAAAGATACAAAACGTAATCATAGATGAATGTTACGG
AGCCCCAGGATCTCCAACAAATTTGGAATTTATTAATACAGGATCTAGCAAAGGAAATT
GTGCCATTAAGGCGTTGATGCAATTGACGACTAAGGCCACTACTCAAATAGCACCTAAA
CAAGTTGCTGGTACAGGAGTTCAG

FIG. 33C

DPAMGAAASIQTTVNTLSERISSKLEQEANASAQTKCDIEIGNFYIRQNHGCNLTVKNM
CSADADAQLDAVLSAATETYSGLTPEQKAYVPAMFTAALNIQTSVNTVVRDFENYVKQT
CNSSAVVDNKLKIQNVIIDECYGAPGSPTNLEFINTGSSKGNCAIKALMQLTTKATTQI
APKQVAGTGVQHHHHHH

FIG. 33D

GATCCTGCCATGGGTGCCGCGGCAAGCATACAGACGACGGTGAATACACTCAGCGAACG
TATCTCGTCTAAATTAGAACAAGAAGCGAATGCTAGTGCTCAAACAAAATGTGATATAG
AAATCGGAATTTTTATATCCGACAAAACCATGGATGTAACCTCACTGTTAAAAATATG
TGCTCTGCGGACGCGGATGCTCAGTTGGATGCTGTGTTATCAGCCGCTACAGAAACATA
TAGTGGATTAACACCGGAACAAAAGCATACGTGCCAGCTATGTTTACTGCTGCGTTAA
ACATTCAGACGAGTGTAAACACTGTTGTTAGAGATTTTGAAAATTATGTGAAACAGACT
TGTAATTCTAGCGCGGTCGTCGATAACAAATTAAAGATACAAAACGTAATCATAGATGA
ATGTTACGGAGCCCCAGGATCTCCAACAAATTTGGAATTTATTAATACAGGATCTAGCA
AAGGAAATTGTGCCATTAAGGCGTTGATGCAATTGACGACTAAGGCCACTACTCAAATA
GCACCTAAACAAGTTGCTGGTACAGGAGTTCAGCACCATCATCACCATCAT

FIG. 34A

RLNQCMSANEAAITDAAVAVAAASSTHRKVASSTTQYDHKESCNGLYYQGSCYILHSDY
QLFSDAKANCTAESSTLPNKSDVLITWLIDYVEDTWGSDGNPITKTTSDYQDSDVSQEV
RKYFCVKTMN

FIG. 34B

CGCCTAAATCAATGCATGTCTGCTAACGAGGCTGCTATTACTGACGCCGCTGTTGCCGT
TGCTGCTGCATCATCTACTCATAGAAAGGTTGCGTCTAGCACTACACAATATGATCACA
AAGAAAGCTGTAATGGTTTATATTACCAGGGTTCTTGTTATATATTACATTCAGACTAC
CAGTTATTCTCGGATGCTAAAGCAAATTGCACTGCGGAATCATCAACACTACCCAATAA
ATCCGATGTCTTGATTACCTGGCTCATTGATTATGTTGAGGATACATGGGGATCTGATG
GTAATCCAATTACAAAAACTACATCCGATTATCAAGATTCTGATGTATCACAAGAAGTT
AGAAAGTATTTTTGTGTTAAAACAATGAAC

FIG. 34C

DPRLNQCMSANEAAITDAAVAVAAASSTHRKVASSTTQYDHKESCNGLYYQGSCYILHS
DYQLFSDAKANCTAESSTLPNKSDVLITWLIDYVEDTWGSDGNPITKTTSDYQDSDVSQ
EVRKYFCVKTMNHHHHHH

FIG. 34D

GATCCACGCCTAAATCAATGCATGTCTGCTAACGAGGCTGCTATTACTGACGCCGCTGT
TGCCGTTGCTGCTGCATCATCTACTCATAGAAAGGTTGCGTCTAGCACTACACAATATG
ATCACAAAGAAAGCTGTAATGGTTTATATTACCAGGGTTCTTGTTATATATTACATTCA
GACTACCAGTTATTCTCGGATGCTAAAGCAAATTGCACTGCGGAATCATCAACACTACC
CAATAAATCCGATGTCTTGATTACCTGGCTCATTGATTATGTTGAGGATACATGGGGAT
CTGATGGTAATCCAATTACAAAAACTACATCCGATTATCAAGATTCTGATGTATCACAA
GAAGTTAGAAAGTATTTTTGTGTTAAAACAATGAACCATCATCACCATCACCAT

FIG. 35A

TCTVPTMNNAKLTSTETSFNDKQKVTFTCDQGYHSSDPNAVCETDKWKYENPCKKMCTV
SDYISELYNKPLYEVNSTMTLSCNGETKYFRCEEKNGNTSWNDTVTCPNAECQPLQLEH
GSCQPVKEKYSFGEYMTINCDVGYEVIGASYISCTANSWNVIPSCQQKCDMPSLSNGLI
SGSTFSIGGVIHLSCKSGFTLTGSPSSTCIDGKWNPVLPICVRTNEEFDPVDDGPDDET
DLSKLSKDVVQYEQEIESLE

FIG. 35B

ACATGTACTGTACCCACTATGAATAACGCTAAATTAACGTCTACCGAAACATCGTTTAA
TGATAAACAGAAAGTTACGTTTACATGTGATCAGGGATATCATTCTTCGGATCCAAATG
CTGTCTGCGAAACAGATAAATGGAAATACGAAATCCATGCAAAAAATGTGCACAGTT
TCTGATTACATCTCTGAATTATATAATAAACCGCTATACGAAGTGAATTCCACCATGAC
ACTAAGTTGCAACGGCGAAACAAAATATTTTCGTTGCGAAGAAAAAAATGGAAATACTT
CTTGGAATGATACTGTTACGTGTCCTAATGCGGAATGTCAACCTCTTCAATTAGAACAC
GGATCGTGTCAACCAGTTAAAGAAAAATACTCATTTGGGGAATATATGACTATCAACTG
TGATGTTGGATATGAGGTTATTGGTGCTTCGTACATAAGTTGTACAGCTAATTCTTGGA
ATGTTATTCCATCATGTCAACAAAAATGTGATATGCCGTCTCTATCTAATGGATTAATT
TCCGGATCTACATTTTCTATCGGTGGCGTTATACATCTTAGTTGTAAAAGTGGTTTTAC
ACTAACGGGGTCTCCATCATCCACATGTATCGACGGTAAATGGAATCCCGTACTCCCAA
TATGTGTACGAACTAACGAAGAATTTGATCCAGTGGATGATGGTCCCGACGATGAGACA
GATTTGAGCAAACTCTCGAAAGACGTTGTACAATATGAACAAGAAATAGAATCGTTAGA
ATGA

FIG. 35C

DLHHHHHHTCTVPTMNNAKLTSTETSFNDKQKVTFTCDQGYHSSDPNAVCETDKWKYEN
PCKKMCTVSDYISELYNKPLYEVNSTMTLSCNGETKYFRCEEKNGNTSWNDTVTCPNAE
CQPLQLEHGSCQPVKEKYSFGEYMTINCDVGYEVIGASYISCTANSWNVIPSCQQKCDM
PSLSNGLISGSTFSIGGVIHLSCKSGFTLTGSPSSTCIDGKWNPVLPICVRTNEEFDPV
DDGPDDETDLSKLSKDVVQYEQEIESLE

FIG. 35D

```
GATCTGCATCATCACCATCATCACACATGTACTGTACCCACTATGAATAACGCTAAATT
AACGTCTACCGAAACATCGTTTAATGATAAACAGAAAGTTACGTTTACATGTGATCAGG
GATATCATTCTTCGGATCCAAATGCTGTCTGCGAAACAGATAAATGGAAATACGAAAAT
CCATGCAAAAAAATGTGCACAGTTTCTGATTACATCTCTGAATTATATAATAAACCGCT
ATACGAAGTGAATTCCACCATGACACTAAGTTGCAACGGCGAAACAAAATATTTTCGTT
GCGAAGAAAAAATGGAAATACTTCTTGGAATGATACTGTTACGTGTCCTAATGCGGAA
TGTCAACCTCTTCAATTAGAACACGGATCGTGTCAACCAGTTAAAGAAAAATACTCATT
TGGGGAATATATGACTATCAACTGTGATGTTGGATATGAGGTTATTGGTGCTTCGTACA
TAAGTTGTACAGCTAATTCTTGGAATGTTATTCCATCATGTCAACAAAATGTGATATG
CCGTCTCTATCTAATGGATTAATTTCCGGATCTACATTTTCTATCGGTGGCGTTATACA
TCTTAGTTGTAAAAGTGGTTTTACACTAACGGGGTCTCCATCATCCACATGTATCGACG
GTAAATGGAATCCCGTACTCCAATATGTGTACGAACTAACGAAGAATTTGATCCAGTG
GATGATGGTCCCGACGATGAGACAGATTTGAGCAAACTCTCGAAAGACGTTGTACAATA
TGAACAAGAAATAGAATCGTTAGAATGA
```

FIG. 36A

MMTPENDEEQTSVFSATVYGDKIQGKNKRKRVIGLCIRISMVISLLSMITMSAFLIVRL
NQCMSANEAAITDAAVAVAAASSTHRKVASSTTQYDHKESCNGLYYQGSCYILHSDYQL
FSDAKANCTAESSTLPNKSDVLITWLIDYVEDTWGSDGNPITKTTSDYQDSDVSQEVRK
YFCVKTMN

FIG. 36B

MMTPENDEEQTSVFSATVYGDKIQGKNKRKRVIGICIRISMVISLLSMITMSAFLIVRL
NQCMSANEAAITDATAVAAALSTHRKVASSTTQYKHQESCNGLYYQGSCYIFHSDYQLF
SDAKANCATESSTLPNKSDVLTTWLIDYVEDTWGSDGNPITKTTTDYQDSDVSQEVRKY
FCVKTMN

FIG. 36C

MMTPENDEEQTSVFSATVYGDKIQGKNKRKRVIGLCIRISMVISLLSMITMSAFLIVRLN
::::::::::::::::::::::::::::::::::::.::::::::::::::::::::::
MMTPENDEEQTSVFSATVYGDKIQGKNKRKRVIGICIRISMVISLLSMITMSAFLIVRLN

QCMSANEAAITDAAVAVAAASSTHRKVASSTTQYDHKESCNGLYYQGSCYILHSDYQLFS
:::::::::::::. ::::: :::::::::::: :.:::::::::::::::.::::::
QCMSANEAAITDAT-AVAAALSTHRKVASSTTQYKHQESCNGLYYQGSCYIFHSDYQLFS

DAKANCTAESSTLPNKSDVLITWLIDYVEDTWGSDGNPITKTTSDYQDSDVSQEVRKYFC
:::::::..::::::::::: :::::::::::::::::::::::.::::::::::::::
DAKANCATESSTLPNKSDVLTTWLIDYVEDTWGSDGNPITKTTTDYQDSDVSQEVRKYFC

VKTMN
:::::
VKTMN

FIG. 36D

```
RLNQCMSANEAAITDATAVAAALSTHRKVASSTTQYKHQESCNGLYYQGSCYIFHSDYQ
LFSDAKANCATESSTLPNKSDVLTTWLIDYVEDTWGSDGNPITKTTTDYQDSDVSQEVR
KYFCVKTMN
```

FIG. 36E

```
RLNQCMSANEAAITDAAVAVAAASSTHRKVASSTTQYDHKESCNGLYYQGSCYILHSDYQ
:::::::.:::::::. ::::: ::::::::::::: :.:::::::::::::.:::::
RLNQCMSANEAAITDAT-AVAAALSTHRKVASSTTQYKHQESCNGLYYQGSCYIFHSDYQ

LFSDAKANCTAESSTLPNKSDVLITWLIDYVEDTWGSDGNPITKTTSDYQDSDVSQEVRK
::::::::..:::::::::::::::: :::::::::::::::::::.::::::::::::
LFSDAKANCATESSTLPNKSDVLTTWLIDYVEDTWGSDGNPITKTTTDYQDSDVSQEVRK

YFCVKTMN
::::::::
YFCVKTMN
```

FIG. 37A

MGAAASIQTTVNTLSERISSKLEQEANASAQTKCDIEIGNFYIRQNHGCNLTVKNMCSA
DADAQLDAVLSAATETYSGLTPEQKAYVPAMFTAALNIQTSVNTVVRDFENYVKQTCNS
SAVVDNKLKIQNVIIDECYGAPGSPTNLEFINTGSSKGNCAIKALMQLTTKATTQIAPK
QVAGTGVQFYMIVIGVIILAALFMYYAKRMLFTSTNDKIKLILANKENVHWTTYMDTFF
RTSPMVIATTDMQN

FIG. 37B

MGAAASIQTTVNTLSERISSKLEQEANASAQTKCDIEIGNFYIRQNHGCNLTVKNMCSA
DADAQLDAVLSAATETYSGLTPEQKAYVPAMFTAALNIQTSVNTVVRDFENYVKQTCNS
SAVVDNKLKIQNVIIDECYGAPGSPTNLEFINTGSSKGNCAIKALMQLTTKATTQIAPR
QVAGTGVQFYMIVIGVIILAALFMYYAKRMLFTSTNDKIKLILANKENVHWTTYMDTFF
RTSPMVIATTDIQN

FIG. 37C

MGAAASIQTTVNTLSERISSKLEQEANASAQTKCDIEIGNFYIRQNHGCNLTVKNMCSAD
::::::::::::::::::::::::::::::::::::::::::::::::::::::::::
MGAAASIQTTVNTLSERISSKLEQEANASAQTKCDIEIGNFYIRQNHGCNLTVKNMCSAD

ADAQLDAVLSAATETYSGLTPEQKAYVPAMFTAALNIQTSVNTVVRDFENYVKQTCNSSA
::::::::::::::::::::::::::::::::::::::::::::::::::::::::::
ADAQLDAVLSAATETYSGLTPEQKAYVPAMFTAALNIQTSVNTVVRDFENYVKQTCNSSA

VVDNKLKIQNVIIDECYGAPGSPTNLEFINTGSSKGNCAIKALMQLTTKATTQIAPKQVA
::::::::::::::::::::::::::::::::::::::::::::::::::::::.:::
VVDNKLKIQNVIIDECYGAPGSPTNLEFINTGSSKGNCAIKALMQLTTKATTQIAPRQVA

GTGVQFYMIVIGVIILAALFMYYAKRMLFTSTNDKIKLILANKENVHWTTYMDTFFRTSP
::::::::::::::::::::::::::::::::::::::::::::::::::::::::::
GTGVQFYMIVIGVIILAALFMYYAKRMLFTSTNDKIKLILANKENVHWTTYMDTFFRTSP

MVIATTDMQN
:::::::.::
MVIATTDIQN

FIG. 37D

MGAAASIQTTVNTLSERISSKLEQEANASAQTKCDIEIGNFYIRQNHGCNLTVKNMCSA
DADAQLDAVLSAATETYSGLTPEQKAYVPAMFTAALNIQTSVNTVVRDFENYVKQTCNS
SAVVDNKLKIQNVIIDECYGAPGSPTNLEFINTGSSKGNCAIKALMQLTTKATTQIAPR
QVAGTGVQ

FIG. 37E

MGAAASIQTTVNTLSERISSKLEQEANASAQTKCDIEIGNFYIRQNHGCNLTVKNMCSAD
::::::::::::::::::::::::::::::::::::::::::::::::::::::::::
MGAAASIQTTVNTLSERISSKLEQEANASAQTKCDIEIGNFYIRQNHGCNLTVKNMCSAD

ADAQLDAVLSAATETYSGLTPEQKAYVPAMFTAALNIQTSVNTVVRDFENYVKQTCNSSA
::::::::::::::::::::::::::::::::::::::::::::::::::::::::::::
ADAQLDAVLSAATETYSGLTPEQKAYVPAMFTAALNIQTSVNTVVRDFENYVKQTCNSSA

VVDNKLKIQNVIIDECYGAPGSPTNLEFINTGSSKGNCAIKALMQLTTKATTQIAPKQVA
::::::::::::::::::::::::::::::::::::::::::::::::::::::.:::
VVDNKLKIQNVIIDECYGAPGSPTNLEFINTGSSKGNCAIKALMQLTTKATTQIAPRQVA

GTGVQ
:::::
GTGVQ

FIG. 38A

MKTISVVTLLCVLPAVVYSTCTVPTMNNAKLTSTETSFNDKQKVTFTCDQGYHSSDPNA
VCETDKWKYENPCKKMCTVSDYISELYNKPLYEVNSTMTLSCNGETKYFRCEEKNGNTS
WNDTVTCPNAECQPLQLEHGSCQPVKEKYSFGEYMTINCDVGYEVIGASYISCTANSWN
VIPSCQQKCDMPSLSNGLISGSTFSIGGVIHLSCKSGFTLTGSPSSTCIDGKWNPVLPI
CVRTNEEFDPVDDGPDDETDLSKLSKDVVQYEQEIESLEATYHIIVALTIMGVIFLIS
VIVLVCSCDKNNDQYKFHKLLP

FIG. 38B

MKTISVVTLLCVLPAVVYSTCTVPTMNNAKLTSTETSFNDKQKVTFTCDSGYYSLDPNA
VCETDKWKYENPCKKMCTVSDYVSELYNKPLYEVNAIITLICKDETKYFRCEEKNGNTS
WNDTVTCPNAECQSLQLDHGSCQPVKGKYSFGEHITINCDVGYEVIGASYITCTANSWN
VIPSCQQKCDIPSLSNGLISGSTFSIGGVIHLSCKSGFILTGSPSSTCIDGKWNPVLPI
CIRSNEEFDPVEDGPDDETDLSKLSKDVVQYEQEIESLEATYHIIVALTIMGVIFLIS
VIVLVCSCNKNNDQYKFHKLLL

FIG. 38C

MKTISVVTLLCVLPAVVYSTCTVPTMNNAKLTSTETSFNDKQKVTFTCDQGYHSSDPNAV
::::::::::::::::::::::::::::::::::::::::::::::::::::.::.: :::::
MKTISVVTLLCVLPAVVYSTCTVPTMNNAKLTSTETSFNDKQKVTFTCDSGYYSLDPNAV

CETDKWKYENPCKKMCTVSDYISELYNKPLYEVNSTMTLSCNGETKYFRCEEKNGNTSWN
:::::::::::::::::::::.::::::::::::::::. .:: :.. :::::::::::::::
CETDKWKYENPCKKMCTVSDYVSELYNKPLYEVNAIITLICKDETKYFRCEEKNGNTSWN

DTVTCPNAECQPLQLEHGSCQPVKEKYSFGEYMTINCDVGYEVIGASYISCTANSWNVIP
:::::::::: :::.::::::::: :::::.:::::.:::::::::::::::::::::::
DTVTCPNAECQSLQLDHGSCQPVKGKYSFGEHITINCDVGYEVIGASYITCTANSWNVIP

SCQQKCDMPSLSNGLISGSTFSIGGVIHLSCKSGFTLTGSPSSTCIDGKWNPVLPICVRT
:::::::.:::::::::::::::::::::::::::.::::::::::::::::::::::.:.
SCQQKCDIPSLSNGLISGSTFSIGGVIHLSCKSGFILTGSPSSTCIDGKWNPVLPICIRS

NEEFDPVDDGPDDETDLSKLSKDVVQYEQEIESLEATYHIIVALTIMGVIFLISVIVLV
:::::::.::::::::::::::::::::::::::>.:::::::::::::::.:::::::::::
NEEFDPVEDGPDDETDLSKLSKDVVQYEQEIESLEATYHIIVALTIMGVIFLISVIVLV

CSCDKNNDQYKFHKLLP
:::.:::::::::::::
CSCNKNNDQYKFHKLLL

FIG. 38D

TCTVPTMNNAKLTSTETSFNDKQKVTFTCDSGYYSLDPNAVCETDKWKYENPCKKMCTV
SDYVSELYNKPLYEVNAIITLICKDETKYFRCEEKNGNTSWNDTVTCPNAECQSLQLDH
GSCQPVKGKYSFGEHITINCDVGYEVIGASYITCTANSWNVIPSCQQKCDIPSLSNGLI
SGSTFSIGGVIHLSCKSGFILTGSPSSTCIDGKWNPVLPICIRSNEEFDPVEDGPDDET
DLSKLSKDVVQYEQEIESLE

FIG. 38E

TCTVPTMNNAKLTSTETSFNDKQKVTFTCDQGYHSSDPNAVCETDKWKYENPCKKMCTVS
::::::::::::::::::::::::::::::::.::.:  :::::::::::::::::::::
TCTVPTMNNAKLTSTETSFNDKQKVTFTCDSGYYSLDPNAVCETDKWKYENPCKKMCTVS

DYISELYNKPLYEVNSTMTLSCNGETKYFRCEEKNGNTSWNDTVTCPNAECQPLQLEHGS
::.::::::::::::. .::  :.  ::::::::::::::::::::::::::: :::.::
DYVSELYNKPLYEVNAIITLICKDETKYFRCEEKNGNTSWNDTVTCPNAECQSLQLDHGS

CQPVKEKYSFGEYMTINCDVGYEVIGASYISCTANSWNVIPSCQQKCDMPSLSNGLISGS
:::::  :::::..:::::::::::::::.::::::::::::::::::.:::::::::::
CQPVKGKYSFGEHITINCDVGYEVIGASYITCTANSWNVIPSCQQKCDIPSLSNGLISGS

TFSIGGVIHLSCKSGFTLTGSPSSTCIDGKWNPVLPICVRTNEEFDPVDDGPDDETDLSK
:::::::::::::::: :::::::::::::::::::::..:.:::::::.::::::::::
TFSIGGVIHLSCKSGFILTGSPSSTCIDGKWNPVLPICIRSNEEFDPVEDGPDDETDLSK

LSKDVVQYEQEIESLE
::::::::::::::::
LSKDVVQYEQEIESLE

SEQUENCE LISTING

<160> NUMBER OF SEQ ID NOS: 43

<210> SEQ ID NO 1
<211> LENGTH: 185
<212> TYPE: PRT
<213> ORGANISM: Artificial sequence
<220> FEATURE:
<223> OTHER INFORMATION: L1R(185t)

<400> SEQUENCE: 1

Met Gly Ala Ala Ala Ser Ile Gln Thr Thr Val Asn Thr Leu Ser Glu
1               5                   10                  15

Arg Ile Ser Ser Lys Leu Glu Gln Glu Ala Asn Ala Ser Ala Gln Thr
            20                  25                  30

Lys Cys Asp Ile Glu Ile Gly Asn Phe Tyr Ile Arg Gln Asn His Gly
        35                  40                  45

Cys Asn Leu Thr Val Lys Asn Met Cys Ser Ala Asp Ala Asp Ala Gln

```
                50                  55                  60
Leu Asp Ala Val Leu Ser Ala Ala Thr Glu Thr Tyr Ser Gly Leu Thr
 65                  70                  75                  80

Pro Glu Gln Lys Ala Tyr Val Pro Ala Met Phe Thr Ala Ala Leu Asn
                 85                  90                  95

Ile Gln Thr Ser Val Asn Thr Val Arg Asp Phe Glu Asn Tyr Val
                100                 105                 110

Lys Gln Thr Cys Asn Ser Ser Ala Val Val Asp Asn Lys Leu Lys Ile
                115                 120                 125

Gln Asn Val Ile Ile Asp Glu Cys Tyr Gly Ala Pro Gly Ser Pro Thr
            130                 135                 140

Asn Leu Glu Phe Ile Asn Thr Gly Ser Ser Lys Gly Asn Cys Ala Ile
145                 150                 155                 160

Lys Ala Leu Met Gln Leu Thr Thr Lys Ala Thr Thr Gln Ile Ala Pro
                165                 170                 175

Lys Gln Val Ala Gly Thr Gly Val Gln
            180                 185

<210> SEQ ID NO 2
<211> LENGTH: 555
<212> TYPE: DNA
<213> ORGANISM: Artificial sequence
<220> FEATURE:
<223> OTHER INFORMATION: L1R(185t)

<400> SEQUENCE: 2
atgggtgccg cggcaagcat acagacgacg gtgaatacac tcagcgaacg tatctcgtct    60
aaattagaac aagaagcgaa tgctagtgct caaacaaaat gtgatataga aatcggaaat   120
ttttatatcc gacaaaacca tggatgtaac ctcactgtta aaaatatgtg ctctgcggac   180
gcggatgctc agttggatgc tgtgttatca gccgctacag aaacatatag tggattaaca   240
ccggaacaaa aagcatacgt gccagctatg tttactgctg cgttaaacat tcagacgagt   300
gtaaacactg ttgttagaga ttttgaaaat tatgtgaaac agacttgtaa ttctagcgcg   360
gtcgtcgata acaaattaaa gatacaaaac gtaatcatag atgaatgtta cggagcccca   420
ggatctccaa caaatttgga atttattaat acaggatcta gcaaaggaaa ttgtgccatt   480
aaggcgttga tgcaattgac gactaaggcc actactcaaa tagcacctaa acaagttgct   540
ggtacaggag ttcag                                                    555

<210> SEQ ID NO 3
<211> LENGTH: 128
<212> TYPE: PRT
<213> ORGANISM: Artificial sequence
<220> FEATURE:
<223> OTHER INFORMATION: A33Rt

<400> SEQUENCE: 3

Arg Leu Asn Gln Cys Met Ser Ala Asn Glu Ala Ala Ile Thr Asp Ala
 1               5                  10                  15

Ala Val Ala Val Ala Ala Ala Ser Ser Thr His Arg Lys Val Ala Ser
            20                  25                  30

Ser Thr Thr Gln Tyr Asp His Lys Glu Ser Cys Asn Gly Leu Tyr Tyr
            35                  40                  45

Gln Gly Ser Cys Tyr Ile Leu His Ser Asp Tyr Gln Leu Phe Ser Asp
        50                  55                  60

Ala Lys Ala Asn Cys Thr Ala Glu Ser Ser Thr Leu Pro Asn Lys Ser
```

```
                   65                  70                  75                  80
Asp Val Leu Ile Thr Trp Leu Ile Asp Tyr Val Glu Asp Thr Trp Gly
                        85                  90                  95
Ser Asp Gly Asn Pro Ile Thr Lys Thr Thr Ser Asp Tyr Gln Asp Ser
                    100                 105                 110
Asp Val Ser Gln Glu Val Arg Lys Tyr Phe Cys Val Lys Thr Met Asn
                115                 120                 125

<210> SEQ ID NO 4
<211> LENGTH: 384
<212> TYPE: DNA
<213> ORGANISM: Artificial sequence
<220> FEATURE:
<223> OTHER INFORMATION: A33Rt

<400> SEQUENCE: 4
cgcctaaatc aatgcatgtc tgctaacgag gctgctatta ctgacgccgc tgttgccgtt      60
gctgctgcat catctactca tagaaaggtt gcgtctagca ctacacaata tgatcacaaa     120
gaaagctgta atggtttata ttaccagggt tcttgttata tattacattc agactaccag     180
ttattctcgg atgctaaagc aaattgcact gcggaatcat caacactacc caataaatcc     240
gatgtcttga ttacctggct cattgattat gttgaggata catggggatc tgatggtaat     300
ccaattacaa aaactacatc cgattatcaa gattctgatg tatcacaaga agttagaaag     360
tattttgtg ttaaaacaat gaac                                            384

<210> SEQ ID NO 5
<211> LENGTH: 256
<212> TYPE: PRT
<213> ORGANISM: Artificial sequence
<220> FEATURE:
<223> OTHER INFORMATION: B5Rt

<400> SEQUENCE: 5

Thr Cys Thr Val Pro Thr Met Asn Asn Ala Lys Leu Thr Ser Thr Glu
1               5                  10                  15
Thr Ser Phe Asn Asp Lys Gln Lys Val Thr Phe Thr Cys Asp Gln Gly
                    20                  25                  30
Tyr His Ser Ser Asp Pro Asn Ala Val Cys Glu Thr Asp Lys Trp Lys
                35                  40                  45
Tyr Glu Asn Pro Cys Lys Lys Met Cys Thr Val Ser Asp Tyr Ile Ser
            50                  55                  60
Glu Leu Tyr Asn Lys Pro Leu Tyr Glu Val Asn Ser Thr Met Thr Leu
65                  70                  75                  80
Ser Cys Asn Gly Glu Thr Lys Tyr Phe Arg Cys Glu Glu Lys Asn Gly
                    85                  90                  95
Asn Thr Ser Trp Asn Asp Thr Val Thr Cys Pro Asn Ala Glu Cys Gln
                100                 105                 110
Pro Leu Gln Leu Glu His Gly Ser Cys Gln Pro Val Lys Glu Lys Tyr
            115                 120                 125
Ser Phe Gly Glu Tyr Met Thr Ile Asn Cys Asp Val Gly Tyr Glu Val
        130                 135                 140
Ile Gly Ala Ser Tyr Ile Ser Cys Thr Ala Asn Ser Trp Asn Val Ile
145                 150                 155                 160
Pro Ser Cys Gln Gln Lys Cys Asp Met Pro Ser Leu Ser Asn Gly Leu
                165                 170                 175
Ile Ser Gly Ser Thr Phe Ser Ile Gly Gly Val Ile His Leu Ser Cys
```

```
                    180                 185                 190
Lys Ser Gly Phe Thr Leu Thr Gly Ser Pro Ser Thr Cys Ile Asp
            195                 200                 205

Gly Lys Trp Asn Pro Val Leu Pro Ile Cys Val Arg Thr Asn Glu Glu
    210                 215                 220

Phe Asp Pro Val Asp Asp Gly Pro Asp Asp Glu Thr Asp Leu Ser Lys
225                 230                 235                 240

Leu Ser Lys Asp Val Val Gln Tyr Glu Gln Glu Ile Glu Ser Leu Glu
                245                 250                 255

<210> SEQ ID NO 6
<211> LENGTH: 771
<212> TYPE: DNA
<213> ORGANISM: Artificial sequence
<220> FEATURE:
<223> OTHER INFORMATION: B5Rt

<400> SEQUENCE: 6
acatgtactg tacccactat gaataacgct aaattaacgt ctaccgaaac atcgtttaat      60
gataaacaga aagttacgtt tacatgtgat cagggatatc attcttcgga tccaaatgct     120
gtctgcgaaa cagataaatg gaaatacgaa atccatgca aaaaaatgtg cacagtttct     180
gattacatct ctgaattata taataaaccg ctatacgaag tgaattccac catgacacta     240
agttgcaacg gcgaaacaaa atattttcgt tgcgaagaaa aaatggaaa tacttcttgg      300
aatgatactg ttacgtgtcc taatgcggaa tgtcaacctc ttcaattaga acacggatcg     360
tgtcaaccag ttaaagaaaa atactcattt ggggaatata tgactatcaa ctgtgatgtt     420
ggatatgagg ttattggtgc ttcgtacata agttgtacag ctaattcttg gaatgttatt     480
ccatcatgtc aacaaaaatg tgatatgccg tctctatcta atggattaat ttccggatct     540
acattttcta tcggtggcgt tatacatctt agttgtaaaa gtggttttac actaacgggg     600
tctccatcat ccacatgtat cgacggtaaa tggaatcccg tactcccaat atgtgtacga     660
actaacgaag aatttgatcc agtggatgat ggtcccgacg atgagacaga tttgagcaaa     720
ctctcgaaag acgttgtaca atatgaacaa gaaatagaat cgttagaatg a              771

<210> SEQ ID NO 7
<211> LENGTH: 20
<212> TYPE: PRT
<213> ORGANISM: Artificial sequence
<220> FEATURE:
<223> OTHER INFORMATION: B5R pep#1

<400> SEQUENCE: 7

Thr Cys Thr Val Pro Thr Met Asn Asn Ala Lys Leu Thr Ser Thr Glu
1               5                   10                  15

Thr Ser Phe Asn
            20

<210> SEQ ID NO 8
<211> LENGTH: 20
<212> TYPE: PRT
<213> ORGANISM: Artificial sequence
<220> FEATURE:
<223> OTHER INFORMATION: B5R pep#2

<400> SEQUENCE: 8

Ala Lys Leu Thr Ser Thr Glu Thr Ser Phe Asn Asp Lys Gln Lys Val
1               5                   10                  15
```

```
Thr Phe Thr Cys
            20

<210> SEQ ID NO 9
<211> LENGTH: 20
<212> TYPE: PRT
<213> ORGANISM: Artificial sequence
<220> FEATURE:
<223> OTHER INFORMATION: B5R pep#3

<400> SEQUENCE: 9

Phe Asn Asp Lys Gln Lys Val Thr Phe Thr Cys Asp Gln Gly Tyr His
1               5                   10                  15

Ser Ser Asp Pro
            20

<210> SEQ ID NO 10
<211> LENGTH: 20
<212> TYPE: PRT
<213> ORGANISM: Artificial sequence
<220> FEATURE:
<223> OTHER INFORMATION: B5R pep#4

<400> SEQUENCE: 10

Thr Cys Asp Gln Gly Tyr His Ser Ser Asp Pro Asn Ala Val Cys Glu
1               5                   10                  15

Thr Asp Lys Trp
            20

<210> SEQ ID NO 11
<211> LENGTH: 20
<212> TYPE: PRT
<213> ORGANISM: Artificial sequence
<220> FEATURE:
<223> OTHER INFORMATION: B5R pep#5

<400> SEQUENCE: 11

Asp Pro Asn Ala Val Cys Glu Thr Asp Lys Trp Lys Tyr Glu Asn Pro
1               5                   10                  15

Cys Lys Lys Met
            20

<210> SEQ ID NO 12
<211> LENGTH: 20
<212> TYPE: PRT
<213> ORGANISM: Artificial sequence
<220> FEATURE:
<223> OTHER INFORMATION: B5R pep#6

<400> SEQUENCE: 12

Lys Trp Lys Tyr Glu Asn Pro Cys Lys Lys Met Cys Thr Val Ser Asp
1               5                   10                  15

Tyr Ile Ser Glu
            20

<210> SEQ ID NO 13
<211> LENGTH: 20
<212> TYPE: PRT
<213> ORGANISM: Artificial sequence
<220> FEATURE:
<223> OTHER INFORMATION: B5R pep#7

<400> SEQUENCE: 13

Lys Met Cys Thr Val Ser Asp Tyr Ile Ser Glu Leu Tyr Asn Lys Pro
1               5                   10                  15
```

```
Leu Tyr Glu Val
            20

<210> SEQ ID NO 14
<211> LENGTH: 20
<212> TYPE: PRT
<213> ORGANISM: Artificial sequence
<220> FEATURE:
<223> OTHER INFORMATION: B5R pep#8

<400> SEQUENCE: 14

Ser Glu Leu Tyr Asn Lys Pro Leu Tyr Glu Val Asn Ser Thr Met Thr
1               5                   10                  15

Leu Ser Cys Asn
            20

<210> SEQ ID NO 15
<211> LENGTH: 20
<212> TYPE: PRT
<213> ORGANISM: Artificial sequence
<220> FEATURE:
<223> OTHER INFORMATION: B5R pep#9

<400> SEQUENCE: 15

Glu Val Asn Ser Thr Met Thr Leu Ser Cys Asn Gly Glu Thr Lys Tyr
1               5                   10                  15

Phe Arg Cys Glu
            20

<210> SEQ ID NO 16
<211> LENGTH: 20
<212> TYPE: PRT
<213> ORGANISM: Artificial sequence
<220> FEATURE:
<223> OTHER INFORMATION: B5R pep#10

<400> SEQUENCE: 16

Cys Asn Gly Glu Thr Lys Tyr Phe Arg Cys Glu Glu Lys Asn Gly Asn
1               5                   10                  15

Thr Ser Trp Asn
            20

<210> SEQ ID NO 17
<211> LENGTH: 20
<212> TYPE: PRT
<213> ORGANISM: Artificial sequence
<220> FEATURE:
<223> OTHER INFORMATION: B5R pep#11

<400> SEQUENCE: 17

Cys Glu Glu Lys Asn Gly Asn Thr Ser Trp Asn Asp Thr Val Thr Cys
1               5                   10                  15

Pro Asn Ala Glu
            20

<210> SEQ ID NO 18
<211> LENGTH: 20
<212> TYPE: PRT
<213> ORGANISM: Artificial sequence
<220> FEATURE:
<223> OTHER INFORMATION: B5R pep#12

<400> SEQUENCE: 18

Trp Asn Asp Thr Val Thr Cys Pro Asn Ala Glu Cys Gln Pro Leu Gln
```

```
                1               5                  10                  15

Leu Glu His Gly
            20

<210> SEQ ID NO 19
<211> LENGTH: 20
<212> TYPE: PRT
<213> ORGANISM: Artificial sequence
<220> FEATURE:
<223> OTHER INFORMATION: B5R pep#13

<400> SEQUENCE: 19

Ala Glu Cys Gln Pro Leu Gln Leu Glu His Gly Ser Cys Gln Pro Val
1               5                  10                  15

Lys Glu Lys Tyr
            20

<210> SEQ ID NO 20
<211> LENGTH: 20
<212> TYPE: PRT
<213> ORGANISM: Artificial sequence
<220> FEATURE:
<223> OTHER INFORMATION: B5R pep#14

<400> SEQUENCE: 20

His Gly Ser Cys Gln Pro Val Lys Glu Lys Tyr Ser Phe Gly Glu Tyr
1               5                  10                  15

Met Thr Ile Asn
            20

<210> SEQ ID NO 21
<211> LENGTH: 20
<212> TYPE: PRT
<213> ORGANISM: Artificial sequence
<220> FEATURE:
<223> OTHER INFORMATION: B5R pep#15

<400> SEQUENCE: 21

Lys Tyr Ser Phe Gly Glu Tyr Met Thr Ile Asn Cys Asp Val Gly Tyr
1               5                  10                  15

Glu Val Ile Gly
            20

<210> SEQ ID NO 22
<211> LENGTH: 20
<212> TYPE: PRT
<213> ORGANISM: Artificial sequence
<220> FEATURE:
<223> OTHER INFORMATION: B5R pep#16

<400> SEQUENCE: 22

Ile Asn Cys Asp Val Gly Tyr Glu Val Ile Gly Ala Ser Tyr Ile Ser
1               5                  10                  15

Cys Thr Ala Asn
            20

<210> SEQ ID NO 23
<211> LENGTH: 20
<212> TYPE: PRT
<213> ORGANISM: Artificial sequence
<220> FEATURE:
<223> OTHER INFORMATION: B5R pep#17

<400> SEQUENCE: 23
```

```
Ile Gly Ala Ser Tyr Ile Ser Cys Thr Ala Asn Ser Trp Asn Val Ile
1               5                   10                  15

Pro Ser Cys Gln
            20

<210> SEQ ID NO 24
<211> LENGTH: 20
<212> TYPE: PRT
<213> ORGANISM: Artificial sequence
<220> FEATURE:
<223> OTHER INFORMATION: B5R pep#18

<400> SEQUENCE: 24

Ala Asn Ser Trp Asn Val Ile Pro Ser Cys Gln Gln Lys Cys Asp Met
1               5                   10                  15

Pro Ser Leu Ser
            20

<210> SEQ ID NO 25
<211> LENGTH: 20
<212> TYPE: PRT
<213> ORGANISM: Artificial sequence
<220> FEATURE:
<223> OTHER INFORMATION: B5R pep#19

<400> SEQUENCE: 25

Cys Gln Gln Lys Cys Asp Met Pro Ser Leu Ser Asn Gly Leu Ile Ser
1               5                   10                  15

Gly Ser Thr Phe
            20

<210> SEQ ID NO 26
<211> LENGTH: 20
<212> TYPE: PRT
<213> ORGANISM: Artificial sequence
<220> FEATURE:
<223> OTHER INFORMATION: B5R pep#20

<400> SEQUENCE: 26

Leu Ser Asn Gly Leu Ile Ser Gly Ser Thr Phe Ser Ile Gly Gly Val
1               5                   10                  15

Ile His Leu Ser
            20

<210> SEQ ID NO 27
<211> LENGTH: 20
<212> TYPE: PRT
<213> ORGANISM: Artificial sequence
<220> FEATURE:
<223> OTHER INFORMATION: B5R pep#21

<400> SEQUENCE: 27

Thr Phe Ser Ile Gly Gly Val Ile His Leu Ser Cys Lys Ser Gly Phe
1               5                   10                  15

Thr Leu Thr Gly
            20

<210> SEQ ID NO 28
<211> LENGTH: 20
<212> TYPE: PRT
<213> ORGANISM: Artificial sequence
<220> FEATURE:
<223> OTHER INFORMATION: B5R pep#22

<400> SEQUENCE: 28
```

-continued

```
Leu Ser Cys Lys Ser Gly Phe Thr Leu Thr Gly Ser Pro Ser Ser Thr
1               5                   10                  15

Cys Ile Asp Gly
            20

<210> SEQ ID NO 29
<211> LENGTH: 20
<212> TYPE: PRT
<213> ORGANISM: Artificial sequence
<220> FEATURE:
<223> OTHER INFORMATION: B5R pep#23

<400> SEQUENCE: 29

Thr Gly Ser Pro Ser Ser Thr Cys Ile Asp Gly Lys Trp Asn Pro Val
1               5                   10                  15

Leu Pro Ile Cys
            20

<210> SEQ ID NO 30
<211> LENGTH: 20
<212> TYPE: PRT
<213> ORGANISM: Artificial sequence
<220> FEATURE:
<223> OTHER INFORMATION: B5R pep#24

<400> SEQUENCE: 30

Asp Gly Lys Trp Asn Pro Val Leu Pro Ile Cys Val Arg Thr Asn Glu
1               5                   10                  15

Glu Phe Asp Pro
            20

<210> SEQ ID NO 31
<211> LENGTH: 20
<212> TYPE: PRT
<213> ORGANISM: Artificial sequence
<220> FEATURE:
<223> OTHER INFORMATION: B5R pep#25

<400> SEQUENCE: 31

Ile Cys Val Arg Thr Asn Glu Glu Phe Asp Pro Val Asp Gly Pro
1               5                   10                  15

Asp Asp Glu Thr
            20

<210> SEQ ID NO 32
<211> LENGTH: 20
<212> TYPE: PRT
<213> ORGANISM: Artificial sequence
<220> FEATURE:
<223> OTHER INFORMATION: B5R pep#26

<400> SEQUENCE: 32

Asp Pro Val Asp Asp Gly Pro Asp Asp Glu Thr Asp Leu Ser Lys Leu
1               5                   10                  15

Ser Lys Asp Val
            20

<210> SEQ ID NO 33
<211> LENGTH: 20
<212> TYPE: PRT
<213> ORGANISM: Artificial sequence
<220> FEATURE:
<223> OTHER INFORMATION: B5R pep#27
```

```
<400> SEQUENCE: 33

Glu Thr Asp Leu Ser Lys Leu Ser Lys Asp Val Val Gln Tyr Glu Gln
1               5                   10                  15

Glu Ile Glu Ser
            20

<210> SEQ ID NO 34
<211> LENGTH: 20
<212> TYPE: PRT
<213> ORGANISM: Artificial sequence
<220> FEATURE:
<223> OTHER INFORMATION: B5R pep#28

<400> SEQUENCE: 34

Asp Leu Ser Lys Leu Ser Lys Asp Val Val Gln Tyr Glu Gln Glu Ile
1               5                   10                  15

Glu Ser Leu Glu
            20

<210> SEQ ID NO 35
<211> LENGTH: 185
<212> TYPE: PRT
<213> ORGANISM: Vaccinia virus
<220> FEATURE:
<221> NAME/KEY: MISC_FEATURE
<223> OTHER INFORMATION: Vaccinia A33R (strain WR)

<400> SEQUENCE: 35

Met Met Thr Pro Glu Asn Asp Glu Glu Gln Thr Ser Val Phe Ser Ala
1               5                   10                  15

Thr Val Tyr Gly Asp Lys Ile Gln Gly Lys Asn Lys Arg Lys Arg Val
                20                  25                  30

Ile Gly Leu Cys Ile Arg Ile Ser Met Val Ile Ser Leu Leu Ser Met
            35                  40                  45

Ile Thr Met Ser Ala Phe Leu Ile Val Arg Leu Asn Gln Cys Met Ser
        50                  55                  60

Ala Asn Glu Ala Ala Ile Thr Asp Ala Ala Val Ala Val Ala Ala Ala
65                  70                  75                  80

Ser Ser Thr His Arg Lys Val Ala Ser Ser Thr Thr Gln Tyr Asp His
                85                  90                  95

Lys Glu Ser Cys Asn Gly Leu Tyr Tyr Gln Gly Ser Cys Tyr Ile Leu
            100                 105                 110

His Ser Asp Tyr Gln Leu Phe Ser Asp Ala Lys Ala Asn Cys Thr Ala
        115                 120                 125

Glu Ser Ser Thr Leu Pro Asn Lys Ser Asp Val Leu Ile Thr Trp Leu
    130                 135                 140

Ile Asp Tyr Val Glu Asp Thr Trp Gly Ser Asp Gly Asn Pro Ile Thr
145                 150                 155                 160

Lys Thr Thr Ser Asp Tyr Gln Asp Ser Asp Val Ser Gln Glu Val Arg
                165                 170                 175

Lys Tyr Phe Cys Val Lys Thr Met Asn
            180                 185

<210> SEQ ID NO 36
<211> LENGTH: 184
<212> TYPE: PRT
<213> ORGANISM: Variola virus
<220> FEATURE:
<221> NAME/KEY: MISC_FEATURE
<223> OTHER INFORMATION: Variola major A36R sequence (homologue of
``` vaccinia A33R)

<400> SEQUENCE: 36

Met Met Thr Pro Glu Asn Asp Glu Glu Gln Thr Ser Val Phe Ser Ala
1               5                   10                  15

Thr Val Tyr Gly Asp Lys Ile Gln Gly Lys Asn Lys Arg Lys Arg Val
            20                  25                  30

Ile Gly Ile Cys Ile Arg Ile Ser Met Val Ile Ser Leu Leu Ser Met
        35                  40                  45

Ile Thr Met Ser Ala Phe Leu Ile Val Arg Leu Asn Gln Cys Met Ser
    50                  55                  60

Ala Asn Glu Ala Ala Ile Thr Asp Ala Thr Ala Val Ala Ala Ala Leu
65                  70                  75                  80

Ser Thr His Arg Lys Val Ala Ser Ser Thr Gln Tyr Lys His Gln
                85                  90                  95

Glu Ser Cys Asn Gly Leu Tyr Tyr Gln Gly Ser Cys Tyr Ile Phe His
                100                 105                 110

Ser Asp Tyr Gln Leu Phe Ser Asp Ala Lys Ala Asn Cys Ala Thr Glu
            115                 120                 125

Ser Ser Thr Leu Pro Asn Lys Ser Asp Val Leu Thr Thr Trp Leu Ile
130                 135                 140

Asp Tyr Val Glu Asp Thr Trp Gly Ser Asp Gly Asn Pro Ile Thr Lys
145                 150                 155                 160

Thr Thr Thr Asp Tyr Gln Asp Ser Asp Val Ser Gln Glu Val Arg Lys
                165                 170                 175

Tyr Phe Cys Val Lys Thr Met Asn
            180

<210> SEQ ID NO 37
<211> LENGTH: 127
<212> TYPE: PRT
<213> ORGANISM: Variola virus
<220> FEATURE:
<221> NAME/KEY: MISC_FEATURE
<223> OTHER INFORMATION: Variola A36R sequence comparable to portion of
      Vaccinia A33R as can be expressed in baculovirus

<400> SEQUENCE: 37

Arg Leu Asn Gln Cys Met Ser Ala Asn Glu Ala Ala Ile Thr Asp Ala
1               5                   10                  15

Thr Ala Val Ala Ala Ala Leu Ser Thr His Arg Lys Val Ala Ser Ser
            20                  25                  30

Thr Thr Gln Tyr Lys His Gln Glu Ser Cys Asn Gly Leu Tyr Tyr Gln
        35                  40                  45

Gly Ser Cys Tyr Ile Phe His Ser Asp Tyr Gln Leu Phe Ser Asp Ala
    50                  55                  60

Lys Ala Asn Cys Ala Thr Glu Ser Ser Thr Leu Pro Asn Lys Ser Asp
65                  70                  75                  80

Val Leu Thr Thr Trp Leu Ile Asp Tyr Val Glu Asp Thr Trp Gly Ser
                85                  90                  95

Asp Gly Asn Pro Ile Thr Lys Thr Thr Thr Asp Tyr Gln Asp Ser Asp
                100                 105                 110

Val Ser Gln Glu Val Arg Lys Tyr Phe Cys Val Lys Thr Met Asn
            115                 120                 125

<210> SEQ ID NO 38
<211> LENGTH: 250

```
<212> TYPE: PRT
<213> ORGANISM: Vaccinia virus
<220> FEATURE:
<221> NAME/KEY: MISC_FEATURE
<223> OTHER INFORMATION: Vaccinia L1R (strain WR)

<400> SEQUENCE: 38

Met Gly Ala Ala Ala Ser Ile Gln Thr Thr Val Asn Thr Leu Ser Glu
1               5                   10                  15

Arg Ile Ser Ser Lys Leu Glu Gln Glu Ala Asn Ala Ser Ala Gln Thr
                20                  25                  30

Lys Cys Asp Ile Glu Ile Gly Asn Phe Tyr Ile Arg Gln Asn His Gly
            35                  40                  45

Cys Asn Leu Thr Val Lys Asn Met Cys Ser Ala Asp Ala Asp Ala Gln
50                  55                  60

Leu Asp Ala Val Leu Ser Ala Ala Thr Glu Thr Tyr Ser Gly Leu Thr
65                  70                  75                  80

Pro Glu Gln Lys Ala Tyr Val Pro Ala Met Phe Thr Ala Ala Leu Asn
                85                  90                  95

Ile Gln Thr Ser Val Asn Thr Val Val Arg Asp Phe Glu Asn Tyr Val
            100                 105                 110

Lys Gln Thr Cys Asn Ser Ser Ala Val Val Asp Asn Lys Leu Lys Ile
        115                 120                 125

Gln Asn Val Ile Ile Asp Glu Cys Tyr Gly Ala Pro Gly Ser Pro Thr
130                 135                 140

Asn Leu Glu Phe Ile Asn Thr Gly Ser Ser Lys Gly Asn Cys Ala Ile
145                 150                 155                 160

Lys Ala Leu Met Gln Leu Thr Thr Lys Ala Thr Thr Gln Ile Ala Pro
                165                 170                 175

Lys Gln Val Ala Gly Thr Gly Val Gln Phe Tyr Met Ile Val Ile Gly
            180                 185                 190

Val Ile Ile Leu Ala Ala Leu Phe Met Tyr Tyr Ala Lys Arg Met Leu
        195                 200                 205

Phe Thr Ser Thr Asn Asp Lys Ile Lys Leu Ile Leu Ala Asn Lys Glu
210                 215                 220

Asn Val His Trp Thr Thr Tyr Met Asp Thr Phe Phe Arg Thr Ser Pro
225                 230                 235                 240

Met Val Ile Ala Thr Thr Asp Met Gln Asn
                245                 250

<210> SEQ ID NO 39
<211> LENGTH: 250
<212> TYPE: PRT
<213> ORGANISM: Variola virus
<220> FEATURE:
<221> NAME/KEY: MISC_FEATURE
<223> OTHER INFORMATION: Variola major M1R sequence (homologue of
      vaccinia L1R)

<400> SEQUENCE: 39

Met Gly Ala Ala Ala Ser Ile Gln Thr Thr Val Asn Thr Leu Ser Glu
1               5                   10                  15

Arg Ile Ser Ser Lys Leu Glu Gln Glu Ala Asn Ala Ser Ala Gln Thr
                20                  25                  30

Lys Cys Asp Ile Glu Ile Gly Asn Phe Tyr Ile Arg Gln Asn His Gly
            35                  40                  45

Cys Asn Leu Thr Val Lys Asn Met Cys Ser Ala Asp Ala Asp Ala Gln
50                  55                  60
```

Leu Asp Ala Val Leu Ser Ala Ala Thr Glu Thr Tyr Ser Gly Leu Thr
65                  70                  75                  80

Pro Glu Gln Lys Ala Tyr Val Pro Ala Met Phe Thr Ala Ala Leu Asn
                85                  90                  95

Ile Gln Thr Ser Val Asn Thr Val Val Arg Asp Phe Glu Asn Tyr Val
            100                 105                 110

Lys Gln Thr Cys Asn Ser Ser Ala Val Val Asp Asn Lys Leu Lys Ile
        115                 120                 125

Gln Asn Val Ile Ile Asp Glu Cys Tyr Gly Ala Pro Gly Ser Pro Thr
130                 135                 140

Asn Leu Glu Phe Ile Asn Thr Gly Ser Ser Lys Gly Asn Cys Ala Ile
145                 150                 155                 160

Lys Ala Leu Met Gln Leu Thr Thr Lys Ala Thr Thr Gln Ile Ala Pro
                165                 170                 175

Arg Gln Val Ala Gly Thr Gly Val Gln Phe Tyr Met Ile Val Ile Gly
            180                 185                 190

Val Ile Ile Leu Ala Ala Leu Phe Met Tyr Tyr Ala Lys Arg Met Leu
        195                 200                 205

Phe Thr Ser Thr Asn Asp Lys Ile Lys Leu Ile Leu Ala Asn Lys Glu
210                 215                 220

Asn Val His Trp Thr Thr Tyr Met Asp Thr Phe Phe Arg Thr Ser Pro
225                 230                 235                 240

Met Val Ile Ala Thr Thr Asp Ile Gln Asn
                245                 250

<210> SEQ ID NO 40
<211> LENGTH: 185
<212> TYPE: PRT
<213> ORGANISM: Variola virus
<220> FEATURE:
<221> NAME/KEY: MISC_FEATURE
<223> OTHER INFORMATION: Variola  M1R sequence comparable to portion of
      L1R as can expressed in baculovirus

<400> SEQUENCE: 40

Met Gly Ala Ala Ala Ser Ile Gln Thr Thr Val Asn Thr Leu Ser Glu
1               5                   10                  15

Arg Ile Ser Ser Lys Leu Glu Gln Glu Ala Asn Ala Ser Ala Gln Thr
                20                  25                  30

Lys Cys Asp Ile Glu Ile Gly Asn Phe Tyr Ile Arg Gln Asn His Gly
            35                  40                  45

Cys Asn Leu Thr Val Lys Asn Met Cys Ser Ala Asp Ala Asp Ala Gln
        50                  55                  60

Leu Asp Ala Val Leu Ser Ala Ala Thr Glu Thr Tyr Ser Gly Leu Thr
65                  70                  75                  80

Pro Glu Gln Lys Ala Tyr Val Pro Ala Met Phe Thr Ala Ala Leu Asn
                85                  90                  95

Ile Gln Thr Ser Val Asn Thr Val Val Arg Asp Phe Glu Asn Tyr Val
            100                 105                 110

Lys Gln Thr Cys Asn Ser Ser Ala Val Val Asp Asn Lys Leu Lys Ile
        115                 120                 125

Gln Asn Val Ile Ile Asp Glu Cys Tyr Gly Ala Pro Gly Ser Pro Thr
130                 135                 140

Asn Leu Glu Phe Ile Asn Thr Gly Ser Ser Lys Gly Asn Cys Ala Ile
145                 150                 155                 160

```
Lys Ala Leu Met Gln Leu Thr Thr Lys Ala Thr Thr Gln Ile Ala Pro
                165                 170                 175

Arg Gln Val Ala Gly Thr Gly Val Gln
            180                 185

<210> SEQ ID NO 41
<211> LENGTH: 317
<212> TYPE: PRT
<213> ORGANISM: Vaccinia virus
<220> FEATURE:
<221> NAME/KEY: MISC_FEATURE
<223> OTHER INFORMATION: Vaccinia B5R (strain WR)

<400> SEQUENCE: 41

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Val Leu Pro Ile Cys Val Arg Thr
225                 230                 235                 240

Asn Glu Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Pro
305                 310                 315

<210> SEQ ID NO 42
```

<211> LENGTH: 317
<212> TYPE: PRT
<213> ORGANISM: Variola virus
<220> FEATURE:
<221> NAME/KEY: MISC_FEATURE
<223> OTHER INFORMATION: Variola major B6R sequence (homologue of vaccinia B5R)

<400> SEQUENCE: 42

```
Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Ser Gly Tyr Tyr Ser Leu Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Val Ser Glu Leu Tyr Asn Lys Pro Leu Tyr Glu Val Asn Ala Ile
                85                  90                  95

Ile Thr Leu Ile Cys Lys Asp Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Ser Leu Gln Leu Asp His Gly Ser Cys Gln Pro Val Lys
    130                 135                 140

Gly Lys Tyr Ser Phe Gly Glu His Ile Thr Ile Asn Cys Asp Val Gly
145                 150                 155                 160

Tyr Glu Val Ile Gly Ala Ser Tyr Ile Thr Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Ile Arg Ser
225                 230                 235                 240

Asn Glu Glu Phe Asp Pro Val Glu Asp Gly Pro Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asn
    290                 295                 300

Lys Asn Asn Asp Gln Tyr Lys Phe His Lys Leu Leu Leu
305                 310                 315
```

<210> SEQ ID NO 43
<211> LENGTH: 256
<212> TYPE: PRT
<213> ORGANISM: Variola virus
<220> FEATURE:
<221> NAME/KEY: MISC_FEATURE
<223> OTHER INFORMATION: Variola B6R sequence comparable to portion of B5R which can be expressed in baculovirus

```
<400> SEQUENCE: 43

Thr Cys Thr Val Pro Thr Met Asn Asn Ala Lys Leu Thr Ser Thr Glu
1               5                   10                  15

Thr Ser Phe Asn Asp Lys Gln Lys Val Thr Phe Thr Cys Asp Ser Gly
            20                  25                  30

Tyr Tyr Ser Leu Asp Pro Asn Ala Val Cys Glu Thr Asp Lys Trp Lys
            35                  40                  45

Tyr Glu Asn Pro Cys Lys Lys Met Cys Thr Val Ser Asp Tyr Val Ser
        50                  55                  60

Glu Leu Tyr Asn Lys Pro Leu Tyr Glu Val Asn Ala Ile Ile Thr Leu
65                  70                  75                  80

Ile Cys Lys Asp Glu Thr Lys Tyr Phe Arg Cys Glu Glu Lys Asn Gly
                85                  90                  95

Asn Thr Ser Trp Asn Asp Thr Val Thr Cys Pro Asn Ala Glu Cys Gln
            100                 105                 110

Ser Leu Gln Leu Asp His Gly Ser Cys Gln Pro Val Lys Gly Lys Tyr
            115                 120                 125

Ser Phe Gly Glu His Ile Thr Ile Asn Cys Asp Val Gly Tyr Glu Val
        130                 135                 140

Ile Gly Ala Ser Tyr Ile Thr Cys Thr Ala Asn Ser Trp Asn Val Ile
145                 150                 155                 160

Pro Ser Cys Gln Gln Lys Cys Asp Ile Pro Ser Leu Ser Asn Gly Leu
                165                 170                 175

Ile Ser Gly Ser Thr Phe Ser Ile Gly Gly Val Ile His Leu Ser Cys
            180                 185                 190

Lys Ser Gly Phe Ile Leu Thr Gly Ser Pro Ser Ser Thr Cys Ile Asp
            195                 200                 205

Gly Lys Trp Asn Pro Val Leu Pro Ile Cys Ile Arg Ser Asn Glu Glu
        210                 215                 220

Phe Asp Pro Val Glu Asp Gly Pro Asp Asp Glu Thr Asp Leu Ser Lys
225                 230                 235                 240

Leu Ser Lys Asp Val Val Gln Tyr Glu Gln Glu Ile Glu Ser Leu Glu
            245                 250                 255
```

COMPOSITIONS, METHODS AND KITS RELATING TO POXVIRUS SUBUNIT VACCINES

CROSS-REFERENCE TO RELATED APPLICATIONS

This application is a continuation of U.S. patent application Ser. No. 10/788,835, filed Feb. 27, 2004, now abandoned, which claims the benefit of priority pursuant to 35 U.S.C. § 119(c) to U.S. Provisional Patent Application No. 60/451,337, filed on Feb. 28, 2003, all of which are incorporated by reference in their entirety herein.

STATEMENT REGARDING FEDERALLY SPONSORED RESEARCH OR DEVELOPMENT

This research was supported, in part, by U.S. Government funds (National Institutes of Health Grant Nos. R21-AI53404 and U54-AI57168), and the U.S. Government may therefore have certain rights in the invention.

BACKGROUND OF THE INVENTION

Worldwide eradication of smallpox (a disease resulting from infection with *variola* virus) by vaccination with *vaccinia* virus (VV) was an outstanding success. Vaccination was discontinued in the U.S. in 1972 and therefore the entire population must be considered susceptible to smallpox. In response to a smallpox attack by bioterrorists, live VV vaccination is the only licensed prophylaxis (Breman et al., 1998, N. Eng. J. Med. 339:556-559; Franz et al., 1997, JAMA 278:399-411, Henderson, 1999, Science. 283:1279-82; Henderson et al., 2001, Clin. Infect. Dis. 33:1057-1059). However, mass immunization is limited by the fact that the live-virus vaccine has complications, especially in immunocompromised hosts, pregnant women and infants. An attenuated form of the vaccine, called MVA (modified VV Ankara), is an option for immunizing such at risk populations (Meyer et al., 1991, J. Gen. Virol. 72: 1031-1038; Moss, 1996, Proc. Natl. Acad. Sci. U.S.A. 93:11341-1134). However, this virus has not been tested to determine whether it can prevent smallpox and production of the virus in chicken embryo cells can be problematic.

Viruses in the Poxyiridae family, including VV and *variola* virus, are characterized by a large linear double-stranded DNA genome (130-300 kb) packaged in a relatively large particle, and a cytoplasmic site of replication (reviewed by Moss, 1996, In: Fields Virology, Knipe et al. eds., vol. 3, pp. 2637-2671, Lippincott-Raven, Philadelphia). Two distinct types of infectious particles are produced during poxvirus replication: the intracellular mature virions (IMV) and the extracellular enveloped virions (EEV) (Smith et al., 1998, Adv. Exp. Med. Biol. 440:395-414; Sodeik et al., 2002, Trends Microbiol. 10:15-24). A third form, CEV (cell-associated enveloped virus) is very similar in composition to EEV but remains tightly associated with the membrane of the cell it exited from.

IMV is the most abundant form of infectious particle and is surrounded by a lipid bilayer studded with membrane proteins, including L1R, A27L, A17L, D8L and H3L. EEVs consist of IMVs wrapped by a double membrane acquired from the Golgi apparatus (Hiller et al., 1985, J. Virol. 55:651-659; Moss, 1996, Proc. Natl. Acad. Sci. U.S.A. 93:1131-1134). The EEV membrane is studded with EEV-specific proteins, for example A33R and B5R. Released EEVs are responsible for widespread dissemination of VV in vivo and form the distinct comet-shaped plaques of VV seen in vitro (Boulter, 1969, Proc. R. Soc. Med. 62:295-7; Boulter et al., 1973, Prog. Med. Virol. 16:86-108; Law et al., 2002, J. Gen. Virol. 83:209-222; Payne, 1979, J. Virol. 31:147-155; Payne, 1980, J. Gen. Virol. 50:89-100).

IMV and EEV are equally infectious in vitro. The consensus is that IMVs enter cells via direct fusion with the plasma membrane. The entry of EEV is controversial. In one study, both EEV and IMV entered at neutral pH, and entry of both forms was insensitive to lysosomatropic agents, implying direct fusion (Doms et al., 1990, J. Virol. 64:4884-4892). Recent evidence indicates that cytochalasin D, an actin-depolymerizing drug, affected the entry of both forms and that entry of EEV, but not IMV, was inhibited by chloroquine and ammonium chloride (Ichihashi et al., 1996, Virology. 217: 478-485; Vanderplasschen et al., 1998, J. Gen. Virol. 79:877-887). This suggests that EEVs gain entry to cells via an endocytic pathway. These differences in entry may reflect differences in receptor usage by as yet unidentified virion proteins that are unique to each form.

IMV is thought to be responsible for VV spread between hosts because the membrane of EEV is fragile (Ichihashi et al., 1996, Virology. 217:478-485). EEV is postulated to be responsible for widespread dissemination of virus within the host (Boulter et al., 1969, Proc. R. Soc. Med. 62:295-7; Boulter et al., 1973, Prog. Med. Virol. 16:86-108; Payne et al., 1980, J. Gen. Virol. 50:89-100). In support of this, a correlation was found between the virulence of VV strains and their ability to form EEV in vitro (Payne et al., 1980, J. Gen. Virol. 50:89-100). Earlier studies showed that immunity to EEV conferred protection against poxvirus infections (Appleyard et al., 1974, J. Gen. Virol. 23:197-200; Appleyard et al., 1971, J. Gen. Virol. 13:9-17; Boulter et al., 1973, Prog. Med. Virol. 16:86-108; Payne et al., 1980, J. Gen. Virol. 50:89-100; Turner et al., 1971, J. Gen. Virol. 13:19-25). In support of this, two EEV proteins, A33R and B5R (Galmiche et al., 1999, Virology 254:71-80), or DNA encoding them (Hooper et al., 2000, Virology 266:329-339) protected mice from VV challenge. However, IMV proteins are also likely to play an important role in protection. For example, vaccination with the DNA encoding the full-length IMV protein L1R protected mice from VV challenge (Hooper et al., 2000, Virology. 266: 329-39).

In the event of bioterrorism using smallpox, the only commercially approved smallpox vaccine available in the U.S. is Wyeth Dryvax, which consists of lyophilized VV prepared from calves. This vaccine caused adverse events in vaccinees (Kempe, 1960, 26:176-189; Lane et al. JAMA 212:441-4; Lane et al., 1969, New Eng. J. Med. 281:1201-1208; Lane et al., 1970, J. Infect. Dis. 122:303-952-54), ranging from mild local reactions to serious sequelae, such as postvaccinal encephalopathy, encephalitis and death. The vaccine is contraindicated in immunosuppressed patients, pregnant women, and infants. In a 1968 surveillance study of people receiving the vaccine for the first time, there were approximately 75 complications per million vaccinations with an overall death rate of one per million (Lane et al., 1969, New Eng. J. Med. 281:1201-1208). However, since complications from smallpox vaccination were not reportable, these numbers underestimate the actual rates.

The only approved treatment available in the U.S. for vaccine related complications is *vaccinia* immune globulin (VIG), administered intramuscularly at about 0.6 ml/kg as described in Rosenthal et al. (2001, Emerg. Infect. Dis. 7:920-926). VIG was obtained from persons who were immunized with Dryvax. VIG is effective in reducing morbidity and mortality from vaccine related complications, although it has to be given in large amounts and is currently in short supply. Obtaining more of this material requires VV vaccination of people, and that poses the very same risks to the vaccinees who are used as a source of new VIG. Therefore, alternative treatments of complications from VV vaccination are needed in the event that a smallpox outbreak occurs.

In sum, there is a long-felt need to develop a smallpox vaccine that offers advantages over *vaccinia* virus live vaccines, which have numerous serious drawbacks, and to develop methods of providing protective immunity to this devastating human pathogen. The present invention meets these needs. Further, the present invention provides novel immune reagents that can be developed into a defined and potent form of VIG (called VIG-R).

BRIEF SUMMARY OF THE INVENTION

The invention includes a vaccine comprising a soluble truncated mammalian poxvirus envelope protein and a pharmaceutically acceptable carrier, wherein the protein is at least one protein selected from the group consisting of A33Rt, B5Rt, and L1R(185t), or a homologue thereof.

In one aspect, the poxvirus is at least one poxvirus selected from the group consisting of *vaccinia* virus and *variola* virus.

In another aspect, the vaccine further comprises at least one protein selected from the group consisting of A17L, A27L, A34R, A56R, D8L, F9L, F13L, and H3L, or a homologue thereof.

In a further aspect, the A33Rt comprises from about amino acid residue number 58 to 185 relative to full-length A33R (SEQ ID NO:35).

In yet another aspect, the amino acid sequence of the A33Rt is the sequence of SEQ ID NO:3

In another aspect, the B5Rt comprises from about amino acid residue number 20 to 275 relative to full-length B5R (SEQ ID NO:41).

In yet another aspect, the amino acid sequence of the B5Rt is the sequence of SEQ ID NO:5.

In a further aspect, the L1R(185t) comprises from about amino acid residue number 1 to 185 relative to full-length L1R (SEQ ID NO:38).

In yet a further aspect, the amino acid sequence of the L1R(185t) is the sequence of SEQ ID NO:1.

In another aspect, the vaccine comprises A33Rt and L1R (185t).

In yet another aspect, the vaccine further comprises B5Rt.

In a further aspect, the A17L is A17Lt and comprises from about amino acid residue number 80 to 138 relative to full-length A17L.

In another aspect, the vaccine further comprises at least one *variola* virus homologue protein selected from the group consisting of A36R, B6R, and M1R.

The invention includes a vaccine comprising an isolated nucleic acid encoding a soluble truncated mammalian poxvirus envelope protein and a pharmaceutically acceptable carrier, wherein the protein is at least one protein selected from the group consisting of A33Rt, B5Rt, and L1Rt(185), or a homologue thereof.

In one aspect, the protein is at least one *vaccinia* virus protein selected from the group consisting of A17L, A27L, A34R, A56R, D8L, F9L, F13L, and H3L.

In another aspect, the nucleotide sequence of the nucleic acid is at least one sequence selected from the group consisting of the sequence of SEQ ID NO:1 encoding L1R(185t), sequence of SEQ ID NO:3 encoding A33Rt, and sequence of SEQ ID NO:5 encoding B5Rt.

The invention includes an isolated poxvirus neutralizing antibody which specifically binds to a soluble truncated mammalian poxvirus envelope protein.

In one aspect, the antibody is selected from the group consisting of a polyclonal antibody, a monoclonal antibody, and a synthetic antibody.

In another aspect, the antibody is a monoclonal antibody that specifically binds to B5R and further wherein the antibody is selected from the group consisting of VMC-7, VMC-8, VMC-9, VMC-10, VMC-11, VMC-12, VMC-13, VMC-14, VMC-15, VMC-16, VMC-18, VMC-19, VMC-20, VMC-21, VMC-22, VMC-23, VMC-24, VMC-25, VMC-26, VMC-27, VMC-28, VMC-29, VMC-30, VMC-31, VMC-32, and VMC-33.

In a further aspect, the antibody is a monoclonal antibody that specifically binds to L1R(185t) wherein the antibody is VMC-2.

In yet a further aspect, the antibody is a monoclonal antibody that specifically binds to A33Rt wherein the antibody is VMC-1.

In yet another aspect, the protein is selected from the group consisting of A33Rt, B5Rt and L1R(185t).

The invention includes an isolated nucleic acid encoding an isolated poxvirus neutralizing antibody which specifically binds to a soluble truncated mammalian poxvirus envelope protein.

The invention includes a method of immunizing a human patient against a poxvirus infection comprising administering to the patient an immunogenic amount of a vaccine comprising a soluble truncated mammalian poxvirus envelope protein and a pharmaceutically acceptable carrier, wherein the protein is at least one protein selected from the group consisting of A33Rt, B5Rt, and L1R(185t), or a homologue thereof.

The invention includes a method of immunizing a human patient against a poxvirus infection comprising administering to the patient an effective amount of a vaccine comprising a soluble truncated mammalian poxvirus envelope protein and a pharmaceutically acceptable carrier, wherein the protein is at least one protein selected from the group consisting of A33Rt, B5Rt, and L1R(185t), or a homologue thereof, where the vaccine further comprises at least one protein selected from the group consisting of A17L, A27L, A34R, A56R, D8L, F9L, F13L, and H3L, or a homologue thereof.

The invention includes a method of immunizing a human patient against a poxvirus infection comprising administering to the patient an effective amount of an isolated nucleic acid encoding an isolated poxvirus neutralizing antibody which specifically binds to a soluble truncated mammalian poxvirus envelope protein.

The invention includes a method of immunizing a human patient against a poxvirus infection comprising administering to the patient an effective amount of a vaccine comprising an isolated nucleic acid encoding a soluble truncated mammalian poxvirus envelope protein and a pharmaceutically acceptable carrier, wherein the protein is at least one protein selected from the group consisting of A33Rt, B5Rt, and L1Rt (185), or a homologue thereof.

The invention includes a method of immunizing a human patient against a poxvirus infection comprising administering to the patient an effective amount of an isolated poxvirus neutralizing antibody which specifically binds to a soluble truncated mammalian poxvirus envelope protein.

The invention also includes a method of treating a poxvirus infection in a human patient comprising administering to the patient an effective amount of a vaccine comprising a soluble truncated mammalian poxvirus envelope protein and a pharmaceutically acceptable carrier, wherein the protein is at least one protein selected from the group consisting of A33Rt, B5Rt, and L1R(185t), or a homologue thereof.

The invention includes a method of treating a poxvirus infection in a human patient comprising administering to the patient an effective amount of a vaccine comprising an isolated nucleic acid encoding a soluble truncated mammalian poxvirus envelope protein and a pharmaceutically acceptable carrier, wherein the protein is at least one protein selected from the group consisting of A33Rt, B5Rt, and L1Rt(185), or a homologue thereof.

The invention includes a method of treating a poxvirus infection in a human patient comprising administering to the patient an effective amount of an isolated poxvirus neutralizing antibody which specifically binds to a soluble truncated mammalian poxvirus envelope protein.

The invention further includes a method of treating a poxvirus infection in a human patient comprising administering to the patient an effective amount of an isolated nucleic acid encoding an isolated poxvirus neutralizing antibody which specifically binds to a soluble truncated mammalian poxvirus envelope protein.

The invention includes a method of treating a poxvirus infection in a human patient comprising administering to the patient an effective amount of an isolated poxvirus neutralizing antibody which specifically binds to a soluble truncated mammalian poxvirus envelope protein in a pharmaceutically acceptable carrier.

The invention also includes a method of treating a poxvirus infection in a human patient comprising administering to the patient an effective amount of an isolated nucleic acid encoding an isolated poxvirus neutralizing antibody which specifically binds to a soluble truncated mammalian poxvirus envelope protein, in a pharmaceutically acceptable carrier.

The invention includes a composition comprising at least one soluble truncated mammalian poxvirus envelope protein.

In one aspect, the poxvirus is at least one poxvirus selected from *vaccinia* virus and *variola* virus.

In another aspect, the protein is at least one *vaccinia* protein selected from the group consisting of A33Rt, B5Rt, L1R (185t), or a homologue thereof.

In yet another aspect, the homologue is at least one *variola* protein selected from the group consisting of A36R, B6R, and M1R.

In a further aspect, the amino acid sequence of the A33Rt is the sequence of SEQ ID NO:3.

In yet a further aspect, the composition further comprises a *vaccinia* L1R(185t) wherein the amino acid sequence of the L1R(185t) is the sequence of SEQ ID NO:1.

In yet another aspect, the composition further comprises a *vaccinia* B5Rt protein wherein the amino acid sequence of the B5Rt is the sequence of SEQ ID NO:5.

In yet a further aspect, the composition further comprises a pharmaceutically acceptable carrier.

The invention includes an isolated nucleic acid encoding a *vaccinia* virus soluble truncated envelope protein.

In one aspect, the protein is selected from the group consisting of A33Rt, B5Rt, and L1R(185t).

In yet another aspect, the sequence of the nucleic acid encoding A33Rt is SEQ ID NO:4, the sequence of the nucleic acid encoding B5Rt is SEQ ID NO:6, and further wherein the sequence of the nucleic acid encoding L1R(185t) is SEQ ID NO:2.

The invention includes a protein encoded by an isolated nucleic acid encoding a *vaccinia* virus soluble truncated envelope protein, where the sequence of the nucleic acid encoding A33Rt is SEQ ID NO:4, the sequence of the nucleic acid encoding B5Rt is SEQ ID NO:6, and further wherein the sequence of the nucleic acid encoding L1R(185t) is SEQ ID NO:2.

The invention includes a protein encoded by an isolated nucleic acid encoding a *vaccinia* virus soluble truncated envelope protein.

The invention includes an isolated mammalian poxvirus soluble truncated envelope protein.

In one aspect, the poxvirus is *vaccinia* and further wherein the protein is selected from the group consisting of A33Rt, B5Rt, and L1R(185t).

In another aspect, the amino acid sequence of the A33Rt is the sequence of SEQ ID NO:3, the amino acid sequence of the B5Rt is the sequence of SEQ ID NO:5, and the amino acid sequence of the L1R(185t) is the sequence of SEQ ID NO:1.

The invention includes a kit for immunizing a human patient against a poxvirus infection, the kit comprises an immunogenic amount of the soluble truncated poxvirus envelope protein encoded by an isolated nucleic acid encoding a *vaccinia* virus soluble truncated envelope protein. The kit further comprises an applicator and an instructional material for the use of the kit.

The invention includes a kit for immunizing a human patient against a poxvirus infection, the kit comprises an immunogenic amount of the soluble truncated poxvirus envelope protein encoded by an isolated nucleic acid encoding a *vaccinia* virus soluble truncated envelope protein. The kit further comprises an applicator and an instructional material for the use of the kit.

The invention includes a kit for immunizing a human patient against a poxvirus infection. The kit comprises an effective amount of an isolated poxvirus neutralizing antibody which specifically binds to a soluble truncated mammalian poxvirus envelope protein. The kit further comprises an applicator and an instructional material for the use of the kit.

The invention includes a kit for treating a poxvirus infection in a human patient, the kit comprising an immunogenic amount of an isolated mammalian poxvirus soluble truncated envelope protein. The kit further comprises an applicator and an instructional material for the use of the kit.

The invention also includes a kit for treating a poxvirus infection in a human patient, the kit comprising an immunogenic amount of an isolated nucleic acid encoding a *vaccinia* virus soluble truncated envelope protein. The kit further comprises an applicator and an instructional material for the use of the kit.

The invention includes a kit for treating a poxvirus infection in a human patient, the kit comprising an effective amount of an isolated poxvirus neutralizing antibody which specifically binds to a soluble truncated mammalian poxvirus envelope protein, the kit further comprising an applicator and an instructional material for the use of the kit.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

Figure 1:
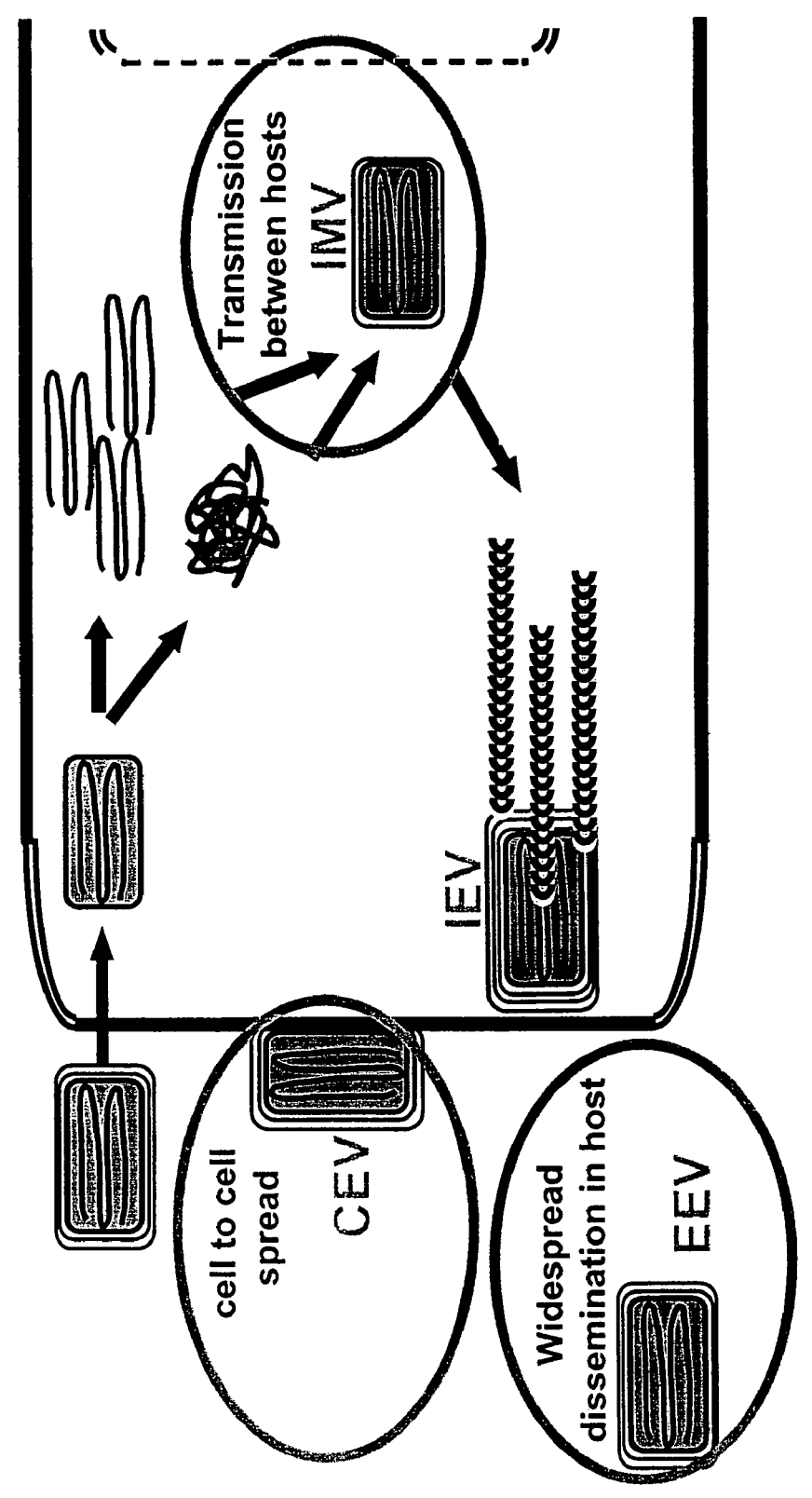

FIG. 1 is a diagram illustrating, without wishing to be bound by any particular theory, a model for *vaccinia* life cycle. *Vaccinia* virus can enter the cell either by endocytosis or by membrane fusion in a low pH-independent manner. The DNA can then be released from the core and can either replicate or be transcribed into RNA, which is then translated into proteins. In this way, IMV particles are formed (for Intracellular Mature Virion). These IMVs can then acquire a double set of membranes, becoming an IEV (for Intracellular Enveloped Virion). By associating with microtubules, the IEV reach the periphery of the cell. The virions are either released to the extracellular medium, becoming EEV (Extracellular Enveloped Virion) or remain attached to the outer surface of the cell, becoming CEV (for Cell associated Enveloped Virion). The IMV can be released by cell lysis and is responsible for transmission between hosts. The CEV mediates cell to cell spread and the EEV is responsible for widespread dissemination in the host.

FIG. 3 also depicts possible topologies (A or B) of L1R. Most of the L1R protein is exposed on the virion surface (similar to A). FIG. 3 also illustrates a schematic representation of the baculovirus constructs of A33Rt and L1R(185t), and Western blot and Silver stain of the purified A33Rt and L1R(185t) recombinant proteins.

FIGS. 5A and 5B, illustrates the expression of A33Rt in baculovirus (Bac-A33Rt) infected Sf9 cells. The ectodomain of A33R (stick figure corresponding to amino acid 58-185) was cloned into baculovirus with a 6-Histidine tag at the C-terminus and the expressed protein was purified from the culture supernatant by nickel chromatography. FIG. 5A illustrates the purified protein following electrophoreses under reducing conditions and stained with silver. FIG. 5B illustrates the purified protein following electrophoreses under reducing (+βme) or non-reducing (−βme) conditions and western blotted using anti-His monoclonal antibody.

FIG. 6 also illustrates the baculovirus constructs.

FIG. 7, comprising FIG. 7A depicts A33Rt, FIG. 7B depicts B5Rt and FIG. 7C depicts L1R(185t).

FIG. 8, comprising FIG. 8A-8C are images demonstrating the ability of the polyclonal antibodies (anti A33Rt, anti-L1R (185t) and anti-B5Rt) to react with the bona fide *vaccinia* virus proteins.

FIG. 9, comprising FIGS. 9A and 9B, demonstrates polyclonal antibodies recognizing A33Rt, L1R(185t) and B5Rt are able to neutralize *vaccinia* virus in a plaque reduction assay. FIG. 9A is a diagram depicting a strategy for a plaque reduction assay. Briefly, the assay involves infecting a monolayer of cells with a preparation of virus in combination with an antibody and then counting the plaques. FIG. 9B is a graph depicting the results from the plaque reduction assay. As a negative control, the virus was incubated with IgGs obtained from rabbit pre-immune sera.

FIG. 10, comprising FIGS. 10A and 10B, demonstrates an antibody recognizing B5Rt was able to neutralize EEV. FIG. 10A is a diagram depicting the strategy for a plaque reduction assay. FIG. 10B is a graph demonstrating the results from the plaque reduction assay.

FIG. 11, comprising FIG. 11A is an ELISA strategy used to test the binding of VIG to recombinant *vaccinia* proteins and FIG. 11B is a graph demonstrating results from the ELISA.

FIG. 13, comprising FIGS. 13A and 13B, demonstrates that VIG pretreated with soluble L1R(185t) does not inhibit VIG from neutralizing *vaccinia* virus.

FIG. 14, comprising FIGS. 14A and 14B, demonstrate that pre-incubated of L1R(185t) with VIG eliminates L1R(185t)-reactive antibodies from VIG.

FIG. 15, comprising FIGS. 15A and 15B, demonstrates the pre-incubation of VMC-2 with L1R(185t) eliminates the *vaccinia* virus neutralizing activity of VMC-2. VMC-2 is a mouse monoclonal antibody directed to L1R and was produced according to the methods disclosed elsewhere herein by immunizing mice with L1R(185t) of the invention. This monoclonal recognizes a linear epitope and also recognizes L1R produced in VV infected cells. Further, VMC-2 can neutralize the infectivity of IMV.

FIG. 17, comprising FIG. 17A is a graph illustrating the effect of anti-B5R rabbit polyclonal on a plaque reduction assay. FIG. 17B is an image illustrating the effect of anti-B5R on a comet tail formation assay.

FIG. 21 summarizes the results from the plaque reduction assay and the comet tail inhibition assay. 7 out of 26 monoclonals directed against B5R were observed to be able to reduce the plaque number of EEV, but only two out of those 7 was observed to be able to inhibit tail formation.

FIG. 22 depicts the twenty-eight (28) overlapping peptides prepared spanning the ectodomain of B5R. The amino acid sequence for each peptide and the range, expressed as amino acid residue number corresponding to the open reading frame of full-length WR B5R (GenBank Accession No. Q01227), is set forth.

FIG. 25 is a table summarizing results from a binding competition assay were performed with all available antibodies. The antibodies that were injected first are indicated along the top of the table, and the vertical rows indicate the antibodies that were injected after the first MAb. The results are expressed in terms of percentage of binding of the second antibody

FIG. 31 is a graph demonstrating that passive immunization using monoclonal antibodies directed to A33Rt (VMC-1), L1R(185t) (VMC-2) and/or B5Rt (VMC-25) protects mice against a lethal intranasal infection with pathogenic vaccinia virus. Mice receiving a combination of all three MAbs to A33Rt, L1R(185t) and B5Rt (VMC-1, VMC-2 and VMC-25) lost less weight than those receiving any MAb separately and was as effective as immunization with VV. These data demonstrate that the combination of an antibody to the EEV and an antibody to the IMV is preferable, and the combination of MAb to all three proteins is even more preferable.

FIG. 33A depicts the amino acid sequence of Baculovirus L1R(185t) (SEQ ID NO:1).

FIG. 33B depicts the nucleic acid sequence of Baculovirus L1R(185t) (SEQ ID NO:2).

FIG. 33C sets out L1R amino acid residues 1-185 (SEQ ID NO: 1) expressed in baculovirus with DPA residues added to the N-terminus of the recombinant protein and 6-His tag (HHHHHH) (SEQ ID NO: 44) added to the C-terminus of the recombinant protein.

FIG. 33D sets out the nucleic acid sequence (SEQ ID NO: 2) of L1 R residues 1-185 expressed in baculovirus with DPA residues added to the N-terminus of the recombinant protein and 6-His tag (HHHHHH) (SEQ ID NO: 44) added to the C-terminus of the recombinant protein.

FIG. 34A depicts the amino acid sequence of Baculovirus A33Rt (SEQ ID NO:3).

FIG. 34B depicts the nucleic acid sequence of Baculovirus A33Rt (SEQ ID NO:4).

FIG. 34C sets out a recombinant protein sequence expressed in baculovirus corresponding to SEQ ID NO. 45, wherein DP residues are added to the N-terminus of A33R residues 58-185 and a 6-His tag (HHHHHH) (SEQ ID NO: 44) is added to the C-terminus of the recombinant protein.

FIG. 34D sets out an isolated nucleic acid sequence corresponding to SEQ ID NO. 46 that encodes a recombinant protein comprising DP residues added to the N-terminus of A33R residues 58-185 and a 6-His tag (HHHHHH) (SEQ ID NO: 44) added to the C-terminus of the recombinant protein. The 6-His tag is encoded by the underlined CATCATCAC-CATCACCAT nucleic acids (SEQ ID NO: 49) depicted at the 3' end of the entire nucleotide sequence.

FIG. 35A depicts the amino acid sequence of Baculovirus B5Rt (SEQ ID NO:5).

FIG. 35B depicts the nucleic acid sequence of Baculovirus B5Rt (SEQ ID NO:6).

FIG. 35C sets out a recombinant protein sequence expressed in a baculovirus corresponding to SEQ ID NO: 47,wherein DLHHHHHH (SEQ ID NO: 50) (underlined) residues are added to the N-terminus of B5R residues 20-275.

FIG. 35D sets out the nucleic acid sequence corresponding to SEQ ID NO: 48 that encodes the protein sequence depicted in FIG. 35C. The underlined nucleic acid sequence GATCT-GCATCATCACCATCATCAC (SEQ ID NO: 51) at the 5' end of the nucleic acid encodes the DLHHHHHH (SEQ ID NO: 50) residues added to the N-terminus of B5R residues 20-275 expressed in baculovirus.

FIG. 36A depicts the amino acid sequence of *Vaccinia* A33R (strain WR) (SEQ ID NO:35).

FIG. 36B depicts the amino acid sequence of *Variola* major A36R (homologue of *vaccinia* A33R) (SEQ ID NO:36).

FIG. 36C sets out a comparison of *Vaccinia* A33R (top sequence; SEQ ID NO. 35) 185 amino acids with *Variola* A36R (bottom sequence; SEQ ID NO. 36) 184 amino acids demonstrating about 94.1% identity.

FIG. 36D depicts the amino acid sequence of *Variola* A36 sequence (SEQ ID NO. 37) comparable to portion of *Vaccinia* A33R as can be expressed in baculovirus.

FIG. 36E sets out a comparison of *Vaccinia* A33Rt (top sequence; SEQ ID NO. 3) 128 amino acids with *Variola* "A36Rt" (bottom sequence; SEQ ID NO. 37) 127 amino acids demonstrating about 92.2% identity.

FIG. 37A depicts the amino acid sequence of *Vaccinia* L1R (strain WR) (SEQ ID NO:38).

FIG. 37B depicts the amino acid sequence of *Variola* major M1R (homologue of *vaccinia* L1R) (SEQ ID NO:39).

FIG. 37C sets out a comparison of *Vaccinia* L1R (top sequence; SEQ ID NO. 38) 250 amino acids with M1R (bottom sequence; SEQ ID NO. 39) 250 amino acids demonstrating about 99.2% identity.

FIG. 37D depicts the amino acid sequence of *Variola* M1R (SEQ ID NO:40) comparable to portion of L1R as can expressed in baculovirus.

FIG. 37E sets out a comparison of *Vaccinia* A33Rt (top sequence; SEQ ID NO. 3) 128 amino acids with *Variola* "A36Rt" (bottom sequence; SEQ ID NO. 37) 127 amino acids demonstrating about 92.2% identity.

FIG. 38A depicts the amino acid sequence of *vaccinia* B5R (strain WR) (SEQ ID NO:41).

FIG. 38B depicts the amino acid sequence of *Variola* major B6R (homologue of *vaccinia* B5R) (SEQ ID NO:42).

FIG. 38C sets out a comparison of *Vaccinia* B5R (top sequence; SEQ ID NO. 41) 317 amino acids with *Variola* B6R (bottom sequence; SEQ ID NO. 42) 317 amino acids, demonstrating 92.7% identity.

FIG. 38D depicts the amino acid sequence of *Variola* B6R sequence (SEQ ID NO:43) comparable to portion of B5R which can be expressed in baculovirus.

FIG. 38E sets out a comparison of *Vaccinia* B5Rt (top sequence; SEQ ID NO. 5) 256 amino acids with *Variola* "B6Rt" (bottom sequence; SEQ ID NO. 43) 256 amino acids, demonstrating 91.8% identity.

DETAILED DESCRIPTION OF THE INVENTION

Figure 2:
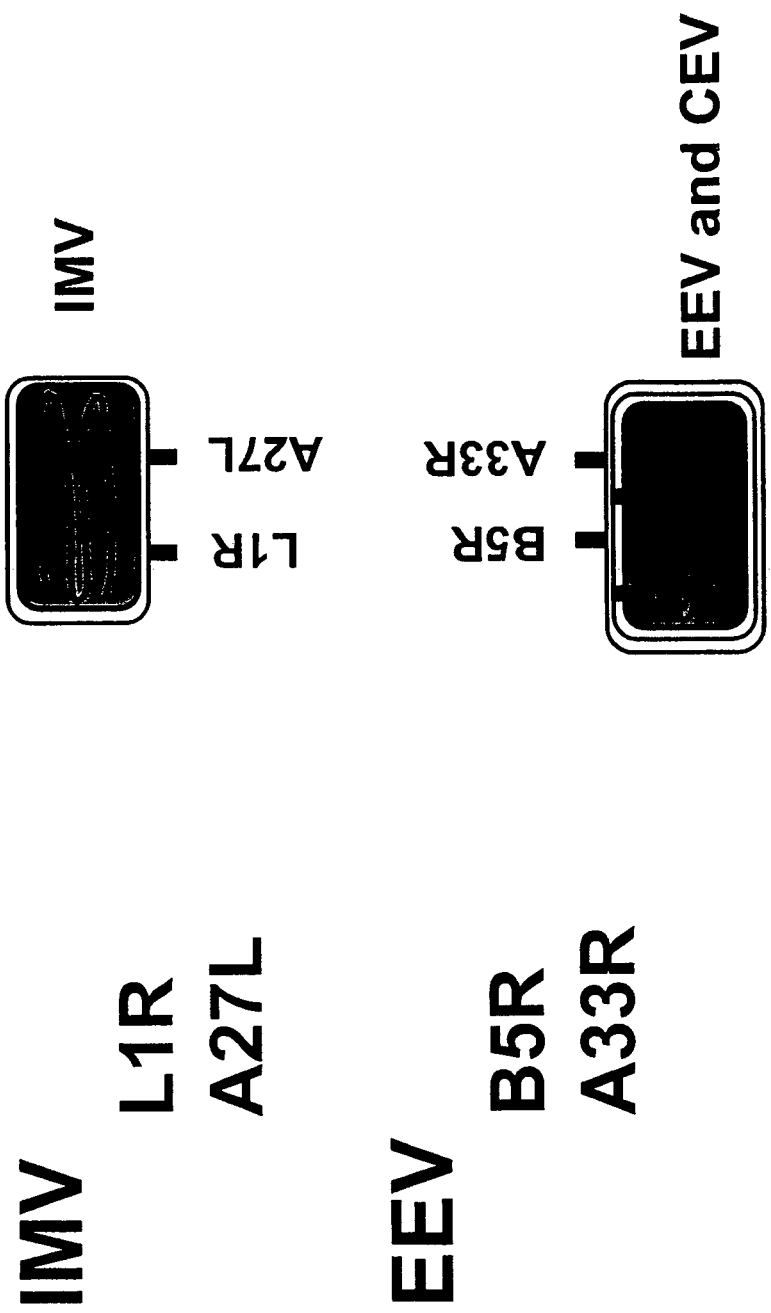
FIG. 2 is a diagram illustrating, without wishing to be bound by any particular theory, various glycoproteins present on the surface of a *vaccinia* virion. Amongst others, the IMV has the proteins L1R and A27L. The CEV and the EEV have the proteins B5R and A33R, amongst others.

The invention relates to the discovery that soluble truncated mammalian poxvirus envelope proteins, either alone or in combination, can protect an animal against infection by the poxvirus. Thus, there has been discovered a subunit vaccine comprising at least one soluble truncated mammalian poxvirus envelope protein, which vaccine is useful not only as a prophylactic therapeutic agent for initial protection of an animal against a poxvirus infection, but is also useful as a therapeutic agent for treatment of an ongoing poxvirus infection in an animal.

Additionally, the invention relates to the discovery that passive immunization with an antibody that specifically binds with such proteins can also protect an animal from poxvirus infection, as well as treat an ongoing infection. Further, the invention also relates to use of an antibody that specifically binds with a protein of the invention wherein the antibody can be administered to passively immunize an animal thereby preventing and/or treating a poxvirus infection and also to treat a complication mediated by immunization of an individual with a live virus vaccine.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a disease means reducing the severity of one or more symptoms of the disease.

As used herein, "amino acids" are represented by the full name thereof, by the three-letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator," as the term is used herein, is meant any device including, but not limited to, a hypodermic syringe, a pipette, and the like, for administering the compounds and compositions of the invention.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount", as used herein, is meant an amount that when administered to a mammal, causes a detectable level of immune response compared to the immune response detected in the absence of the compound. Immune response can be readily assessed by a plethora of art-recognized methods.

The skilled artisan would understand that the amount of the compound or composition administered herein varies and can be readily determined based on a number of factors such as the disease or condition being treated, the age and health and physical condition of the mammal being treated, the severity of the disease, the particular compound being administered, and the like.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

By "complementary to a portion or all of the nucleic acid encoding" a protein of the invention, is meant a sequence of nucleic acid which does not encode a poxvirus soluble truncated protein. Rather, the sequence which is being expressed in the cells is identical to the non-coding strand of the nucleic acid encoding the protein and thus, does not encode the protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 18 nucleotides in length, preferably, at least about 24 nucleotides, more typically, from about 24 to about 50 nucleotides, preferably, at least about 50 to about 100 nucleotides, even more preferably, at least about 100 nucleotides to about 200 nucleotides, yet even more preferably, at least about 200 to about 300, even more preferably, at least about 300 nucleotides to about 400 nucleotides, yet even more preferably, at least about 400 to about 500, and most preferably, the nucleic acid fragment will be greater than about 500 nucleotides in length.

As applied to a protein, a "fragment" of a poxvirus protein is about 6 amino acids in length. More preferably, the fragment of a poxvirus protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length.

A "genomic DNA" is a DNA strand which has a nucleotide sequence homologous with a gene as it exists in the natural host. By way of example, a fragment of a chromosome is a genomic DNA.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web government site of the National Library of Medicine as part of the National Institutes of Health. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See publicly available government web site of National Center for Biotechnology Information (NCBI) of the National Library of Medicine at the National Institutes of Health.

The percent identity between two sequences can be determined using techniques similar to those described above, with or without allowing gaps. In calculating percent identity, typically exact matches are counted.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding a chromogenic substrate such as o-nitrophenyl-β-galactoside to the medium (Gerhardt et al., eds., 1994, Methods for General and Molecular Bacteriology, American Society for Microbiology, Washington, D.C., p. 574).

A "restriction site" is a portion of a double-stranded nucleic acid which is recognized by a restriction endonuclease.

A first oligonucleotide anneals with a second oligonucleotide "with high stringency" if the two oligonucleotides anneal under conditions whereby only oligonucleotides which are at least about 73%, more preferably, at least about 75%, even more preferably, at least about 80%, even more preferably, at least about 85%, yet more preferably, at least about 90%, and most preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, the term "transgenic mammal" means a mammal, the germ cells of which comprise an exogenous nucleic acid.

As used herein, to "treat" means reducing the frequency with which symptoms of a disease (i.e., poxvirus infection, sequelae following immunization, and the like) are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a nucleic acid that encodes a protein and/or antibody of the invention, to the patient, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

A "therapeutic" treatment is a treatment administered to a patient who exhibits signs of pathology for the purpose of diminishing or eliminating those signs and/or decreasing or diminishing the frequency, duration and intensity of the signs.

An "effective amount" of a compound is that amount of compound which is sufficient to provide a detectable effect to a cell to which the compound is administered when compared to an otherwise identical cell to which the compound is not administered.

The skilled artisan would understand that the effective amount varies and can be readily determined based on a number of factors such as the disease or condition being treated, the age and health and physical condition of the mammal being treated, the severity of the disease, the particular compound being administered, and the like. Generally, the effective amount will be set between about 0.1 mg/kg to about 100 mg/kg, more preferably from about 1 mg/kg and 25 mg/kg. The compound (e.g., a truncated soluble poxvirus envelope protein, an antibody thereto, a nucleic acid encoding such proteins, and the like) can be administered through intravenous injection, including, among other things, a bolus injection. However, the invention is not limited to this method of administration.

By the term "soluble truncated" or "truncated soluble" protein as used interchangeably herein, is meant a protein truncated compared with the full-length protein, wherein a putative or actual domain that anchors or mediates association of the protein with a membrane is removed or rendered from the protein such that the protein is not associated, or is detectably less so, with the membrane than the full-length protein.

By the term "specifically binds," as used herein, is meant an antibody which recognizes and binds with a poxvirus soluble truncated envelope protein present in a sample, but which antibody does not substantially recognize or bind other molecules in the sample.

To "treat" a disease as the term is used herein, means to reduce the frequency of the disease or disorder reducing the frequency with which a symptom of the one or more symptoms disease or disorder is experienced by an animal.

By the term "vaccine" as used herein, is meant a composition, a protein or a nucleic acid encoding a protein of the invention, which serves to protect an animal against a poxvirus disease and/or to treat an animal already infected compared with an otherwise identical animal to which the vaccine is not administered or compared with the animal prior to the administration of the vaccine.

"Subunit vaccine," as used herein, means any portion of a poxvirus that can elicit a detectable immune response when administered to an animal. More preferably, a subunit vaccine means a truncated soluble poxvirus envelope protein, or combination thereof, that when administered to an animal, generates a detectable immune response to the protein, and/or to a poxvirus, when compared to the immune response, if any, in an otherwise identical animal to which the subunit vaccine is not administered.

As used herein, the term "immunizing a human against poxvirus infection" means administering to the human a composition, a protein, a nucleic acid encoding a protein, an antibody or a nucleic encoding an antibody that specifically binds with the protein, which elicits an immune response in the human, which immune response provides protection to the human against a poxvirus disease when compared with an otherwise identical human to which the composition, protein, nucleic acid, or antibody is not administered or to the human prior to such administration.

Description

It is known that various poxvirus proteins present on the virus envelope are essential and/or associated with viral infectivity in that the protein is required for, inter alia, entry of virus into cells and/or for cell-to-cell spread of virus, which spread is believed to occur via membrane fusion. In the experiments described herein, soluble truncated forms of these proteins have been stably expressed in and isolated from insect cells. These proteins, alone or in various combinations, when administered to an animal, elicit an immune response, including antibodies associated therewith, which serve to neutralize virus in a virus neutralization cell culture assay. Further, when the protein is inoculated into an animal, it elicits an immune response which serves to protect the inoculated animal against disease when the animal is challenged with infectious virus. Moreover, the antibodies elicited by immunizing an animal with these proteins also inhibit infection of cells in culture as well as protect the animal against challenge with infectious virus.

As exemplified herein, the truncated soluble poxvirus envelope protein of the invention can be obtained in large quantities for use as a vaccine for protection of humans against poxvirus (e.g., cowpox, smallpox, monkeypox and the like) infection, or for reducing the severity of recurrent and/or ongoing poxvirus infection in humans. The protein is also useful as a diagnostic reagent for assessing the presence or absence of a poxvirus infection in a human. Such an assessment is made by obtaining serum from the individual and reacting it with the protein in a standard immunoassay such as, but not limited to, radioimmunoassay (RIA) or enzyme linked immunoadsorbent assay (ELISA), or ELISPOT.

Homologs of the nucleic acids encoding *vaccinia* virus envelope proteins have been identified in *variola* virus and the differences between the sequences encoding the proteins have been well-characterized in the art.

Further, the high degree of sequence identity between *vaccinia*, monkeypox and *variola* viruses makes it possible to truncate the *variola* homologs, based on the successful truncation of the *vaccinia* proteins as disclosed herein, to produce truncated soluble *variola* homologs. These homologs can be used either alone, combined with each other, combined with *vaccinia* homologs, and/or combined with other soluble truncated *vaccinia* proteins that are non-homologs, in the methods of the invention, e.g., to treat and prevent *variola* infection in humans and to produce useful antibodies, among other things. Such combinations and uses of *vaccinia* and/or *variola* or monkeypox proteins of the invention are encompassed in the present invention as would be appreciated by the skilled artisan once armed with the teachings provided herein given the extensive knowledge in the art regarding the similarities and differences among the sequences of numerous poxviruses. Indeed, the entire genome of *vaccinia* virus has been sequenced (e.g., GenBank Accession No. AY243312), and extensive sequence data has been produced regarding the other poxviruses. Thus, the invention is not limited to a soluble truncated *vaccinia* protein. Rather, the invention encompasses soluble truncated poxvirus envelope proteins derived from both *vaccinia* and *variola* and monkeypox, and any combination thereof, which proteins can be used as vaccines to, among other things, protect humans from disease caused by either of these two types of viruses. As the data presented herein establish, antibody directed against soluble truncated poxvirus envelope protein serves to neutralize infection of cells in culture by *vaccinia*. Since this is an art-recognized model for assessing the efficacy of immunization against *variola* and due to the high degree of homology between the two viruses wherein the protein homologs are highly conserved, the invention encompasses proteins from either *vaccinia* or *variola* or monkeypox virus type which serve to protect cells and humans against infection by both *vaccinia* and/or *variola*.

The vaccine of the invention may therefore comprise at least one protein derived from *vaccinia* and another protein derived from *vaccinia* and/or *variola*, and any variation thereof. One vaccine comprises *vaccinia* A33Rt and further comprises L1R(185t) and/or B5Rt. However, the invention is not limited to this, or any other particular combination of truncated soluble poxvirus envelope proteins. Instead, the invention includes a wide plethora of combinations of truncated soluble poxvirus envelope proteins, derived from *vaccinia* and/or *variola* viruses.

Further, while some embodiments are exemplified elsewhere herein, the invention is not limited to any particular combination of these novel proteins. More specifically, as would be appreciated by one skilled in the art, based upon the disclosure provided herein, a composition of the invention encompasses a composition comprising at least one of the novel truncated proteins of the invention, e.g., A33Rt, B5Rt and L1R(185t). Furthermore, the truncated A33R and B5R disclosed in Galmiche et al. (1999, Virology 254:71-80), which differ substantially from the truncated proteins of the invention, are not included herein by the terms "A33Rt", "B5Rt," and "L1R(185t)" as used herein. Nonetheless, the compositions of the invention can comprise the proteins described by Galmiche et al., in combination with the novel proteins disclosed herein.

These proteins of the invention include, but are not limited to, a truncated A33Rt protein comprising from about amino acid residue number 58 to 185 relative to the amino acid sequence of the full-length A33R protein; a truncated L1R (185t) comprising from about amino acid residue number 1 to 185 relative to the amino acid sequence of full-length L1R; a truncated B5Rt comprising from about amino acid residue number 20 to 275 relative to the amino acid sequence of full-length B5R; and a truncated A17Lt comprising from about amino acid residue number 80 to 138 relative to the amino acid sequence of full-length A17L. The invention is not limited to these proteins, nor to these particular truncations. Rather, one skilled in the art, based upon the disclosure provided herein, would understand that the present invention encompasses a wide plethora of virus proteins and truncations, wherein at least a portion of a putative membrane association domain of the protein is modified such that the protein is no longer associated with a membrane, or is less associated with the membrane, compared with an otherwise identical protein that has not been so modified.

Further, the data disclosed herein demonstrate that retention of the ectodomain of the protein, wherein such domain is exposed to on the external surface of the virus, exposes certain epitopes to the immune response such that protective and/or neutralizing antibodies are elicited. Thus, the skilled artisan, once armed with the teachings provided herein, would appreciate that the invention encompasses a wide plethora of modifications wherein an ectodomain of the protein is preserved and/or a membrane associated, e.g., a transmembrane domain, is removed or modified such that it no longer serves to associate the protein with a membrane.

The vaccine of the invention comprises a truncated A17L (designated A17Lt) which is associated with a substantially full length A27L. This is because it is known that A27L is associated with the virus membrane due to association with A17L such that truncation of A27L is not required to render this protein soluble for purposes of the present invention.

By the term "truncated" as used herein as it refers to a poxvirus envelope protein, is meant a poxvirus envelope protein which contains less than the complete number of amino acids found in a wild type protein. Particularly, the term truncated is used to mean a protein which is not membrane anchored, i.e., which comprises a deletion or other mutation which facilitates secretion of the protein from a cell or virus particle, or which otherwise renders the protein detectably less associated with a membrane than the full-length protein. Mutations in the protein which give rise to different lengths of can comprise insertion, deletion or point mutations. An insertion mutation is one where additional base pairs are inserted into a nucleic acid encoding the protein, such as, but not limited to, a mutation that causes a frameshift mutation and/or a stop codon such that the nucleic acid is not translated past the novel premature stop codon. A deletion mutation is one where base pairs have been removed from a nucleic acid molecule. A point mutation is one where a single base pair alteration has been made in a nucleic acid molecule. Each of these mutations is designed such that creation of any one of them in a nucleic acid molecule effects an alteration in the nature of any polypeptide expressed by that nucleic acid, which alteration results in a protein that does not associate with a membrane, or does so to a lesser extent, compared with the wild type full-length protein which is not truncated or modified.

The composition can also include a substantially full length poxvirus envelope protein, which can comprise all of the amino acids of that protein, such as, but not limited to, full length A27L, which is soluble where it is associated with a truncated soluble A17Rt, where association with a soluble A17Rt instead of a membrane-associated A17R renders the unmodified A27L soluble by virtue of the modification in the solubility of its binding partner.

By the term "substantially full length" protein, as the term is used herein, is meant a poxvirus envelope protein which comprises a sufficient number of amino acids so that the substantially full length protein is capable of associating with a membrane and which has biological activity that is not detectably different than the wild type unmodified protein. Thus, a substantially full length protein need not necessarily contain all of the amino acids which comprise the wild type protein (although according to the invention, it may); rather, the molecule comprises a substantial portion of the molecule sufficient for binding to a membrane.

The invention should not be construed to be limited to any particular specific length of truncated protein. Rather, the invention should be construed to encompass any length of a truncated protein which binds with a membrane to a lesser extent than the full-length protein. The procedures which are used to generate plasmids expressing proteins of different lengths are well known in the art and the means for expressing the protein of interest in a cell are described in detail herein and are also well-known in the art and described in numerous treatises including, among many others, Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

The invention should also be construed to include any form of a poxvirus envelope protein having substantial homology to the proteins disclosed herein. Preferably, a soluble truncated poxvirus envelope protein which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the proteins disclosed herein. More preferably, the amino acid sequence of a truncated soluble poxvirus envelope protein as disclosed herein is the sequence of e.g., A33Rt [SEQ ID NO:4], B5Rt [SEQ ID NO:5], and L1R(185t) [SEQ ID NO:1]).

Moreover, the invention encompasses a nucleic acid encoding a truncated soluble poxvirus protein of the invention where the amino acid sequence of the protein encoded by the nucleic acid shares substantial homology with the nucleic acids encoding the proteins disclosed herein. That is, preferably, a nucleic acid encoding a soluble truncated poxvirus envelope protein encodes a protein wherein the amino acid sequence of the protein shares at least about 70% homology, more preferably at least about 80% homology, even more preferably, at least about 90% homology, more preferably, at least about 95% homology, and more preferably, at least about 99% homology with an amino acid sequence of a truncated soluble poxvirus envelope protein as disclosed herein (e.g., A33Rt [SEQ ID NO:3], B5Rt [SEQ ID NO:5, and L1R(185t) [SEQ ID NO:1]). More preferably, the amino acid sequence of a truncated soluble poxvirus envelope protein as disclosed herein is the sequence of, e.g., A33Rt [SEQ ID NO:3], B5Rt [SEQ ID NO:5, and L1R(185t) [SEQ ID NO:1].

Further, the invention encompasses an isolated nucleic acid encoding a soluble truncated poxvirus envelope protein having substantial homology to the proteins disclosed herein. Preferably, the nucleotide sequence of an isolated nucleic acid encoding a soluble truncated poxvirus envelope protein is "substantially homologous", that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a protein disclosed herein (e.g., A33Rt [SEQ ID NO:4], B5Rt [SEQ ID NO:6, and L1R(185t) [SEQ ID NO:2]). More preferably, the nucleotide sequence of a nucleic acid encoding a truncated soluble poxvirus envelope protein as disclosed herein is the sequence of (e.g., A33Rt [SEQ ID NO:4], B5Rt [SEQ ID NO:6, and L1R(185t) [SEQ ID NO:2]). To produce a protein of the invention, following the teaching provided herein, it is well within the skill of those in the art to take a plasmid encoding truncated envelope protein from a mammalian poxvirus (e.g., *vaccinia* and smallpox [*variola*]), and introduce it into a population of cells (e.g., insect, mammalian, yeast, bacteria and the like) such that the cells become stably transfected with the plasmid and are caused to express and secrete a soluble form of the protein as described herein. In addition, the truncated protein may be insoluble in the cell and then solubilized by standard denaturation and refolding methods. It is also well within the skill of those in the art to take yet another plasmid encoding another poxvirus protein (i.e., a protein from a different virus type than the first protein, a different protein from the same strain, the same protein but comprising a different truncation, and the like), and generate cell lines which secrete soluble truncated proteins of the invention following the teaching contained herein. That is, the skilled artisan, based upon the disclosure provided herein, including, but not limited to, that the subunit vaccine of the invention comprises combinations of various poxvirus proteins, would appreciate that nucleic acids encoding one, or more, such proteins, can be introduced into a recombinant cell either via a single vector comprising multiple nucleic acids, or via several vectors, each encoding at least one of the proteins of interest. Alternatively, the skilled artisan would understand that the proteins can each be produced separately using separate recombinant cells and vectors, and all permutations of these methods would be understood by one skilled in the art to be encompassed by the present invention once the artisan is provided with the teachings provided herein.

Thus, the invention should not be construed to be limited to the particular method of introduction of poxvirus DNA into cells described herein. Rather, other methods may be used to generate cells which express a truncated soluble poxvirus envelope protein of the invention. Such methods include, but are not limited to, the use of retroviral and other viral vectors for delivery of nucleic acid encoding a protein of the invention (including an antibody directed against the proteins of the invention) into cells and the use of other chemical means of transfection. In addition, as described herein, the proteins to be expressed by cells can include a mixture of truncated soluble poxvirus envelope proteins derived from various virus types such that a single recombinant strain can produce, for instance, a *vaccinia* A33Rt protein and a *variola* A33Rt homolog, or a *variola* homolog of a different protein, such as a *variola* B6Rt homolog of *vaccinia* B5Rt, and so forth. Thus, a recombinant cell can produce various proteins of the invention, and the invention is not limited in any way as to the number and combination of exogenous nucleic acids and proteins that can be produced by the cell. Generation of such recombinant cells, and other relevant protocols available to those skilled in the art, are described, for example, in Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

The invention includes any expression system known in the art or disclosed herein for production of proteins of interest, such as expression in a baculovirus system, a yeast expression system, or a mammalian cell system or a bacterial system, such as, but not limited to, CHO cells. Proteins of the invention which are generated by synthetic methods are also included in the invention.

Also contemplated by the invention is a subunit vaccine comprising an isolated nucleic acid, preferably, an isolated DNA, encoding a truncated soluble poxvirus envelope protein. Such a nucleic acid, preferably, a DNA molecule, may be used directly as a vaccine as described herein, or it may be used to transfect cells in order to produce large quantities of the truncated soluble poxvirus envelope protein for use as a subunit vaccine.

The skilled artisan, based upon the disclosure provided herein, would appreciate that the nucleic acids encoding the proteins of the invention (e.g., a truncated soluble poxvirus envelope protein and an antibody directed thereto) can be expressed alone or in combination with other proteins either in one or separate recombinant cells. Where the proteins are expressed in the same recombinant cell, the exogenous nucleic acids encoding the proteins can be ligated together in either of two configurations. In the first configuration, a plasmid, or other suitable vector, is generated having the following elements: a promoter/regulatory sequence for expression of the first protein, which promoter is operably linked to and positioned upstream of a nucleic acid sequence encoding the first protein, and a promoter for expression of the second protein, which is positioned upstream of a nucleic acid encoding the second protein. The plasmid therefore encodes both proteins on the same contiguous nucleic acid molecule wherein expression of each protein is under the control of an individual promoter/regulatory sequence, preferably, but not necessarily, the same promoter sequence. Both proteins are expressed individually from this plasmid, or other vector, in a cell and form complex therein which is secreted from the cells as described herein.

Alternatively, a plasmid can be generated which has the following elements: a single a promoter/regulatory sequence which is positioned upstream of a nucleic acid encoding a first protein and a sequence encoding a second protein, the sequences encoding the proteins of interest being separated by a nucleic acid sequence encoding a cleavage site for a protease. In this plasmid, the protein-coding sequences can be positioned in the plasmid, or other vector, in either orientation with respect to each other, such that either one of them is juxtaposed to the promoter sequence. DNA encoding the protease cleavage site, which is positioned between the sequences encoding the proteins may be any DNA known to encode a length of amino acids which are cleaved by any protease which is present in a majority of cells and which is particularly present in cells into which the DNA of the invention is introduced. The proteins expressed by this plasmid, or other vector, are expressed as a single contiguous protein comprising the amino acid sequences of each protein fused together and comprising an intervening protease cleavage site. Subsequent cleavage of the fused protein by the appropriate protease generates individual polypeptides to form a composition and/or subunit vaccine as described elsewhere herein.

The isolated nucleic acid of the invention is not limited to a plasmid based nucleic acid, but rather may include any form of nucleic acid which encodes a protein of the invention as exemplified herein in the case of a plasmid DNA used in a baculovirus/insect cell expression system, but not limited in any way to this, or any other, expression method. Thus, the isolated DNA of the invention can include a viral vector, a non-viral vector, or a plasmid DNA, among others. See, e.g., Sambrook and Russell, supra, and Ausubel et al., supra.

The promoter/regulatory sequence which is used to drive expression of a protein of the invention (i.e., a truncated soluble poxvirus envelope protein, and an antibody thereto) in either type of configuration can be any constitutive promoter which drives expression of these proteins in cells. Such promoters therefore include, but are not limited to, the cytomegalovirus immediate early promoter/regulatory sequence, the SV40 early promoter/enhancer sequence, the Rous sarcoma virus promoter/enhancer, a baculovirus expression sequence, and any other suitable promoter which is available in the art for constitutive expression of high level's of proteins in cells.

When the isolated DNA of the invention is used to generate large quantities of the proteins of the invention, cells are transfected with the DNA using the methodology disclosed herein or any other available transfection methodology, the protein of interest is expressed and is recovered from the cells as described herein.

When the isolated DNA is to be used as a vaccine, a DNA based vaccine is prepared following the disclosure described in Wang et al. (1993, Proc. Natl. Acad. Sci. USA 90:4156-4160). The nucleic acid vaccine comprises DNA encoding a truncated soluble poxvirus envelope protein of the invention expressed under the control of any of the promoters disclosed herein. Antibodies are raised against the expressed protein by intramuscular injection of DNA into the hind limb of six to eight week old mice. The anesthetic bupivacaine (50 µl of a 0.5% solution) is used to improve immunogenicity of the vaccine. The animals are immunized first with bupivacaine and then are immunized the following day with 50 μg of plasmid DNA encoding the protein of the invention. At about four weeks, animals are test bled to measure the level of anti-virus protein antibody and are re-injected with bupivacaine and DNA on successive days. On or about day 45, serum is collected from the animals and is tested to determine whether antibodies contained therein neutralize virus in the virus neutralization assays described herein. DNA encoding other poxvirus proteins, such as, but not limited to, proteins associated with and/or which mediate immune evasion as discussed elsewhere herein, can be included for immunization of the animal using the same protocol.

To adapt this DNA based vaccine to human subjects, the amounts of DNA, the route of injection and the adjuvants to be used can vary from that described previously. However, these variations will be readily apparent to the skilled artisan working in the field of nucleic acid-based vaccines.

The invention should be construed to include any and all isolated nucleic acids which are homologous to the nucleic acids described and referenced herein, provided these homologous DNAs have the biological activity of the proteins disclosed herein, including, but not limited, being truncated soluble forms of a virus envelope protein where antibodies elicited by the protein, inhibit virus plaque formation in vitro, protect an animal from virus infection and/or treat an ongoing infection, all as disclosed elsewhere herein.

To purify a protein of the invention for use as a vaccine or other therapeutic, the examples given in the experimental details section may be followed. However, the invention is not limited to any particular protein purification method. For example, a substantially pure preparation of a protein of the invention is obtained by immunoaffinity chromatography of supernatants obtained from cells which express and secrete the protein using an antibody (polyclonal and/or monoclonal), that is, any antibody which specifically binds the protein. Additionally, as exemplified elsewhere herein, a tag sequence can be added to the amino acid sequence of the protein of interest and the tag peptide portion of the fusion protein can be used to isolate the fusion protein comprising the tag. Numerous tag polypeptides are known in the art and include a 6-Histidine tag peptide as was used to purify the proteins of the invention as exemplified herein. Numerous tag sequences are available in the art and are therefore not further described herein. The proteins can also be purified by biochemical methods, such as, column chromatography using ion exchange, size exclusion, or reverse phase. Also, combinations of the various purification schemes is also encompassed, such as, but not limited to, further purification of the protein following, e.g., $Ni^{++}$ chromatography by using, for instance, cation exchange, and all combinations of methods for protein purification known in the art, or to be developed in the future, are included in the invention.

The skilled artisan would understand that the nucleic acids of the invention encompass an RNA or a DNA sequence encoding a protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook and Russell, supra, and Ausubel et al., supra. Procedures for the introduction of amino acid changes in a protein or polypeptide by altering the DNA sequence encoding the polypeptide are well known in the art and are also described in these, and other, treatises.

The invention includes a nucleic acid encoding a truncated soluble poxvirus envelope protein wherein a nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one protein of the invention, or biologically active fragment thereof. Such tag polypeptides are well known in the art and include, for instance, green fluorescent protein (GFP), an influenza virus hemagglutinin tag polypeptide, a herpesvirus tag polypeptide, myc, myc-pyruvate kinase (myc-PK), $HiS_6$, maltose binding protein (MBP), a FLAG tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize a protein of the invention, or a biologically active fragment thereof, within a cell, a tissue, and/or a whole organism (e.g., a human, and the like), and to study the role(s) of an the virus protein in a cell. Further, addition of a tag polypeptide facilitates isolation and purification of the "tagged" protein such that the proteins of the invention can be produced and purified readily.

The present invention also provides for analogs of proteins or peptides which comprise a truncated soluble poxvirus envelope protein as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are truncated soluble poxvirus envelope proteins which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a truncated soluble poxvirus envelope protein of the present invention (e.g., following deletion of all, or a substantial portion, of a transmembrane region, rendering the protein soluble when compared to the full-length peptide, the protein elicits protective/neutralizing immune response, including, antibodies that specifically bind with the protein and can passively protect an animal from virus infection, such that the proteins of the invention inhibit virus infection as demonstrated both in vitro and in various art-recognized poxvirus infection animal models).

Among a "biological activity", as used herein, is included a truncated soluble poxvirus envelope protein which when inoculated into an animal elicits an antibody, a virus neutralizing antibody, which neutralizes the infectivity of a poxvirus in a virus neutralization assay and which protects an animal against disease when wild type virus is subsequently administered to the animal.

Typically, a virus neutralization assay involves incubation with a known titer of infectious virus of serial dilutions of serum obtained from an animal administered the vaccine for a period of time. Following the incubation period, the amount of infectious virus remaining is quantitated, usually by plaque assay.

The term "virus neutralizing effective amount" as used herein, means an amount of protein which elicits an immune response when administered to an animal, which response is capable of neutralizing virus infectivity to a level which is less than 50% of normal infectivity in a standard virus neutralization assay, wherein normal infectivity is assessed relative to an otherwise identical animal to which the protein is not administered.

A virus neutralizing immune response is also one which affords protection to the animal from lethal challenge with wild type virus. Protection against lethal challenge with wild type virus is typically assessed by first immunizing a series of animals with the subject antigen to generate serum capable of neutralizing virus infectivity in a standard virus neutralization assay. The animals are then inoculated with a serial dilutions of wild type virus, which dilutions contain sufficient virus to kill non-immunized animals. The death rate, or rate/amount of weight loss, of the animals is quantitated and is compared to the level of the virus neutralizing immune response in each of the animals. Protection from lethal challenge has been effected when non-immunized animals die and immunized animals do not die as a result of infection with virus.

By the term "virus neutralizing antibody" as used herein, is meant a reduction in the infectivity of a virus in the presence of the antibody compared with the infectivity of the virus in the absence of the antibody. Typically, an antibody is a virus neutralizing antibody when the infectivity of the virus is reduced by about 50% in the presence of the antibody at a dilution of the serum containing the antibody which is greater than 1:20. The higher the dilution of serum which neutralizes a constant amount of virus by 50%, the greater the estimate of the activity of the antibody contained within the serum.

The term "protect an animal against disease" is used herein to mean a reduction in the level of disease caused by a wild type virus in an animal inoculated with a truncated soluble poxvirus envelope protein of the invention compared with the level of disease caused by a wild type virus in an animal which as not been inoculated with the protein. As the data presented herein establish, the protein of the invention, and/or combinations thereof, protected an animal against infection by poxvirus (*vaccinia*) at least as much as, if not better, than the Wyeth Dryvax vaccine, which is the current "gold standard" for smallpox vaccination. Thus, the subunit vaccine of the invention is capable of protecting an animal against smallpox disease to a level at least as good as that observed when the Wyeth Dryvax vaccine is used to immunize an animal.

To determine whether a subunit vaccine (e.g., a truncated soluble poxvirus envelope protein of the invention) generated using the methods described herein has biological activity, the following general protocols are followed. To assess biological activity of a subunit vaccine, an animal is first immunized with the protein. Although the examples provided herein are directed to rabbits, mice, and monkeys, any other animal may be used.

Using mice as an example, a mouse is immunized at about biweekly intervals with about four doses ranging from about 0.5 μg to 50 mg of a protein of the invention per dose. Serum obtained from the mouse post-immunization is tested for the presence of an anti-protein antibody in any immunological assay, for example, an ELISA. A virus neutralization assay is performed wherein dilutions of serum obtained from the immunized animal are mixed with infectious virus. The mixture is added to cells and neutralization of virus by the antibody is measured as described herein, including, but not limited to, assessing the extent of plaque neutralization and/or comet tail formation in culture.

To determine the efficacy of the truncated protein as a vaccine, the protein, and combinations thereof, is administered intraperitoneally to mice using an adjuvant system suitable for administration of proteins to mice, for example, the Ribi adjuvant system (RAS; Ribi Immunochemical Research, Hamilton, Mont.), or other suitable adjuvant. Both pre- and post-immune serum is obtained from the mice and the presence or absence of antibodies is determined in the standard assays described herein or any other assay known in the art or to be developed in the future. The ability of anti-truncated protein antibodies to neutralize poxvirus (e.g., *vaccinia* and/or *variola*) is determined in a standard viral neutralization assay, such as but not limited to, a plaque reduction neutralization assay.

Mice are administered a range of concentrations of protein ranging from about 0.1 to about 20 μg per dose, using several different immunization schedules, i.e., weekly, biweekly, in order to determine the optimum conditions for effective immunization of the mice against poxvirus. Sera obtained from mice so immunized are tested for the ability to neutralize poxvirus Western Reserve (WR), or other strain of poxvirus depending on the virus from which the protein is derived) and other strains of both *vaccinia* and *variola*. Since the ability of an antibody to neutralize virus in culture is predictive of the protective activity of that antibody, neutralization of any one of the viruses listed above by antibody raised against the protein is predictive of the ability of protein to serve as a subunit vaccine candidate against that virus. Further, since testing using *variola* virus, or protein homologs thereof, is restricted, and because the art-recognized methods for assessing the efficacy of a vaccine directed against *variola* is to use *vaccinia* virus as a model, *vaccinia* virus-based methods are predictive and can be used to assess whether a protein of the invention is a potential subunit vaccine candidate to treat/prevent smallpox infection. Also, the invention encompasses methods to assess the efficacy of a protein of the invention in development of VIG to treat complications associated with smallpox vaccination, and such methods are exemplified and encompassed herein as are other methods known in the art.

To assess whether antibody raised against a truncated soluble protein of the invention protects mice against in vivo challenge with virus, immunized and non-immunized mice are administered various concentrations of virus intranasally (IN) at a time post-immunization when peak antibody levels are apparent following the experiments described above. The number of immunized animals which survive challenge by virus is indicative of the efficacy of the protein as a subunit vaccine candidate. Although these studies may be conducted using an IN route, studies on the vaccine capabilities of a protein of the invention can involve all possible routes of administration including, but not limited to, intraperitoneal (IP), intradermal (ID), intracerebral (IC), intramuscular (IM), subcutaneous (SC), intraoccular, and even oral routes of administration. In addition, as described in the experimental details section herein, other animal models for poxvirus infection, such as monkeys, are encompassed.

The subunit vaccine of the invention may be formulated to be suspended in a pharmaceutically acceptable carrier suitable for use in animals and in particular, in humans. Such formulations include the use of adjuvants such as muramyl dipeptide derivatives (MDP) or analogs which are described in U.S. Pat. Nos. 4,082,735; 4,082,736; 4,101,536; 4,185,089; 4,235,771; and, 4,406,890. Other adjuvants which are useful include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic), a non-ionic surfactant, and a metabolizable oil such as squalene (U.S. Pat. No. 4,606,918).

The subunit vaccine of the invention may be encapsulated into liposomes for administration to the animal. See for example, U.S. Pat. Nos. 4,053,585, 4,261,975 and 4,406,890.

The subunit vaccine (i.e., truncated soluble poxvirus envelope protein) of the invention is administered to a human by any suitable route of administration, for example, subcutaneously, intramuscularly, orally, intravenously, intradermally, intranasally or intravaginally. The complex is first suspended in a pharmaceutically acceptable carrier which is suitable for the chosen route of administration and which will be readily apparent to those skilled in the art of vaccine preparation and administration. The dose of vaccine to be used may vary dependent upon any number of factors including the age of the individual and the route of administration. Typically, the subunit vaccine is administered in a range of 0.5 μg to 50 mg of protein per dose. Approximately 1-10 doses are administered to the individual at intervals ranging from once per week, to once per month, to once per year, to once every few years.

The protein of the invention, which are identified using any of the methods described herein, can be formulated and administered to a mammal for treatment and/or prevention of poxvirus (e.g., *vaccinia, variola*, and the like) infection as now described.

The invention encompasses the preparation and use of pharmaceutical compositions comprising a protein useful for treatment of poxvirus infection as an active ingredient. Such a pharmaceutical composition may consist of the active ingredient alone, as a combination of at least one active ingredient (e.g., an immunogenic dose of a truncated soluble envelope protein) in a form suitable for administration to a subject, or the pharmaceutical composition may comprise the active ingredient and one or more pharmaceutically acceptable carriers, one or more additional (active and/or inactive) ingredients, or some combination of these.

The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers and AZT, protease inhibitors, reverse transcriptase inhibitors, interleukin-2, interferons, cytokines, and the like.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized *maize* starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Typically dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

A compound used to treat poxvirus infection may be co-administered with the immunogenic dose of a subunit vaccine of the invention. Alternatively, the compound(s) may be administered an hour, a day, a week, a month, or even more, in advance of the immunogenic dose(s) of a subunit vaccine, or any permutation thereof. Further, the compound(s) may be administered an hour, a day, a week, or even more, after the immunogenic dose(s) of a subunit vaccine, or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and the subunit vaccine, and the like.

The vaccine of the invention is useful for prevention of poxvirus disease in an animal, preferably a human. However, the vaccine is also useful as a therapeutic agent for treatment of ongoing poxvirus infection in order to boost the immune response in the animal. Thus the invention contemplates both prophylactic and therapeutic uses for the subunit vaccine of the invention.

It should be appreciated that the subunit vaccine of the invention may be combined with other subunit vaccines, such as subunit vaccines comprising other truncated or full-length poxvirus envelope proteins, including proteins that can mediate immune evasion, or combinations thereof, and the like, each of which may be generated and used according to published protocols and the procedures described herein.

The antibodies which are produced in animals may themselves serve as therapeutic compounds for treatment of poxvirus infection, particularly in severely immunocompromised individuals, such as newborns, those infected with human immunodeficiency virus or those receiving transplants. The antibody can also be useful for administration to individuals afflicted with complications following smallpox vaccination with, among other vaccines, the Wyeth Dryvax vaccine currently used for such purposes. Thus, the invention provides a novel therapeutic VIG without need to immunize vaccinees to obtain the VIG thereby placing those vaccinees at risk for similar complications. The invention should therefore be construed to include anti-truncated soluble protein antibodies as described herein and such antibodies which may be modified such that they are phage displayed and/or humanized using technology available in the art. It will be appreciated that the antibodies which are useful include those which specifically bind to a truncated soluble envelope protein derived from either *vaccinia* and/or *variola* and a composition wherein one component is derived from *vaccinia* and the other component is derived from *variola*. Similarly, DNA encoding antibodies which are now described may comprises DNAs encoding truncated soluble envelope protein derived from either *vaccinia* and/or *variola* and combinations thereof.

The generation of polyclonal and monoclonal antibodies is well known in the art and is described and referenced herein. Phage displayed and humanized antibodies are also well known in the art and are also described herein.

Given the advances in technology in cloning nucleic acids encoding proteins comprising antibodies, the invention should also be construed to include an isolated nucleic acid which encodes an antibody that specifically binds a truncated soluble poxvirus envelope protein of the invention, or a portion or fragment of such antibody.

When the antibody of the invention is a monoclonal antibody, the nucleic acid encoding the antibody may be cloned and sequenced using technology which is available in the art, and is described, for example, in Wright et al. (1992, Critical Rev. in Immunol. 12(3,4): 125-168) and the references cited therein. Further, the antibody of the invention may be "humanized" using the technology described in Wright et al., (supra) and in the references cited therein.

For example, to generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook and Russell (2001, Molecular Cloning, A Laboratory Approach, Cold Spring Harbor Press, Cold Spring Harbor, N.Y.), and Ausubel et al. (2002, Current Protocols in Molecular Biology, John Wiley & Sons, NY).

Bacteriophage which encode the desired antibody can be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such "panning" techniques are well known in the art and are described for example, in Wright et al. (supra).

Processes such as those described above, have been developed for the production of human antibodies using M13 bacteriophage display (Burton et al., 1994, *Adv. Immunol.* 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein, is meant an antibody which recognizes and binds a poxvirus protein of the invention, but does not substantially recognize or bind other molecules in a sample.

The invention thus includes an isolated DNA encoding a truncated soluble envelope protein-antibody, or a portion of the antibody of the invention. To isolate DNA encoding an antibody, for example, DNA is extracted from antibody expressing phage obtained according to the methods of the invention. Such extraction techniques are well known in the art and are described, for example, in Sambrook et al. (supra).

The subunit vaccine antibody of the invention may be conventionally administered to a mammal, preferably a human, parenterally, by injection, for example, subcutaneously, intravenously, intramuscularly, and the like. Additional formulations which are suitable for other modes of administration include suppositories, intranasal aerosols and, in some cases, oral formulations. The antibody may be administered in any of the described formulations either daily, several times daily, weekly, bi-weekly or monthly or several times a year in a dosage which will be apparent to the skilled artisan and will depend on the type of disease being treated. Preferably, the dosage will range from about 1 nanogram of antibody to several milligrams of antibody to even up to about 100 milligrams of antibody per dose.

It will be appreciated that the subunit vaccine of the invention, the DNA vaccine of the invention and the antibody of the invention may be used to prevent or treat poxvirus infections in a human in cases where the human is not yet infected, in cases where the human is infected and treatment is initiated in order to prevent more severe infection, and in cases where the human is suffering from complications following standard smallpox immunization protocols.

In addition, the compositions of the invention are useful for treatment of neonates at risk for developing severe poxvirus infection and for immunosuppressed individuals at risk for developing severe poxvirus infection, such as is the case in patients having acquired immunodeficiency syndrome and in transplant patients and those requiring and/or undergoing chemotherapy.

The invention includes various kits which comprise a protein of the invention, a nucleic acid encoding the protein, an antibody that specifically binds to the protein, and/or a nucleic acid encoding the antibody of the invention, an applicator, and instructional materials which describe use of the kit to perform the methods of the invention. Although exemplary kits are described below, the contents of other useful kits will be apparent to the skilled artisan in light of the present disclosure. Each of these kits is included within the invention.

In one aspect, the invention includes a kit for treating a poxvirus infection in a human. The kit is used pursuant to the methods disclosed in the invention. Briefly, the kit may be used to administer an protein of the invention, or a biologically active fragment thereof, to a mammal (e.g., a human) having a poxvirus infection, or at risk of contracting a poxvirus infection. This is because, as more fully disclosed elsewhere herein, the data disclosed herein demonstrate that the protein of the invention, or an antibody thereto, when administered to an animal in an art-recognized model of human poxvirus infection, either alone or in combination with other such proteins, elicits an immune response that protects the animal from poxvirus infection, or treats an ongoing infection in the human. Further, the protein of the invention, or the antibody thereto, can be administered in the form of a nucleic acid encoding the protein and/or antibody to achieve similar therapeutic results.

The kit further comprises an applicator useful for administering the protein, antibody, or nucleic acid encoding them, to the animal. The particular applicator included in the kit will depend on, e.g., the method used to administer the protein, antibody, and/or nucleic acid encoding the same, as well as the animal to which the protein and/or nucleic acid of the invention is to be administered, and such applicators are well-known in the art and may include, among other things, a pipette, a syringe, a dropper, and the like. Moreover, the kit comprises an instructional material for the use of the kit. These instructions simply embody the disclosure provided herein.

The kit includes a pharmaceutically-acceptable carrier. The composition is provided in an appropriate amount as set forth elsewhere herein. Further, the route of administration and the frequency of administration are as previously set forth elsewhere herein.

Further, the kit includes a kit comprising a combination of the proteins of the invention, such as, but not limited to, A33Rt, B5Rt and/or L1R(185t), and any combination thereof. Also, as more fully discussed elsewhere herein, an antibody directed to any or any combination of these proteins can also be used to treat ongoing infection and/or to immunize a human thereby preventing infection. Additionally, the invention encompasses kits comprising a nucleic acid encoding the proteins of the invention and/or a nucleic acid encoding an antibody directed against a protein of the invention, and the invention encompasses a kit comprising a combination of all the preceding antibodies, proteins and nucleic acids, as would be appreciated by one skilled in the art based upon the disclosure provided herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Development of a Subunit Vaccine Against Smallpox (*Variola*) Virus

The data disclosed herein provide, for the first time, a protein subunit poxvirus vaccine that incorporates novel truncated forms of major targets of the protective response. Such a vaccine offers advantages over VV- as well as MVA-based smallpox vaccines. For example, a vaccine of the present invention can be safely administered to at risk individuals, wherein the vaccine incorporates both *variola* and *vaccinia* proteins in the mixture and thereby can overcome important immune evasion strategies by the smallpox virus where VV, but not *variola*, antigens are used. This is because *variola* proteins may differ antigenically from their VV counterparts, such that incorporating both *variola* and *vaccinia* proteins in the novel subunit vaccine affords a more protective response. Such a multi-component subunit vaccine offers a significant advantage over prior art VV and MVA vaccines.

The data disclosed herein demonstrate successful cloning, expression and purification of VV glycoproteins of interest, including, but not limited to A33R, L1R, B5R, A27L, A17L, D8L and H3L, using a baculovirus expression system. The data further suggests that *variola* homologues of these proteins, e.g., L1R and A33R, can be produced and compared with VV homologs to provide novel poxvirus subunit vaccine components. The efficacy of VV and *variola* protein subunit vaccines can be readily tested using an art-recognized mouse model of VV infection Also, ectodomains of several VV envelope glycoproteins were identified, cloned and expressed using a baculovirus expression system. The expressed proteins can be cloned and expressed using a polypeptide sequence, such as demonstrated herein using a six histidine tag. The six histidine tag can be used to purify secreted proteins using nickel chromatography. Monoclonal and polyclonal antibodies were developed to these proteins.

Further, the novel proteins of the invention were assayed using protection experiments to access whether antibody thereto can protect a mammal from VV infection. Previously, a similar approach was used to overexpress herpes virus glycoproteins and cellular receptors using the baculovirus system (Carfi et al., 2001, Molecular Cell. 8:169-179; Connolly et al., 2001, Virology. 280:7-18; Geraghty et al., 1998, Science. 280:1618-1620; Krummenacher et al., 1998, J. Virol. 72:7064-7074; Krummenacher et al., 1999, J. Virol. 73:8127-8137; Milne et al., 2001, Virology. 281:315-328; Nicola et al., 1997, J. Virol. 71:2940-2946; Nicola et al., 1996, J. Virol. 70:3815-3822; Rux et al., 1998, J. Virol. 72:7091-7098; Sisk et al., 1994, J. Virol. 68:766-775; Whitbeck et al., 2001, J. Virol. 75:171-180; Willis et al., 1998, J. Virol. 72:5937-5947).

The data disclosed herein demonstrate, for the first time, application of the baculovirus expression system to poxviruses for development of protein subunit vaccines for these pathogens comprising a truncated L1R protein. Moreover, additional novel truncated proteins, e.g., A33Rt and B5Rt, have also been produced using a baculovirus expression system, which proteins differ from any produced previously. That is, the data disclosed demonstrate that the baculovirus system was used to expand the number of baculovirus produced proteins to include potential targets of the protective immune response, including but not limited to, L1R, A27L, A17L, D8L, and H3L. The proteins were chosen on the basis that they are found in the virus and that they have previously been demonstrated to stimulate and/or be associated with a protective immune response.

Subunit Vaccine Potential Candidates

Ramirez et al. (2002, J. Gen. Virol. 83: 1059-67), demonstrated that a MAb to A27L (IMV) neutralized virus infectivity and protected mice in passive immunization experiments. Immunization of mice with A27 produced in *E. coli* produced neutralizing antibody and protected mice against challenge with *vaccinia* virus (Lai et al., 1991, J. of Virol. 65:5631-5635). A27L forms a complex with A17L and this complex might be more immunogenic than A27L alone (Rodriguez et al., 1993, J. Virol. 67:3435-3440). D8L and H3L also stimulate virus neutralizing antibody production and can be important components of a subunit vaccine. These four proteins are cloned, expressed and tested for efficacy in a mouse model of VV infection as exemplified herein for various VV proteins. Further, other proteins of EEV (see table 1) can also be cloned, expressed and tested for efficacy. In addition, *variola* homologues of L1R and A33R, and other proteins, such as, but not limited to, those set forth at Table 1, can be tested to demonstrate that immunization with both VV and/or *variola* proteins can provide an added benefit from that of immunization with VV proteins alone.

TABLE 1

| Protein | IMV | CEV | EEV | Other Properties |
|---------|-----|-----|-----|------------------|
| L1R | yes | yes | yes | Associated with virus neutralization |
| A27L | yes | yes | yes | Virus neutralization, forms complex with A17L |
| A17L | yes | yes | yes | Virus neutralization, forms complex with A27L |
| D8L | yes | yes | yes | Virus neutralization |
| H3L | yes | yes | yes | Virus neutralization |
| F9L | yes | yes | yes | Like L1R in structure, possibly in function |
| A33R | no | yes | yes | Associated with protection, cell spread, cell adhesion of CEV |
| B5R | no | yes | yes | Virus neutralization, syncytia formation, cell adhesion of CEV |

TABLE 1-continued

| Protein | IMV | CEV | EEV | Other Properties |
|---------|-----|-----|-----|------------------|
| A56R | no | yes | yes | Mutations associated with syncytia, cell adhesion of CEV |
| A34R | no | yes | yes | Cell Adhesion of CEV |
| F13L | no | yes | yes | unknown |

Of the known 200 proteins encoded by VV, a small number are known to contain epitopes that elicit neutralizing antibodies, while others can induce different protective responses (Ramirez et al., 2002, J. Gen. Virol. 83: 1059-67), these are: H3L (Cordon et al., 1991, Virology. 181:671-686), A27L (Ramirez et al., 2002, J. Gen. Virol. 83: 1059-67; Rodriguez et al., 1987, Virol. 61:3550-3554; Rodriguez et al., 1985, J. Virol. 56:482-488; Rodriguez et al., 1987, J. Virol. 61:395-404), B5R (Galmiche et al., 1999, Virology. 254:71-80), L1R (Wolfe et al., 1995, Virology. 211:53-63), and A33R (Hooper et al., 2000, Virology 266:329-339; Galmiche et al, 1999, Virology 254:71-80).

H3L is an immunodominant glycoprotein expressed on the surface of IMV particles anchored in the viral envelope via the hydrophobic C-terminus (Fonseca et al., 2002, J. Virol. 74:7518-7528; Lin et al., 2000, J. Virol. 74:3353-3365). D8L is a 308 amino acid protein that binds to cell-surface chondrotin sulfate and is involved in adsorption of the IMV to cells (Hsiao et al., 1999, J. Virol. 73:8750-8761). A27L forms a hetero-oligomer with A17L (Betakova et al., 1999, Virology. 261:347-356; Wallengren et al., 2001, Virology. 290: 143-152) and is more fully discussed below. In each case, a histidine tag can be added to the N or C-terminus to aid in purification of the protein.

Further, a herpesvirus glycoprotein D (HSV gD) epitope tag (residues 270-279) can also be engineered onto the N- or C-terminus of the protein of interest. A preparative-scale DL6 MAb immunosorbent column can be used to purify multimilligram amounts of protein bearing these tag epitopes. Each purified protein can be tested for vaccine efficacy both singly and in combinations.

Functional Studies

Proteins and antibodies developed using the methods described elsewhere herein are useful for studies to elucidate the structure and function of these proteins and their roles in VV replication. For example, using the novel proteins of the invention, it can be assessed whether any of the proteins block infection and/or virus spread by EEV or IMV, thereby indicating that the protein of interest interacts with a cellular receptor for one of these forms of VV, thereby affecting virus infection and/or spread. Previous studies indicate that there are cellular receptors for one, or more, VV proteins, but the receptors have not been identified to date (Ichihashi, et al., 1996, Virology. 220:491-494; Law et al., 2002, J. Gen. Virol. 83:209-222; Lorenzo et al., 1998, Virology. 252:450-7; Wolfe et al., 1993, J. Virol. 67:4732-4741). Thus, the data disclosed herein provide novel methods for identifying cellular receptors that bind with poxvirus proteins.

Similar approaches using HSV led to the identification of glycoprotein D of herpes simplex virus as the receptor binding protein (Johnson et al., 1990, J. Virol. 64:2569-2576; Nicola et al., 1997, J. Virol. 71:2940-2946; Nicola et al., 1996, J. Virol. 70:3815-3822; Tal-Singer et al., 1995, J. Virol. 69:4471-4483). This finding in HSV aided in isolation and characterization of HSV receptors that interact with gD (Carfi et al., 2001, Molecular Cell. 8:169-179; Geraghty et al., 1998, Science. 280:1618-1620; Johnson et al., 1990, J. Virol. 64:2569-2576, 37, 50; Nicola et al., 1997, J. Virol. 71:2940-

2946; Nicola et al., 1996, J. Virol. 70:3815-3822; Whitbeck et al., 1997, J. Virol. 71:6083-6093), and similar approaches can be applied to identify receptors for *vaccinia* and *variola* poxviruses as disclosed elsewhere herein.

Expression of *Vaccinia* Virus Proteins in a Baculovirus Expression System

CEV and EEV each contain 11 or more proteins, 5 of which are incorporated during intracellular maturation of the IMV with extra membranes (see Table 1). All three forms, CEV, EEV and IMV, are infectious. As discussed previously elsewhere herein, IMVs are released by cell lysis and are responsible for transmission between hosts. CEVs mediate short-range cell-to-cell spread, and EEVs are involved in widespread dissemination in the host. Therefore, each form of the virus is a potential candidate for development of an effective vaccine.

The strategy for the expression of membrane proteins in baculovirus is to produce the extracellular portion of each protein in question as a truncated (designated by a "t" as follows), soluble form (Sisk et al., 1994, J. Virol. 68:766-775). Three VV proteins have been produced thus far. The ORF for the ectodomain of each glycoprotein was cloned into the transfer vector pVT-Bac, which carries the coding region for the honeybee melittin signal sequence. The signal sequence directed the protein to the secretory pathway of the infected insect (Sf9) cells. Further, a 6-histidine tag was added to the C-terminus to facilitate purification of the protein from the culture supernatant using a Nickel chromatography.

A33Rt

A33R is a 185-residue type II membrane protein with a single predicted transmembrane domain, TMD (residues 41-57). Full-length A33R forms disulfide linked dimers and is incorporated into the outer membrane of EEV (Law et al., 2002, J. Gen. Virol. 83:209-222; Payne et al., 1992, Virology. 187:251-260; Roper et al., 1996, J. Virol. 70:3753-3762). This protein is involved in facilitating direct cell-cell spread of VV employing actin-containing microvilli (Law et al., 2002, J. Gen. Virol. 83:209-222; Roper et al., 1998, J. Virol. 72:4192-204). A33R may interact with cell surface molecules of neighboring cells to facilitate cell-cell contacts for virus spread (Law et al., 2002, J. Gen. Virol. 83:209-222). Comparing VV and smallpox, *vaccinia* A33R shows about 94% identity with *variola* (Massung et al., 1994, Virology. 201: 215-40).

Briefly, the amino acid sequence of full-length *vaccinia* A33R is set forth in SEQ ID NO: 35 and is compared in FIG. 36C with the amino acid sequence of *variola* homologue thereof, termed A36R (SEQ ID NO:37), demonstrating about 94.1% identity. Further, the aa sequence of then truncated form of A33Rt is set forth in SEQ ID NO:3 and the nucleotide sequence of a nucleic acid encoding A33Rt is set forth in SEQ ID NO:4 and depicted in FIG. 34B. A predicted truncated *variola* homolog of *vaccinia* A33Rt, termed A36Rt, is depicted in FIG. 36D, and has an aa sequence set forth in SEQ ID NO:37.

The C-terminus of A33R is associated with binding of CEV to the cell surface and therefore this protein is important in cell-cell spread of VV (Law et al., 2002, J. Gen. Virol. 83:209-222). The identity of the cell or viral protein(s) to which A33R binds can be evaluated using the methods described elsewhere herein. For example, A33Rt is covalently coupled to a BIAcore chip and proteins binding with A33Rt are readily assayed. Extract from infected or uninfected cells is applied over the bound protein and protein binding therewith is detected. Analysis of the bound extract is performed using, for example, mass spectrometry.

An alternative to using a BIAcore chip is labeling a cell prior to lysis and/or binding studies. To obtain more protein, ELISA is used, for example, by biotinylating the cell surface then preparing a cell lysate and visualizing bound protein using streptavidin-HRP. With the BIAcore approach, the His tag at the C-terminus can interfere with binding of the cell or viral protein to A33Rt. Accordingly, other constructs are produced made with, e.g., the His tag at the N-terminus of the ectodomain. The protein is then oriented on the BIAcore chip with the C-terminus facing up relative to the surface of the chip by first coupling anti-his antibody to the chip surface and then using it to capture A33R by the N-terminus 6-His tag. This approach has been used successfully for studies of HSV glycoproteins and receptors.

Figure 5:
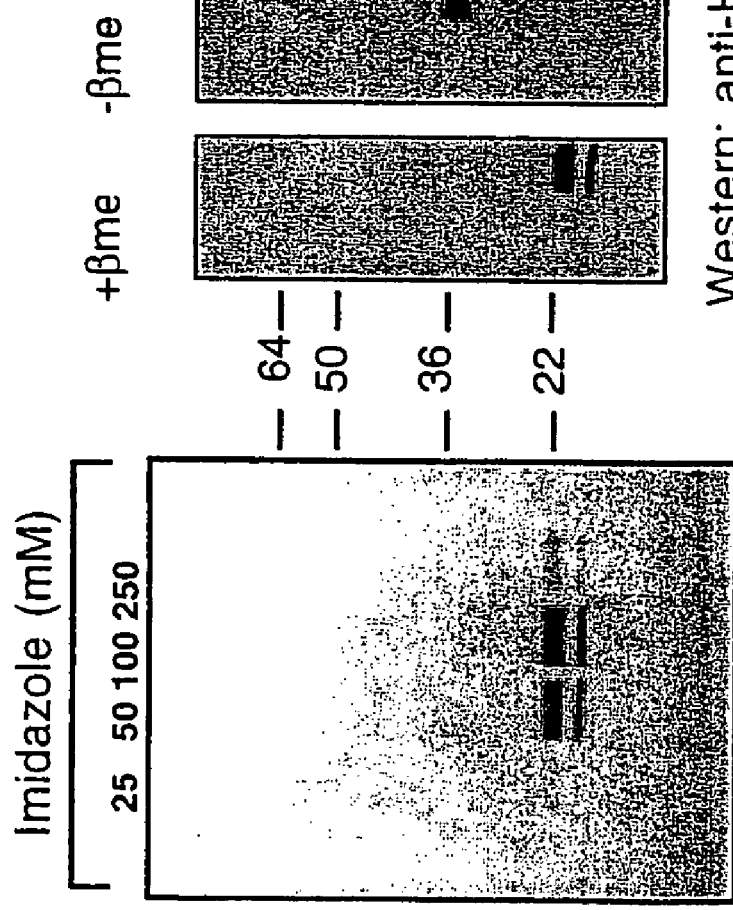
FIG. 5, comprising

Residues 58-185 of A33R were amplified by PCR and cloned into pVT-Bac (FIG. 5). The clone was co-transfected along with baculovirus DNA into Sf9 cells. Recombinant virus (Bac-A33Rt) was plaque purified and used to produce A33Rt protein. Sf9 cells were grown in suspension and infected with Bac-A33R for protein production. The protein was purified from the culture supernatant using nickel chromatography employing a step gradient of imidazole for elution.

Two closely migrating bands with molecular sizes of 18-22K were seen by silver stain following SDS-PAGE of the eluted protein under reducing conditions (FIG. 5A). The heterogeneity may be due to post-translational modification. A third faster-migrating and less intense band was also seen, which might be an underglycosylated (or non-glycosylated) form of the protein. This band could also lack the N-terminus of A33R. The bulk of the protein eluted in the 50 and 100 mM imidazole fractions. Fractions containing the purified protein were pooled, dialyzed and concentrated.

The protein was resolved on reducing and non-reducing SDS-gels and western blots were probed with anti-his antibody (FIG. 5B). Electrophoresis was carried out under reducing conditions, the protein migrated at 22K. Under non-reducing conditions, the protein migrated at a position corresponding to 36K. Thus, the protein produced in the baculovirus system is dimeric as reported for the full length protein synthesized in VV infected cells (Roper et al., 1996, J. Virol. 70:3753-3762). A33Rt have also been analyzed. On average, the yield was 10 mg/L from infected Sf9 cells giving 4.5 mg of purified A33Rt. The protein reacts with a polyclonal antiserum prepared against VV infected cells and the reactivity of this protein was tested with MAbs to A33R such as IG10 (Hooper et al., 2000, Virology. 266:329-39).

Using this protein, a phage display library is screened, and conventional mouse monoclonal and polyclonal reagents are produced by methods known in the art and methods disclosed elsewhere herein.

B5Rt

Figure 6:
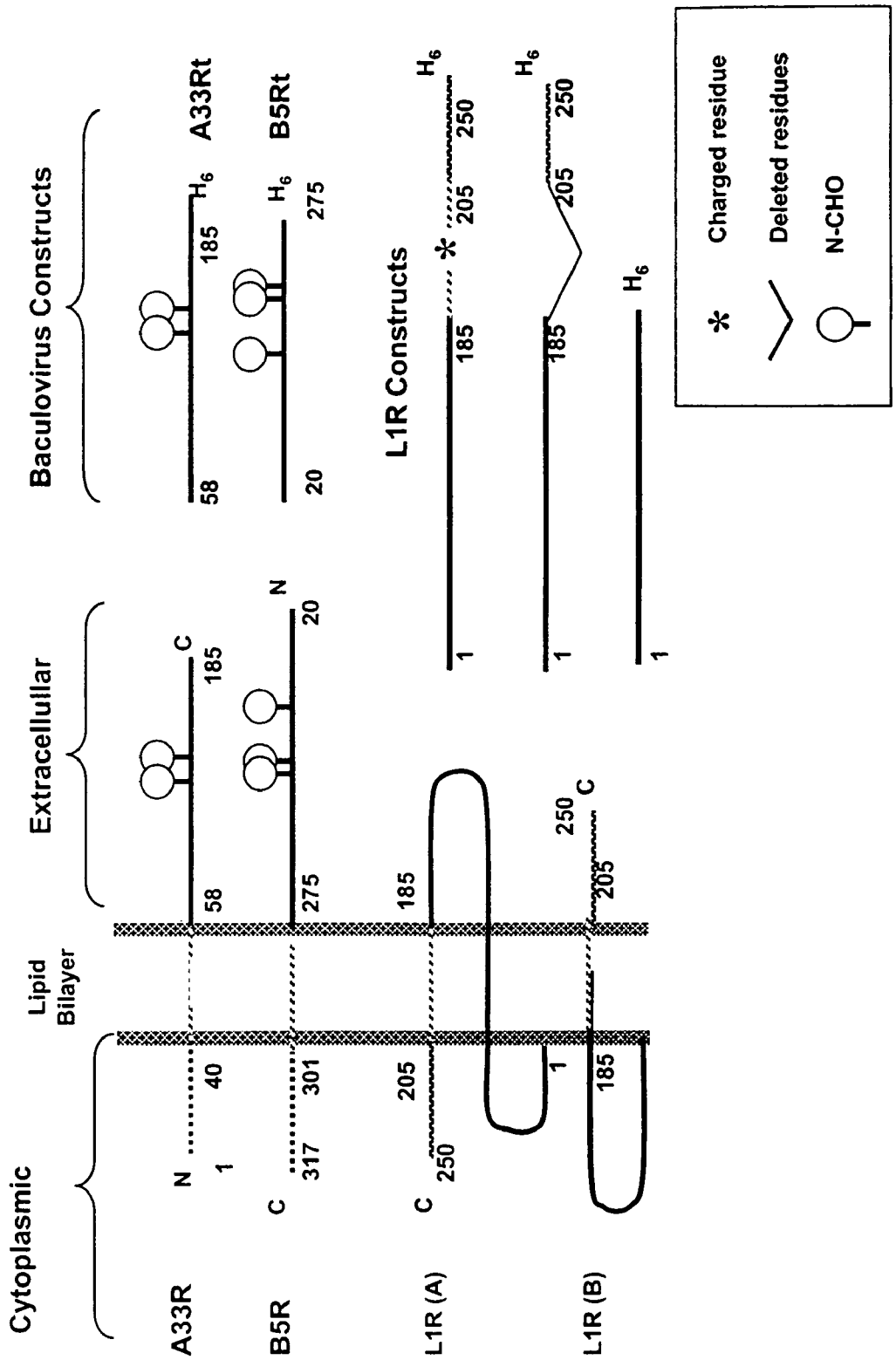
FIG. 6 is a diagram illustrating, without wishing to be bound by any particular theory, a schematic of A33R, B5R and L1R of *vaccinia* virus. L1R is shown in two possible orientations: L1R(A) and L1R(B).
Figure 7A:
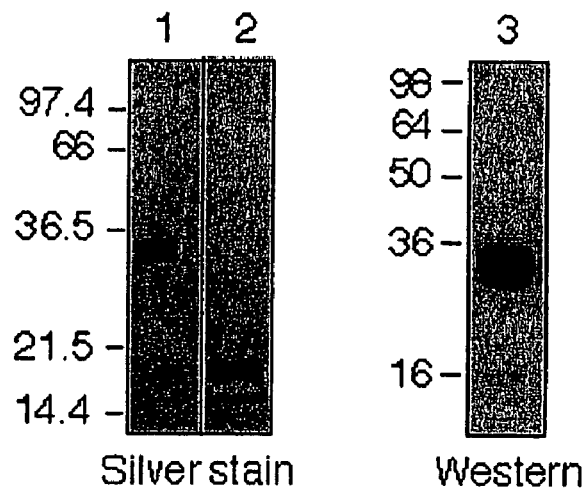
FIGS. 7A-7C, depicts images of Western blot and Silver stain analysis of *vaccinia* proteins expressed in baculovirus.
Figure 7B:
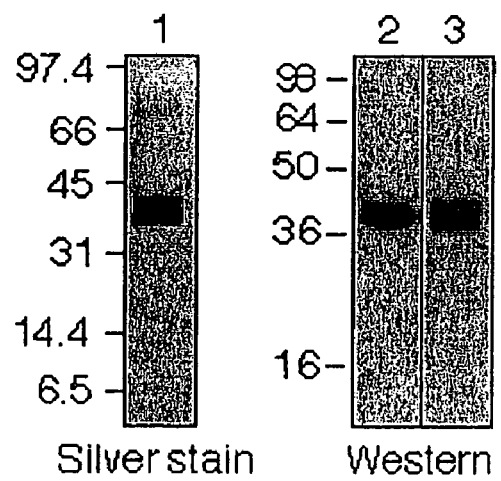
Figure 7C:
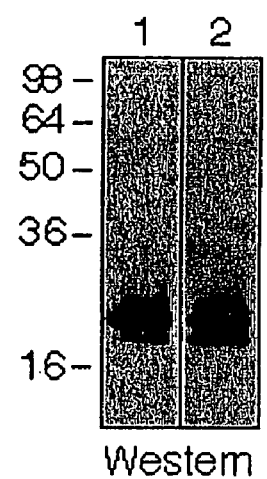
Figure 11B:
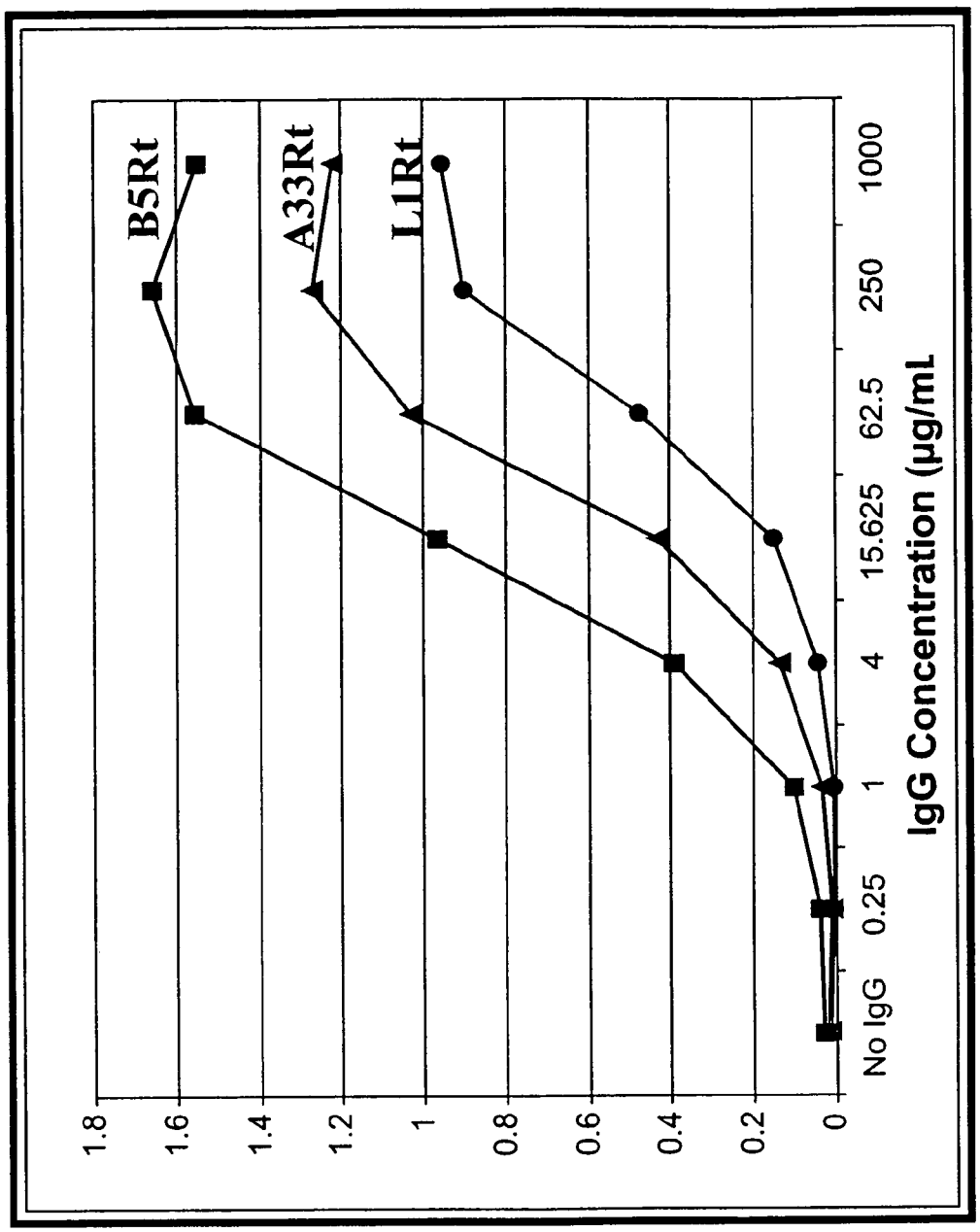
FIGS. 11A and 11B, depicts VIG reacting with recombinant *vaccinia* proteins B5Rt, A33Rt and L1R(185t).
Figure 11A:
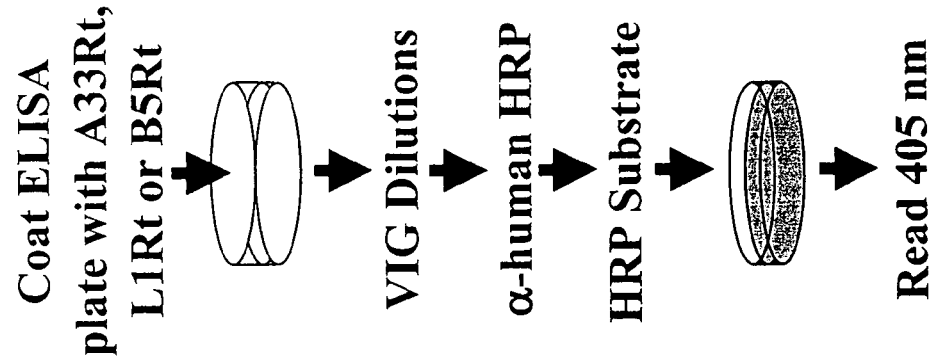
Figure 12:
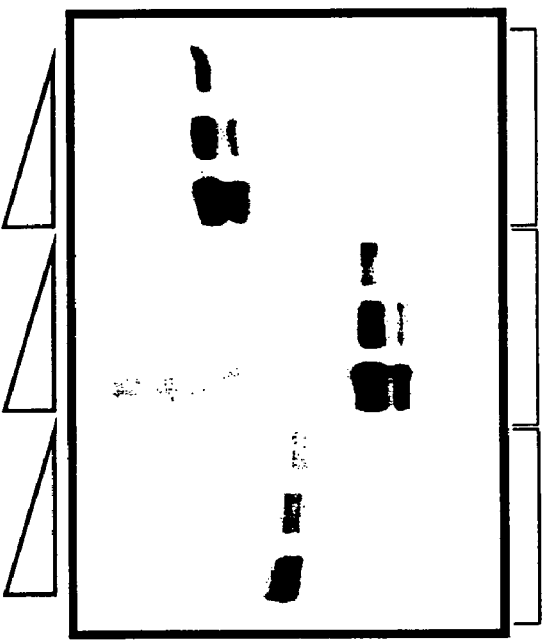
FIG. 12 is an image depicting a Western blot analysis of VIG reacting with recombinant *vaccinia* proteins B5Rt, A33Rt and L1R(185t).
Figure 13B:
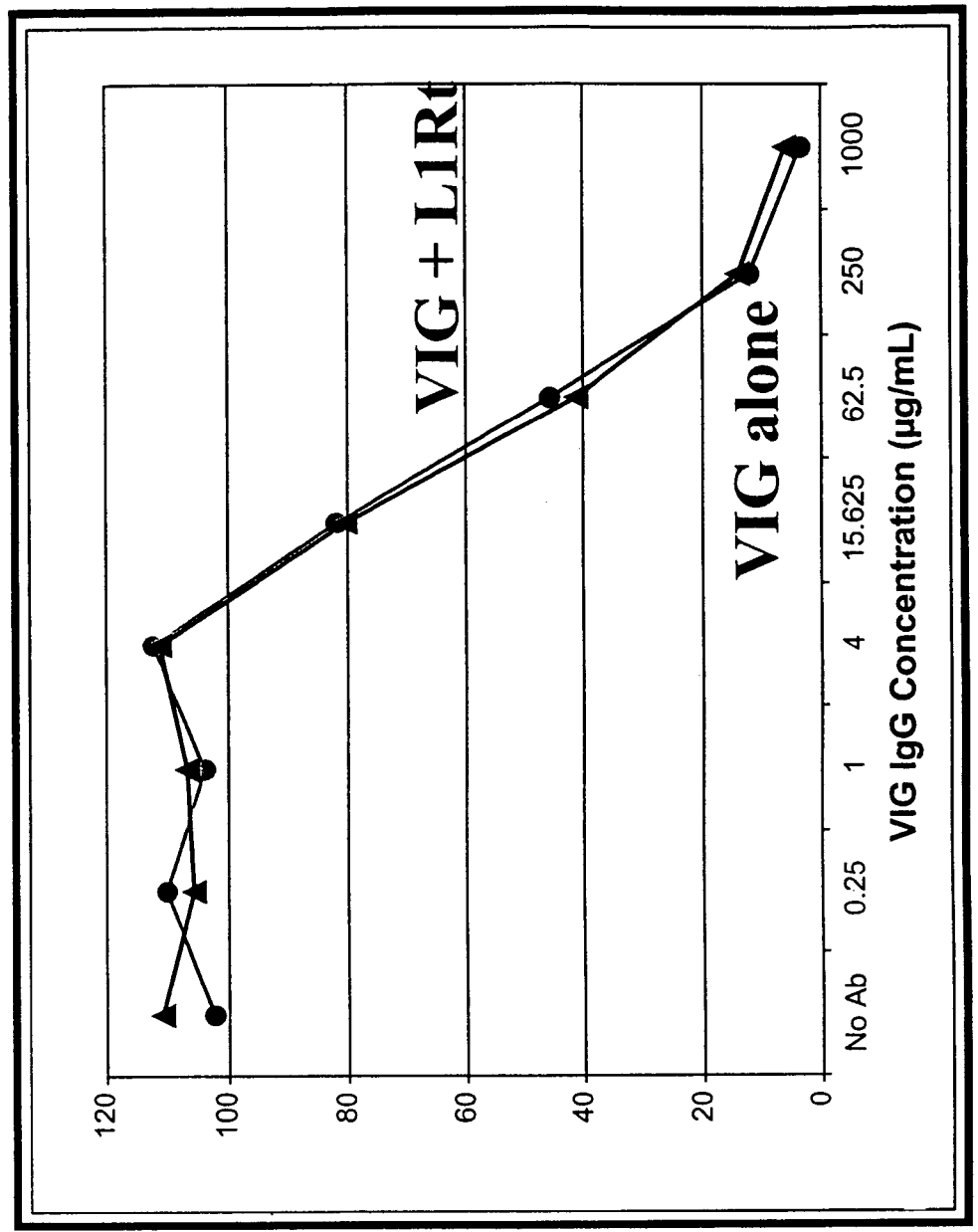
FIG. 13B is a graph demonstrating the results from the plaque reduction assay.
Figure 13A:
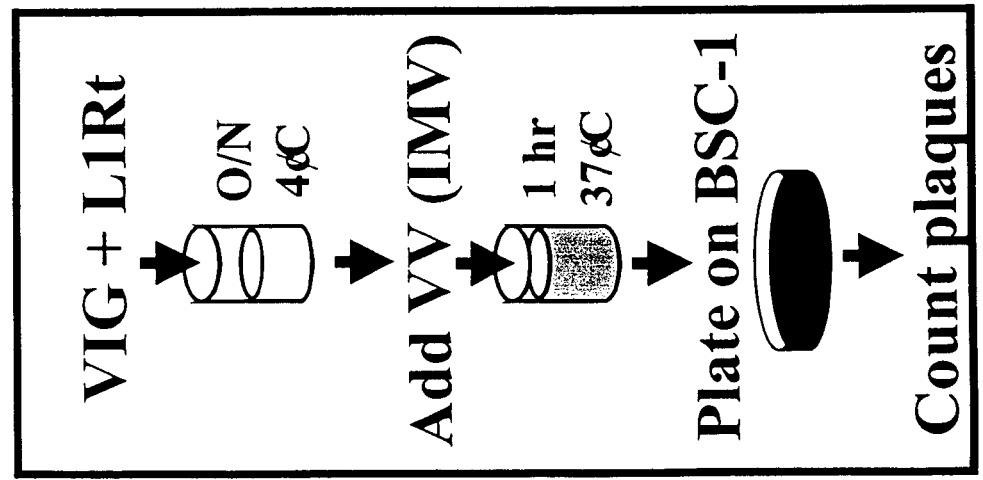
FIG. 13A is a diagram depicting a strategy for testing VIG in a plaque reduction assay.
Figure 14B:
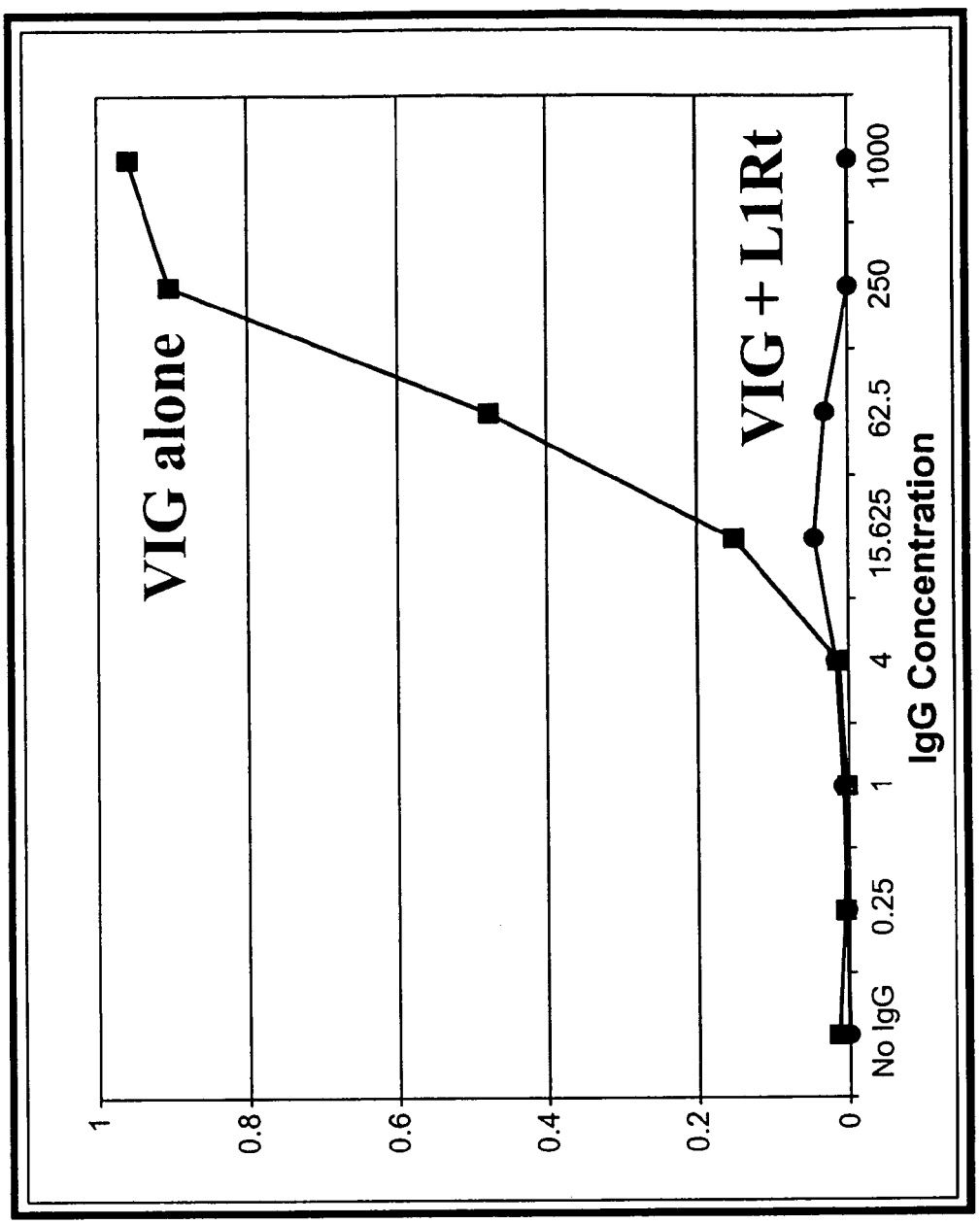
FIG. 14B is a graph depicting the results from the ELISA.
Figure 14A:
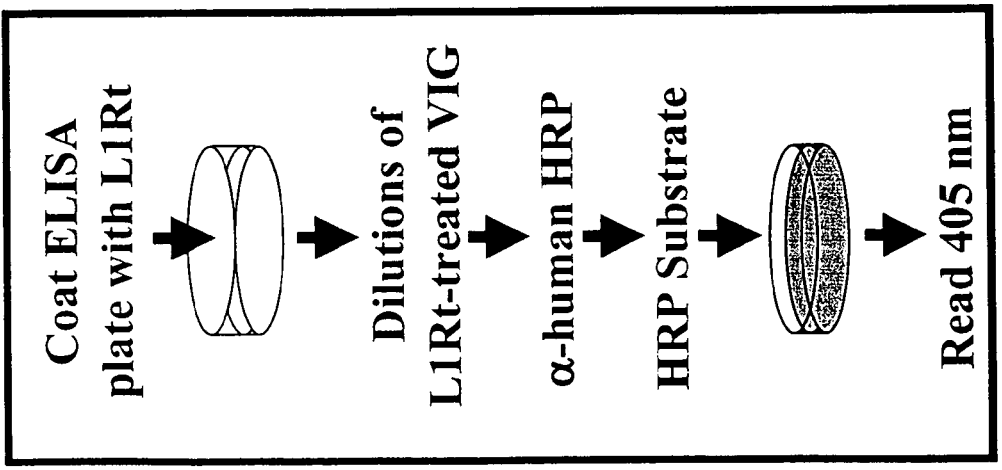
FIG. 14A is a diagram depicting an ELISA strategy using L1Rt to treat VIG.
Figure 15B:
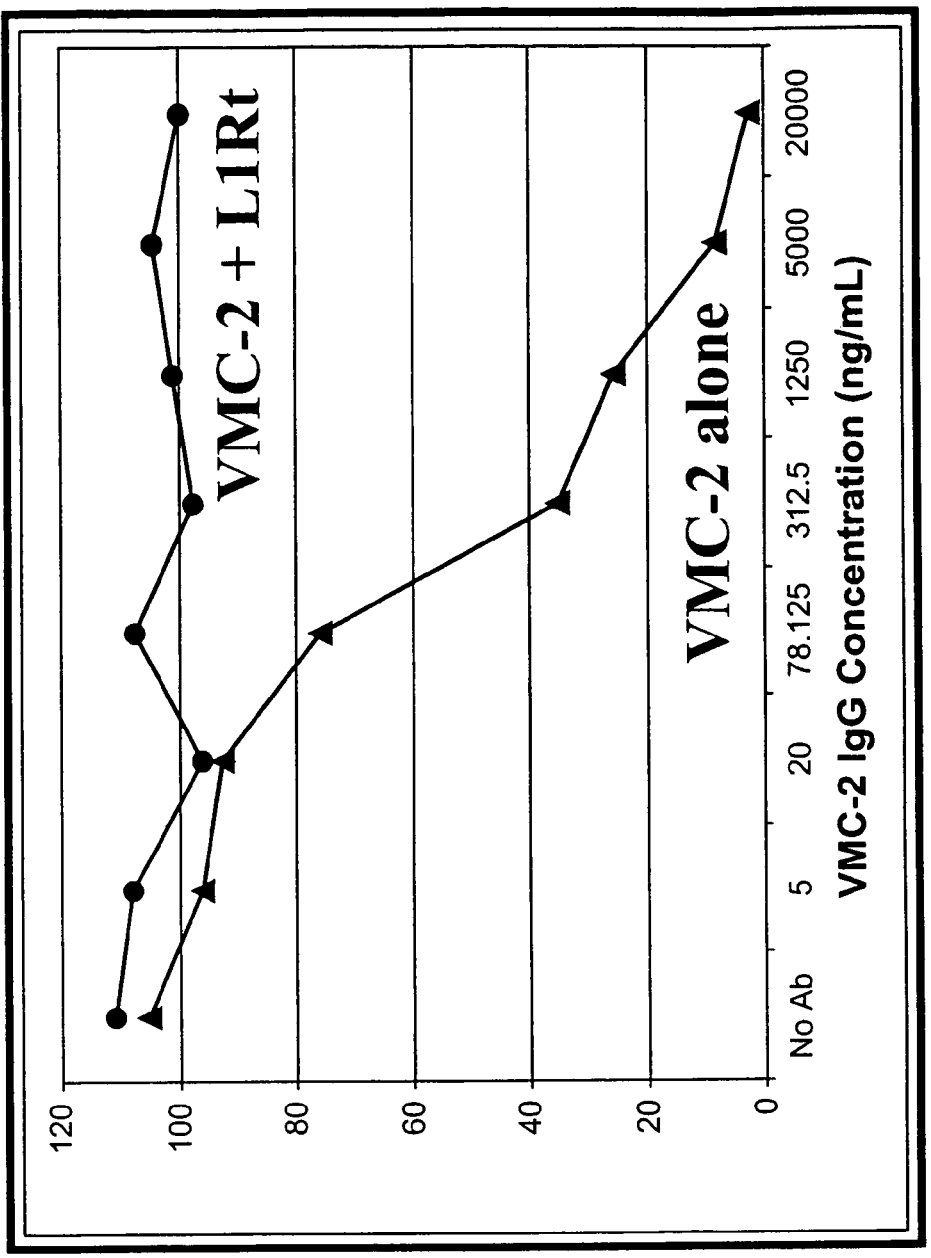
FIG. 15B is a graph depicting the results from the ELISA.
Figure 15A:
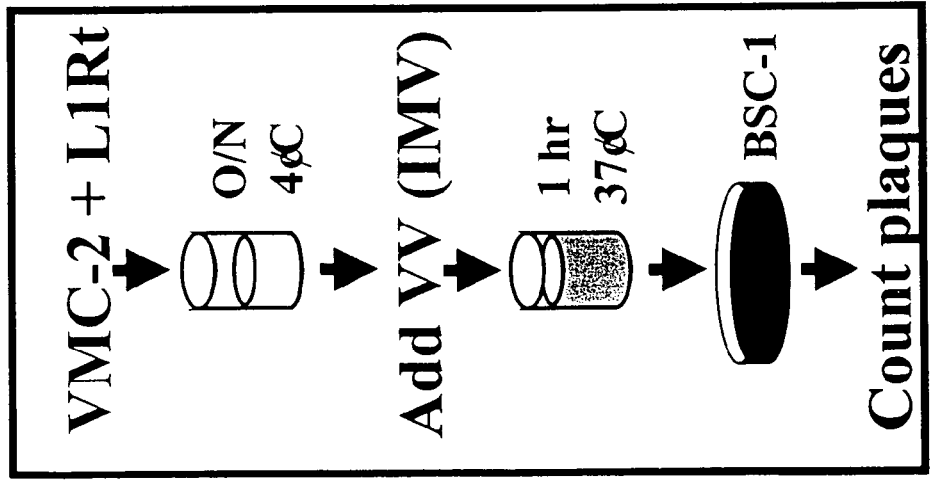
FIG. 15A is a diagram depicting a strategy behind the plaque formation assay using L1R(185t) to treat VMC-2.
Figure 16:
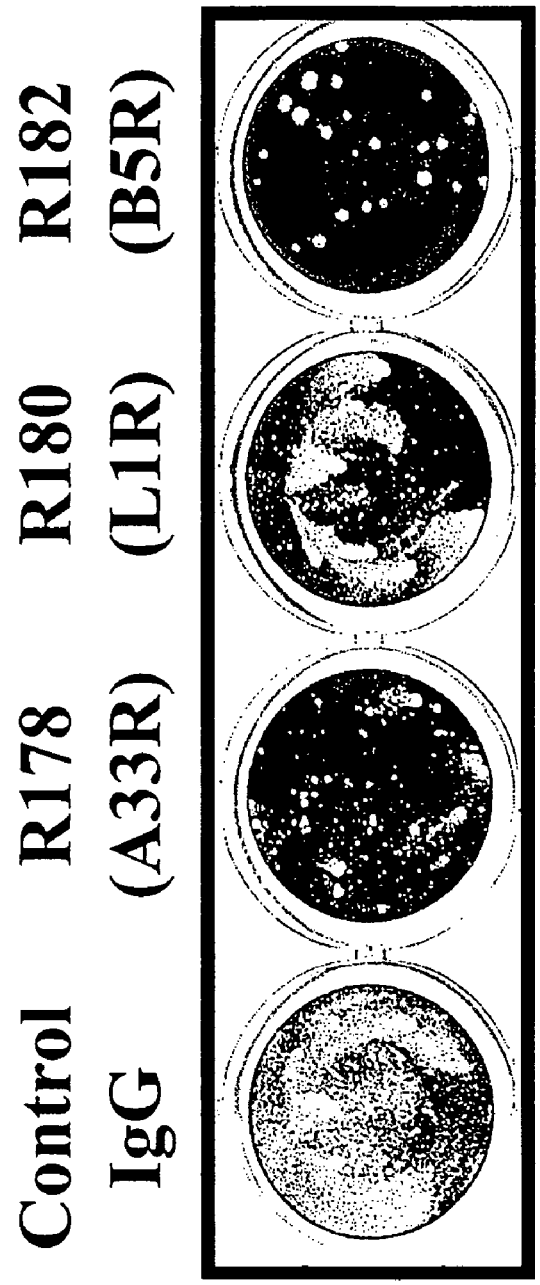
FIG. 16 depicts a series of images comparing comet inhibition by rabbit polyclonal IgG directed to recombinant truncated *vaccinia* proteins. R178 (vs. A33Rt) was observed to reduce VV comet formation indicating that this antibody inhibited spread of EEV. As expected R180 (vs. L1R(185t)) was observed to have no effect on VV plaque formation as these types of plaques require the EEV form of VV. R182 (vs. B5Rt) was observed to abrogate comet formation. When certain strains of VV are plated on cells, the plaques take on a "comet like" appearance indicative of cell-to-cell spread of EEV. Antibodies that inhibit comet formation are inhibiting EEV spread. Without wishing to be bound by any particular theory, antibodies that inhibit comet formation are likely providing a neutralization-like effect such that the free EEV released from a cell cannot infect the next cell.

B5R is a 42-kDa glycosylated type I membrane protein present on EEV but not IMV (Engelstad et al., 1992, Virology. 188:801-8 10; Engelstad et al., 1993, Virology. 194:627-637; Isaacs et al., 1992, J. Virol. 66:7217-7224; Martinez-Pomares, et al., 1993, J. Virol. 67:5450-5462). The strategy is similar to that which was used for expression of A33Rt in the baculovirus system as described elsewhere herein. The ectodomain corresponding to residues 20-275 was expressed in baculovirus (FIG. 6). Bac-B5R was cloned and isolated as described elsewhere herein. Bac-B5R can be cloned using a similar strategy to the strategy used in the cloning of Bac-A33R, thereby the expressed B5R recombinant protein can be secreted from baculovirus-infected cells. The protein purified from VV infected cells can be glycosylated and form intramolecular disulfide bonds (Isaacs et al., 1992, J. Virol. 66:7217-

7224). In addition, this protein can be oligomeric, and the oligomers may not be stabilized by disulfide bonds (Isaacs et al., 1992, J. Virol. 66:7217-7224).

The amino acid sequence of full-length *vaccinia* B5R is set forth in SEQ ID NO: 41 and is compared in FIG. 38C with the amino acid sequence of *variola* homologue thereof, termed B6R (SEQ ID NO:42), demonstrating about 92.7% identity. Further, the aa sequence of then truncated form of B5Rt is set forth in SEQ ID NO:5 (shown in FIG. 38A) and the nucleotide sequence of a nucleic acid encoding B5Rt is set forth in SEQ ID NO:6 (depicted in FIG. 38B). A predicted truncated *variola* homolog of *vaccinia* B5Rt, termed B6Rt, is depicted in FIG. 38D, and has an aa sequence set forth in SEQ ID NO:43. The truncated B5Rt and B6Rt homologs were compared demonstrating an amino acid sequence identity of about 91.8% (FIG. 38E).

L1R and F9L

L1R and F9L are both IMV proteins that are disulfide bonded by a VV specific pathway and described previously (Senkevich et al., 2000, Proc. Natl. Acad. Sci. U.S.A. 97:12068-12037; White et al., 2002, J. Virol. 76:467-472). L1R (and possibly F9L) stimulate high titers of virus neutralizing antibodies directed, presumably, at the IMV form of the virus, suggesting that L1R (and/or F9L) may interact with an IMV-specific cell receptor. Furthermore, administration of L1R(185t) to mice or antibodies made to L1R(185t) protected them against disease. Initial attempts to block infection with L1R(185t) have not succeeded, but this could be due to affinity, for example, it takes a high concentration of soluble gD to block infection by HSV (Nicola et al., 1996, 15th Annual Meeting, American Society for Virology, London, Ontario, Canada) due to the low affinity of gD for its cellular receptors HveA and nectin-1 (Krummenacher et al., 1999, J. Virol. 73:8127-8137; Willis et al., 1998, J. Virol. 72:5937-5947). Similar blocking studies can be performed with each of the IMV proteins. If one of these proteins does block infection, it indicates that the protein is a receptor binding protein of the IMV.

Figure 3:
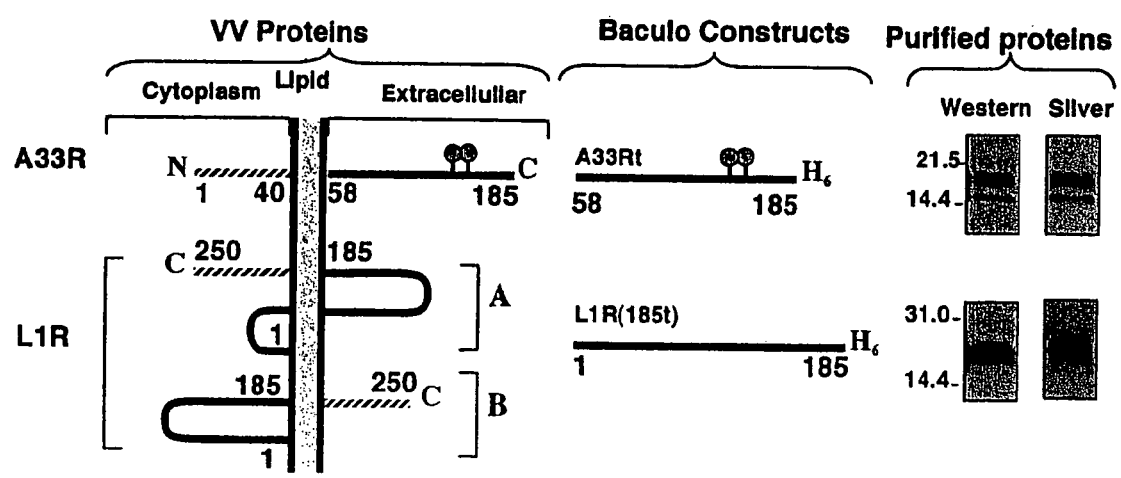
FIG. 3 is a diagram illustrating, without wishing to be bound by any particular theory, A33R as a type II membrane glycoprotein (anchored in the membrane by its N-terminus).

L1R is an essential myristoylated protein of 250 amino acids that is associated with the IMV membrane (Ravanello et al., 1994, J. Gen. Virol. 75:1479-83) (FIG. 3). L1R may play a role in IMV attachment and/or penetration (Franke et al., 1990, J. Virol. 64:5988-96; Ichihashi et al., 1996, Virology. 220:491-494; Ichihashi et al., 1994, Virology. 202:834-843; Ravanello et al., 1993, J. Biol. Chem. 268:7585-93; Wolfe et al., 1995, Virology. 211:53-63). L1R has one near C-terminal hydrophobic stretch of amino acids (residues 186-204) that are predicted to serve as a membrane anchor. The presence of myristic acid on glycine 2 (Franke et al., 1990, J. Virol. 64:5988-96; Wolfe et al., 1995, Virology. 211:53-63) suggests that a portion of the N-terminus may be intracellular (and on the inside of the IMV envelope). On the other hand, all of the cysteine residues of the protein, as well as predicted sites for N-glycosylation, are in the N-terminal portion of L1R and the protein is known to be disulfide bonded wherein the intramolecular disulfide bonds are formed by a poxvirus-encoded cytoplasmic redox system (Wolfe et al., 1995, Virology. 211:53-63; Senkevich et al., 2000, Proc. Natl. Acad. Sci. USA 97:12068-12073). Prior to the instant invention, the art was uncertain about the precise topology of L1R in the IMV envelope. Without wishing to be bound by any particular theory, Applicants, against the prevalent theory in the art, postulated that this region of L1R can be on the outside of the IMV envelope. Once possible model that incorporates all the available data is depicted in FIG. 3 (L1R "A"). The "A" model of L1R conformation requires that the protein make two passes through the viral membrane, which is not predicted to occur from hydropathy analysis of the L1R sequence. Another model, shown as "B" for L1R in FIG. 3, predicts that much of the N-terminus can be inside the virus particle and disulfide bonds can be formed in cytoplasmic compartments directed by VV proteins. Evidence in favor of this alternative has been documented to involve the participation of another VV protein, ELOR (Senkevich et al., 2000, Proc. Natl. Acad. Sci. USA 97:12068-12037; White et al., 2002, J. Virol. 76:467-472). This would position much of the N-terminus on the cytoplasmic face so that amino acids 186-204 traverses the membrane. Therefore, it is expected that only the C-terminal 46 amino acids would be on the extracellular (or outer IMV) face (FIG. 3, L1R "B"). This novel hypothesis, which contravened the teachings in the art, combined with another novel theory that the normal pathway by which this protein is folded in and disulfide bonded in VV infected cells can be bypassed by placing the coding sequence devoid of the putative cytoplasmic 186-204 and in frame with the melittin signal peptide, resulted in the successful excretion, for the first time, of this truncated protein from insect cells using a baculovirus expression system. Without wishing to be bound by any particular theory, this may direct the protein to the normal ER-Golgi pathway of the insect cells.

To enhance the probability of obtaining a secreted protein that had biologic activity (i.e., which stimulated IMV neutralizing antibody), several different potential L1R baculovirus constructs were considered (FIG. 6). A goal of each construct design possibility was to obtain a form of L1R that represented all of the possible immunogenic sequences. First, the entire L1R ORF can be modified such that 3 charged amino acid residues would inserted within the predicted TMR (residues 186-204). It has been demonstrated previously that a similar modification of HSV gD causes it to be secreted (Chiang et al., 1994, J. Virol. 68:2529-2543). From this construct, the entire L1R protein can be obtained as a secreted protein. To address the possibility that such a protein could not be efficiently secreted, a recombinant that expressed a form of L1R lacking residues 186-204 can be produced. Further, a form of L1R comprising residues 1-185, i.e., L1Rt (185), was produced. Theoretically, and without wishing to be bound by any particular theory, it is likely that none of these three constructs is myristoylated, since the protein would be directed to the secretory pathway of the infected insect cells. Moreover, cloning it into baculovirus added extra amino acids which would preclude myristolyation. Finally, assuming that model L1R(B) is correct (FIGS. 3 and 6), a fragment mimicking amino acids 205-250 can be synthesized.

Residues 1-185 of L1R were cloned as a baculovirus recombinant (FIG. 3) and then used to prepare polyclonal antiserum. If this fragment contained the important immunologic epitopes, it should stimulate IMV neutralizing antibody production, and, indeed, the data disclosed herein demonstrate that this fragment did indeed stimulate such an antibody response and that the resulting antibody recognized authentic L1R in VV infected cells.

The amino acid sequence of full-length *vaccinia* L1R is set forth in SEQ ID NO: 38 and is compared in FIG. 37C with the amino acid sequence of *variola* homologue thereof, termed M1R (SEQ ID NO:39), demonstrating about 99.2% identity. Further, the aa sequence of a truncated form of L1R(185t) is set forth in SEQ ID NO:1 (shown in FIG. 33A) and the nucleotide sequence of a nucleic acid encoding L1R(185t) is set forth in SEQ ID NO:2 (depicted in FIG. 33B). A predicted truncated *variola* homolog of *vaccinia* L1R(185t), termed M1Rt, is depicted in FIG. 37D, and has an aa sequence set forth in SEQ ID NO:40.

Peptides mimicking amino acids 205-250 can be generated synthetically because it is not practical to express residues 205-250 using the baculovirus system since the small size of the resulting protein would make purification and detection difficult. Antibodies against L1R residues 205-250 can be generated by immunizing animals with the synthetic peptide conjugated to KLH.

The recombinant proteins secreted from the infected insect cells can be used to prepare monoclonal and polyclonal antibodies and to screen the phage library. Further, the expressed proteins may react with one or more of the existing anti-L1R MAbs, such as, 7D11, 10F5 (Hooper et al., 2000, Virology. 266:329-39) and 2D5 (Ichihashi et al., 1996, Virology. 220: 491-494). These known MAbs are used to compare the MAbs that are disclosed elsewhere herein developed by the methods described in the present disclosure. These baculovirus constructs and antibodies can also be used to study the orientation of L1R in membranes of VV infected cells.

A27L and A17L

These proteins form a stable hetero-oligomeric complex in the virion and in VV infected cells as described by Rodriguez et al. (1993, J. Virol. 67:3435-3440). A27L is a 14 kDa protein comprising a heparin binding domain, a putative fusion domain and a region that interacts with A17L (Vazquez et al., 1998, J. Virol. Methods. 72:10126-10137). The structure of A27L was recently solved by NMR (Lin et al., 2002, J. Biol. Chem. 277:20949-20959). A MAb to A27L neutralized VV and protects passively immunized mice against a lethal challenge with VV (Ramirez et al., 2002, J. Gen. Virol. 83:1059-67). A17L may be important for virus morphogenesis (Rodriguez et al., 1995, J. Virol. 69:4640-4648). A27L has no transmembrane region (TMR) and is held in the membrane by association with A17L. A17L has several hydrophobic segments at the N and C termini and there is evidence that the protein forms a "horseshoe" configuration, being anchored in the membranes at both ends (Betakova et al., 1999, Virology. 261:347-356).

An analogous situation is found for the herpesviruses, where highly conserved glycoproteins gH and gL form a stable non-covalently linked heterodimer (Hutchinson et al., 1992, J. Virol. 66:2240-2250). In case of herpesvirus, gL has no TMR and gH is thought to be the fusion protein. However, gH processing and transport requires complex formation with gL (Dubin et al., 1995, J. Virol. 69:4564-4568; Hutchinson et al., 1992, J. Virol. 66:2240-2250; Peng et al., 1998, J. Virol. 72:6092-6103). A secreted form of the complex (removing the TMR and carboxyl terminus of gH) demonstrated that the complex, but not the individual glycoproteins, stimulated virus neutralizing antibody and protected mice from zosteriform spread of HSV (Peng et al., 1998, J. Virol. 72:65-72; Peng et al., 1998, J. Virol. 72:6092-6103).

Baculovirus recombinants for A27L (full length) and A17L (truncated to residues 80-138 to eliminate the two large hydrophobic anchors) are separated. It can be readily assessed whether insect cells co-infected with the two baculovirus recombinants produce a secreted form of the complex. The immunogenicity and protective ability of the complex compared with that of A27L alone is assessed to determine whether the complex is more protective an immunogen than either protein alone. The protein complex is assessed to determine inhibition of virus entry and/or cell spread.

Purification and Characterization of the Baculovirus Expressed Proteins

Sufficient quantities of each protein can be purified for obtaining antibodies using nickel chromatography. In general, this procedure works well, but immunoaffinity chromatography is more amenable for obtaining larger quantities of protein. The MAbs of the present invention are suitable as immunosorbents. MAbs are used under several elution methods (low pH, high pH or chaotropic agents) for each protein to test for specificity. The MAb with the most specificity can be used for protein purification. For A33Rt, nickel chromatography worked well resulting in large quantities of highly purified protein with a step gradient elution procedure. For L1R, 7D11 IgG can be used to purify L1R recombinant protein. 7D11 IgG can be used for purifying the full length constructs, but the 1-185 construct might be lacking the 7D11 epitope.

Figure 4:
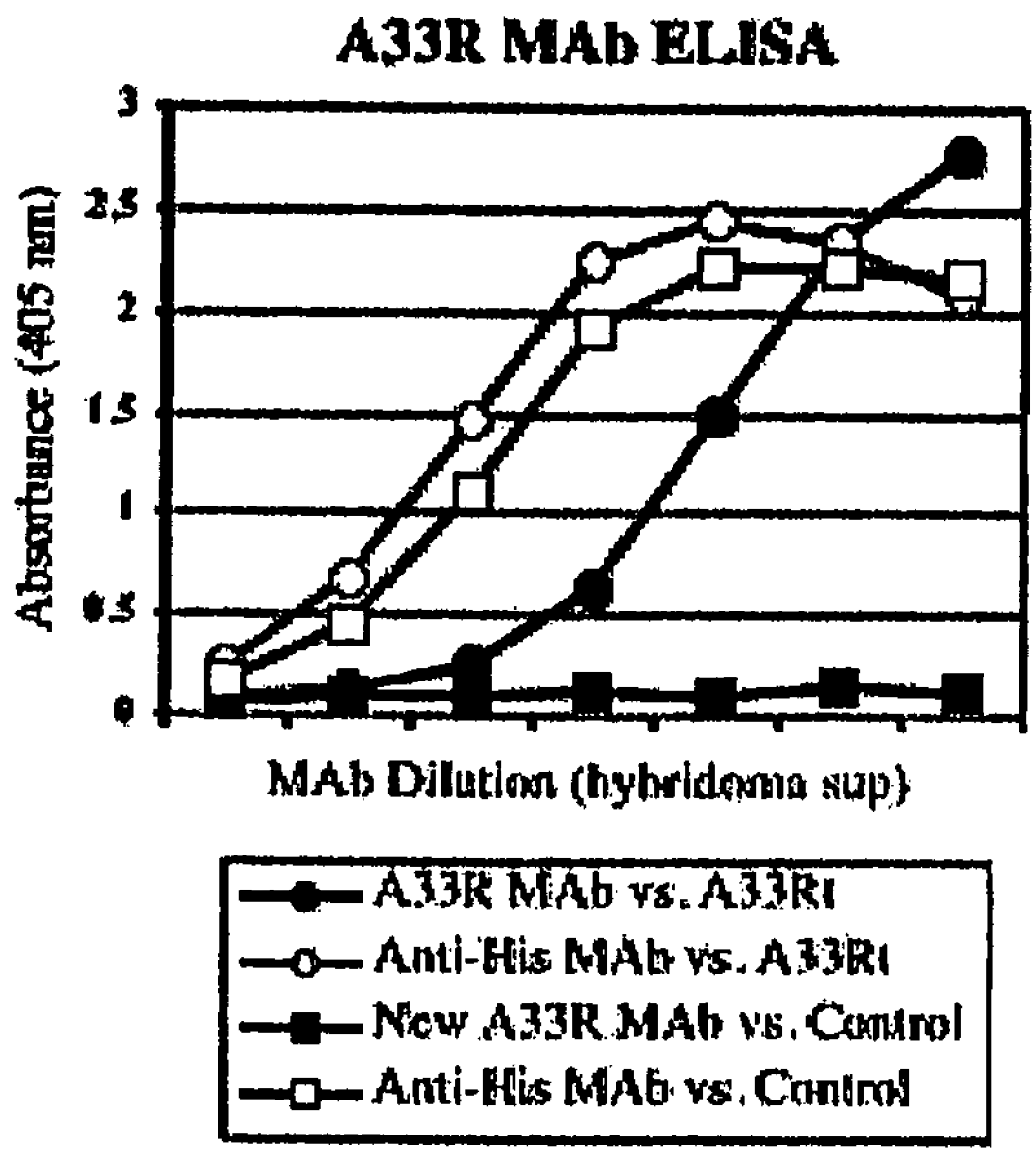
FIG. 4 is a graph depicting the ability of the A33R monoclonal antibody to specifically bind to a A33R epitope and the His tag as the A33R monoclonal antibody did not react with a control protein containing the His tag.

A33Rt and L1R(185t) as a Model for the Use of Baculovirus Expressed Proteins to Generate Antibodies Various VV proteins were purified from culture supernatant using nickel chromatography. Rabbits were immunized with each protein and neutralization titers were determined by a 50% plaque reduction method. Rabbits immunized with truncated A33 (A33Rt) protein had titers of 1:100. A rabbit immunized with a 185 aa residue fragment of L1R, designated L1R(185t) or simply "L1Rt", had a titer of 1:10,000. A monoclonal antibody (MAb) that specifically bound with A33Rt was produced and recognized the A33Rt baculovirus expressed protein by Western blotting as well as by ELISA (FIG. 4). These data demonstrate that the MAb recognized an A33R specific epitope and not the His tag. The MAb also recognized the full-length protein in VV infected cells. The ability of the A33 MAb to neutralize virus and to protect mice from VV challenge was evaluated using methods described elsewhere herein. The A33 MAb can also be used in subsequent purification of A33R. The ability of the A33 MAb to cross react with the *variola* A33R homologue is evaluated using methods described elsewhere herein. In summary, the data presented herein demonstrate that the purified baculovirus expressed forms of L1R(185t) and A33Rt are good mimics of the proteins expressed by VV.

Moreover, the properties of L1R(185t) and A33Rt, and the antibodies corresponding to each, can be used to determine the orientation of the VV protein in the membrane.

Generation of *Variola* Homologues of L1R and A33R

A subunit vaccine directed against *variola* virus can comprise *variola* proteins, *vaccinia* proteins, or combinations thereof. Although the VV proteins in Table 1 exhibit a high level of amino acid sequence identity with their *variola* homologues, there can be antigenic differences relevant to protection against disease. Accordingly, *variola* homologues of A33R and L1R are readily produced in the baculovirus system. For example, changes to the open reading frames (ORFs) of the *vaccinia* homologues using site directed mutagenesis (e.g., Quick Change Mutagenesis Kit, Stratagene) are generated.

This technique has been used to introduce numerous amino acid substitutions into the herpes simplex virus receptor HveA (Connolly et al., 2002, J. Virol. 76: 10894-904). A single nucleotide change is required to produce a *variola* homologue using *vaccinia* L1R. For A33R, nine amino acid substitutions and one deletion are introduced into the *vaccinia* ORF. Since some of the necessary changes are to adjacent residues, the entire mutagenesis of A33R is readily accomplished in seven steps. These modified ORFs are recombined into the baculovirus genome to generate constructs equivalent to those corresponding to *vaccinia* A33Rt and L1R(185t).

The extent of cross reactivity between *vaccinia* and *variola* proteins is assessed using currently available VIG. Antibodies to the *variola* proteins can also be generated by methods known in the art, for example, the recombinant protein can be used to immunize mice and the like.

VV Subunit Vaccine Protects Mice from VV Challenge

The efficacy of the proteins used alone and in combination to protect mice against VV challenge was assessed using, among others, methods known and/or those methods described elsewhere herein. Various combinations of proteins can be used in the subunit vaccine to protect humans against infection.

Mouse Model of VV Infection

Mice were immunized up to four times subcutaneously with 10 µg of L1R, A33R, B5R or a combination, at 3-week intervals. Adjuvants such as MPL and QS21 were used. The efficacy of the various proteins to protect mice in a *vaccinia* infection model were tested using methods described in, for example, Belyakov et al. (2003, Proc. Natl. Acad. Sci. USA 100:9458-9463). Briefly BALB/c mice were anesthetized and inoculated intranasally with $10^6$ to $2 \times 10^7$ PFUs of *vaccinia* virus WR strain. The mice were weighed daily and loss of weight was used as a sign of disease. Other methods such as described by Ramirez et al. (2002, J. Gen. Virol. 83:1059-67), can also be used. Briefly, mice infected intraperitoneally with $10^8$ PFU of virus, killed 6-8 week old BALB/c mice within 3 days. Animals are monitored for weight loss and survival and for viral titers in the spleen and ovaries (Ramirez et al., 2002, J. Gen. Virol. 83: 1059-67).

Enhancing the Protective Capacity of the Subunit Vaccine by Adding Immune Evasion Proteins The effects of supplementing immune evasion proteins have been addressed in the herpes simplex virus system. Glycoproteins gC and gE of HSV function as immune evasion molecules (Dubin et al., 1991, J. Virol. 65:7046-7050; Frank et al., 1989, J. Virol. 63:4479-4488; Friedman et al., 1984, Nature. 309:633-635; Fries et al., 1986, J. Immunol. 137:1636-1641; Kostavasili et al., 1997, J. Immunol. 158: 1763-1771). More particularly, gC interacts with complement component C3b, and gE functions as an Fc receptor. Experiments were designed to blocking immune evasion domains on these HSV glycoproteins. gD is a human subunit vaccine that protects animals against HSV challenge (Long et al., 1984, Infect. Immun. 37:761-764). The addition of gC to the vaccine induced antibodies that bound with gC and allowed for C3b to function and adding gE allowed the full complement of anti-HSV antibodies to function to block infection.

VV, like HSV comprises a large number of proteins that can function in virus immune evasion. B8R is an IFNγ receptor homologue that is secreted from VV infected cells and blocks IFNγ activity by blocking its binding to cellular receptors (Alcami et al., 1995, Immunol. Today. 16:474-478; Alcami et al., 2002, J. Gen. Virol. 83:545-549; Alcami et al., 1995, J. Virol. 69:4633-4639; Alcami et al., 2000, J. Virol. Methods. 74:11230-11239). Unlike cellular IFN-γ receptors, the VV homologue has the ability to bind IFN-γ from a wide variety of species (Symons et al., 2002, J. Gen. Virol. 83:1953-1964). B18R is a soluble secreted IFN receptor homologue that protects VV infected cells from type 1 IFN (Symons et al., 1995, Cell. 81:551-560). In support of B18R having a role in virulence, it has been observed that a *vaccinia* virus mutant lacking the gene for B18R is attenuated in mice (Colamonici et al., 1995, J. Biol. Chem. 270:15974-15978; Symons et al., 1995, Cell. 81:551-560). Thus, antibodies which bind to B8R and B18R evasion domains can block their function and prevent or treat poxvirus infection.

B8R and B18R are expressed in baculovirus and are secreted into the cell medium. Mice are immunized with the purified proteins and antibodies are assessed for ability to attenuate virulence of a VV challenge, as described elsewhere herein. B8R or B18R immunogens can modify virulence of wild-type virus, but not of B8R and B18R null mutant, strains of VV (Alcami et al., 2000, J. Virol. Methods. 74:11230-11239; Symons et al., 2002, J. Gen. Virol. 83:1953-1964). These proteins can be combined with antigens designed to provoke a protective response, for example, but not limited to, L1R and A33R. Increasing doses of VV are applied to determine whether B8R and/or B18R synergize with protective immunogens, such as, but not limited to, L1R and A33R. A protein cocktail can also be used in a prime-boost regimen (i.e., prime with subunit vaccine protein(s) and boost with whole VV, or vice versa).

Example 2

Development of Therapeutic Antibodies for *Vaccinia* Virus

In response to the possible release of smallpox by bioterrorists, *vaccinia* virus (VV) vaccination of an at-risk population is an available prophylactic response. Efforts are now underway to produce large stocks of VV vaccine in cell culture. However, as pointed out previously elsewhere herein, mass immunization is limited by the grave risks of known complications, especially in immunocompromised hosts, pregnant women and infants. Such complications were treated using human immune globulin (VIG) obtained from VV-immunized people. The procedure of therapeutic passive immunization required administration of large volumes of VIG which, in turn, required vaccinating large numbers of vaccinees to obtain the VIG thereby exposing such vaccinees to the risks of the complications. Furthermore, little was known about which components of the immune globulin were effective, and there is uncertainty about the safety of its use. Thus, it is imperative to develop antibodies that can act therapeutically in the event that mass vaccination is required without the risk of having to immunize individuals to obtain the VIG.

To this end, a cocktail of defined and high affinity MAbs to VV proteins that can replace the use of traditional VIG (called VIG-R) in the event that mass VV vaccination is disclosed herein. The monoclonal antibodies recognize various VV envelope proteins known to elicit a neutralizing and/or protective response in a mouse model. A cocktail of such antibodies provides a uniform and secure source of a VV immune therapeutic reagent without the risks attendant in producing human VIG from vaccinated donors.

VV proteins L1R, A33R and B5R produced in a baculovirus expression system are used in the characterization of the mouse and rabbit antibodies corresponding to these proteins. Human monoclonal antibodies to L1R, A33R and B5R are produced using phage display and the ability of immune reagents thus produced against *vaccinia* proteins to protect mice from VV challenge is determined.

VV envelope proteins, such as, but not limited to, L1R, A33R and B5R are expressed in the baculovirus expression system to obtain multimilligram quantities of protein. The baculovirus expression system has been used to overexpress a number of herpes virus glycoproteins and cellular receptors (Carfi et al., 2001, Molecular Cell. 8:169-179; Connolly et al., 2001, Virology. 280:7-18; Geraghty et al., 1998, Science. 280:1618-1620; Krummenacher et al., 1998, J. Virol. 72:7064-7074; Krummenacher et al., 1999, J. Virol. 73:8127-8137; Milne et al., 2001, Virology. 281:315-328; Nicola et al., 1997, J. Virol. 71:2940-2946; Nicola et al., 1996, J. Virol. 70:3815-3822; Rux et al., 1998, J. Virol. 72:7091-7098; Sisk et al., 1994, J. Virol. 68:766-775; Whitbeck et al., 2001, J. Virol. 75:171-180; Willis et al., 1998, J. Virol. 72:5937-5947).

The proteins are used to prepare mouse monoclonal antibodies (MAbs) that are humanized (Co et al., 1991, Proc. Natl. Acad. Sci. USA. 88:2869-2873). The proteins are used to screen a combinatorial cDNA library of human antibody genes using phage display. The screen of a combinatorial cDNA library of human antibody genes using phage display has been used to identify a number of very interesting molecules, including a peptide that blocks the interaction between HSV glycoprotein gD and its receptor HveA (Sarrias et al., 1999, J. Virol. 73:5681-5687; Sarrias et al., 2000, Immunol. 37:665-673). The affinity/avidity of these antibodies is evaluated using Biosensor technology as has been used to examine the kinetics and affinity of binding of HSV glycoproteins to various cellular receptors (Canziani et al., 1999, Methods: A Companion to Methods in Enzymology 19:253-269; Krummenacher et al., 1999, J. Virol. 73:8127-8137; Rux et al., 2002, Virology 294:324-32; Rux et al., 1998, J. Virol. 72:7091-7098; Willis et al., 1998, J. Virol. 72:5937-5947). In addition to antibodies recognizing L1R, A33R and B5R, antibodies to other VV proteins, such as, but not limited to, A27L, H3L, D8L and A17L are generated.

The efficacy of the MAbs is assessed using passive protection in an art-recognized mouse of VV challenge (e.g., Ramirez et al., 2002, J. Gen. Virol. 83:1059-67). The efficacy of MAbs in VV challenge is assessed using mouse models of herpesvirus infection (Long et al., 1984, Infect. Immun. 37:761-764; Lubinski et al., 1999, Med. 190:1637-1646; Peng et al., 1998, J. Virol. 72:65-72).

The antibodies of the present invention are characterized for their role in VV infection. In the case of HSV, truncated gD blocks virus entry, whereas the truncated forms of gH/gL and gB do not (Peng et al., 1998, J. Virol. 72:65-72; Peng et al., 1998, J. Virol. 72:6092-6103; Whitbeck et al., 1997, J. Virol. 71:6083-6093). Blocking of infection by gD is due to competition of gDt with virion gD for binding to its cellular receptors. Although gHt/gL does not block infection, this protein complex does stimulate production of virus neutralizing antibody and protects mice (Peng et al., 1998, J. Virol. 72:65-72). gH/gL is required for fusion, and there is evidence that MAbs to gL block virus spread (Muggeridge et al., 2000, Virol.:2017-2027; Novotny et al., 1996, Virology. 221:1-13). Therefore, similar experiments with the baculovirus produced forms of A33R, B5R and L1R using a f3-galactosidase reporter can be used to measure VV entry in a similar fashion to the measurement of HSV entry as described in Peng et al. (1998, J. Virol. 72:65-72). B5R may neutralize and blocks EEV entry, whereas L1R may block IMV entry. A33R may not block virus entry, but it may block virus spread from cell to cell (Krummenacher et al., 1999, J. Virol. 73:8127-8137). Virus spread can be assayed by observing whether any of the constructs blocked comet formation by VV.

DNA vaccines comprising nucleic acids encoding L1R or A33R provoke a protective response in the mouse model (Hooper et al., 2000, Virology. 266:329-39). It was observed that antibodies to L1R and B5R have virus neutralizing capacity, and antibodies to A33R are non-neutralizing (Galmiche et al., 1999, Virology. 254:71-80). Passive immunization with MAbs to A33R are protective, even though these antibodies were non-neutralizing (Geraghty et al., 1998, Science. 280:1618-1620). A33R plays an important role in virus spread, thereby accounting for this peculiarity (Law et al., 2002, J. Gen. Virol. 83:209-222). The inability of a particular IMV or EEV protein to elicit neutralizing antibodies does not exclude it from consideration as the target of a successful therapeutic reagent. Ramirez et al (2002, J. Gen. Virol. 83:1059-67), demonstrated that a single MAb to A27L of IMV was able to neutralize virus infectivity and protect mice in passive immunization experiments. Therefore, antibodies to A27L and other candidates are included in the cocktail, such as, but not limited to, D8L H3L and A17L, L1R and A33R.

Full-length L1R and A33R have been demonstrated to have some efficacy as vaccine components in a mouse model (Hooper et al., 2000, Virology. 266:329-39). B5R has the ability to neutralize EEV infectivity and act as a prophylactic subunit vaccine (Galmiche et al., 1999, Virology. 254:71-80). The proteins and antibodies developed and disclosed elsewhere can be used for basic studies concerning the structure and function of these proteins and their roles in VV replication. The ability of expressed proteins to block infection or spread by EEV or IMV, demonstrating that the protein can interact with a cellular receptor for one of these forms of VV, is assessed as was performed in HSV (see, e.g., Ichihashi et al., 1996, Virology. 220:491-494; Law et al., 2002, J. Gen. Virol. 83:209-222; Lorenzo et al., 1998, Virology. 252:450-7; Wolfe et al., 1993, J. Virol. 67:4732-4741). Such studies led to the isolation and characterization of HSV receptors that interact with the viral glycoprotein gD (Carfi et al., 2001, Molecular Cell. 8:169-179; Geraghty et al., 1998, Science. 280:1618-1620; Johnson et al., 1990, J. Virol. 64:2569-2576; Krummenacher et al., 1998, J. Virol. 72:7064-7074; Montgomery et al., 1996, Cell. 87:427-436; Nicola et al., 1997, J. Virol. 71:2940-2946; Nicola et al., 1996, J. Virol. 70:3815-3822; Whitbeck et al., 1997, J. Virol. 71:6083-6093).

Use of Phage Display to Isolate Human Antibodies to *Vaccinia* Virus Proteins

A therapeutic cocktail (VIG-R) of MAbs recognizing, but not limited to, L1R(185t), A33Rt and B5Rt, is obtained by using the corresponding purified proteins to immunize mice, and isolating mouse hybridomas that secrete the appropriate MAbs. The antibodies are extensively characterized for neutralizing activity and/or ability to passively protect mice from virus challenge. Antibodies with high affinity can have high potency for therapeutic immunization. MAbs with neutralizing activity can show efficacy in passive immunization. However, non-neutralizing MAbs can also passively protect. Those MAbs that show passive protection in the mouse model are candidates for producing humanized MAbs (Co et al., 1991, Proc. Natl. Acad. Sci. USA. 88:2869-2873).

A therapeutic cocktail (VIG-R) of MAbs can also be identified by using a phage display to isolate human MAbs (Poul et al., 2000, J. Mol. Biol. 301:1149-1161; Sheets et al., 1998, Proc. Natl. Acad. Sci. USA 95:6157-6162). This is a novel method for developing therapeutic antibodies to VV. The purified proteins are used to screen a combinatorial library derived from lymphocytes of VV immunized individuals. This method eliminates the need to "humanize" mouse antibodies that have therapeutic properties. In addition, the screening procedure results in isolation of antibodies with high affinity for the desired antigen. Large libraries of antibodies are produced by cloning millions of distinct antibody genes from white blood cells of healthy or immunized individuals into bacteriophage M13. The antigen-binding regions of VH and VL genes are cloned and used to construct scFv (single chains of the variable regions of IgG) or Fab gene repertoires. A phage library is created by cloning these repertoires as fusion proteins with a minor coat protein of M13 bacteriophage (see, e.g., Poul et al., 2000, J. Mol. Biol. 301:1149-1161; Sheets et al., 1998, Proc. Natl. Acad. Sci. USA 95:6157-6162). Each resulting phage has a functional antibody protein on its surface and contains the gene encoding the antibody incorporated into the phage genome. Phage that specifically binds to the test protein, such as but not limited to L1R(185t), A33Rt or B5Rt, are separated from non-binding phage by "panning" wherein bound phage are isolated and non-binding phage are washed away.

Passive Immunization with MAbs

Human sera have been used for prophylaxis and therapy of infectious diseases for over 100 years. Human hyperimmune globulins (HHIGs) are available for the prevention or treatment of viral diseases including respiratory syncytial virus (RSV), cytomegalovirus, hepatitis B virus, rabies, varicella-zoster and *vaccinia* (Sawyer et al., 2000, Antiviral Res. 47:57-77). HHIGs are currently obtained from individuals that have either been immunized or exposed to the virus. Shortcomings include the variability of potency from batch to batch, availability of the products, and the risk of using contaminated human blood products.

Development of humanized and human MAbs raises the possibility of producing effective, uniform and safer products as an alternative for such products. Moreover, MAb-based reagents can target specific antigens known to provoke a protective immune response. For example, in RSV, Synagis™ is the first humanized MAb to be licensed in the U.S. for therapeutic use. This IgG1 antibody was humanized (95% human, 5% mouse) using recombinant DNA technology and is directed against a neutralizing epitope on the RSV F glycoprotein (Johnson et al., 1999, J. Infect. Dis. 180:35-40; Johnson et al., 1997, J. Infect. Dis. 176:1215-1224). Clinical trials (NIH) are also planned to test the efficacy of using a human MAb to HSV gD (Sanna et al., 1996, Virology. 215: 101-106) to prevent neonatal herpes in newborns exposed to genital HSV during labor and delivery. This MAb was derived by phage display (Burioni et al., 1994, Proc. Natl. Acad. Sci. USA. 91:355-359; De Logu et al., 1998, J. Clin. Microbiol. 36:3198-204). As a Group lb MAb (Muggeridge et al., 1990, In: Immunochemistry of viruses, vol. 11, pp. 459-481, Van Regenmortel &. Neurath, eds., Elsevier Biochemical Press, Amsterdam, The Netherlands), it has high viral neutralizing activity and members of this group of MAbs also block the binding of gD to both of its cellular receptors (Krummenacher et al., 1998, J. Virol. 72:7064-7074; Nicola et al., 1998, J. Virol. 72:3595-360; Whitbeck et al., 1997, J. Virol. 71:6083-6093). Based upon the present disclosure, an effective VIG-R contains MAbs critical to viral epitopes involved in attachment, entry, release and/or spread of VV.

Preparation of Rabbit and Mouse Antibodies

Antibodies can be generated by methods known in the art, for example the antibodies of the present invention can be generated using the procedures that have been described in the preparation of reagents for HSV glycoproteins and receptors (Krummenacher et al., 2000, J. Virol. 74:10863-1087; Whitbeck et al., 2001, J. Virol. 75:171-180). 2-5 mg of each purified protein or KLH-conjugated synthetic peptide are supplied to Cocalico Inc. for immunization in rabbits. The rabbit sera is a useful reagent for western blotting and combined immunoprecipitation-western blot experiments with MAbs. Some MAbs work well by ELISA or immunoprecipitation but not by western blotting. Hybridomas are produced by standard procedures set forth by the UPENN hybridoma center to immunize mice.

Human Monoclonal Antibodies to L1R, A33R and B5R Produced Using Phage Display

There are advantages for the use of phage display to produce human antibodies over the more traditional approach of humanizing mouse monoclonals. Direct isolation of human MAbs saves the steps involved in humanization. The MAb obtained from using phage display is fully human and the properties in terms of affinity and titer of the MAb is characterized.

Library Construction

Approximately 20-40 ml of peripheral blood are collected from 5 suitable donors. Random primed cDNA can be generated from lymphocytes derived from VV vaccinated donors (Welschof et al., 1995, J. Immunol. Methods. 179:203-2 14). The cDNA can be used as a template for PCR amplification of the VH and VL chain regions. A short synthetic linker sequence can be introduced between the heavy and light chains by splice overlap extension PCR and this can produce a single chain variable fragment (scFv) antibody, containing the VH and VL chains joined by a peptide linker (15 residues). Random pairing of heavy and light chains during scFv assembly can generate library diversity reflecting the number of unique members present within the library. To construct the phage library, a mixture of phagemid DNA (containing the gene for antibiotic resistance) and scFv DNA can be ligated, and the mixture is transformed into *E. coli*. Positive clones can be identified by plating on media containing the appropriate antibiotic.

Panning of the scFv-Phage Library

*Vaccinia* protein-binding phage can be isolated by "panning" against the purified baculovirus derived VV proteins including but not limited to A33Rt, L1R(185t) and B5Rt by using panning methods known in the art (Nicacio et al., 2002, J. Virol. 76:25 1-258; Sahu et al., 1996, J. Immunol. 157:884-891; Sarrias et al., 1999, J. Virol. 73:5681-5687). Briefly, microtiter wells are coated with A33Rt. The phage stock are divided into several pools and each pool are added to a separate well of the plate and incubated for 1 hr at 22° C. After washing, bound phage particles are eluted with glycine-HCl (pH 2.3). The bound phage from all of the wells are pooled together and amplified in *E. coli*. After three rounds of amplification, the bound and eluted phage are plated on a lawn of *E. coli*. To identify positives amongst the plaques, purified A33Rt is adsorbed to an ELISA plate and incubated with phage stocks from several plaque picks. Bound phage are detected using peroxidase-labeled anti-M13 antibody. DNA is extracted from positive phage stocks and subjected to dideoxy sequencing (Sanger et al., 1977, Proc. Natl. Acad. Sci. USA. 74:5463-5467). Infected cells are used to produce a soluble antibody preparation for each antigen-positive clone (Boyer et al., 1991, Clin. Exp. Immunol. 83:452-459).

MAb Production

Selected panned antibodies are converted to whole human antibodies (Boel et al., 2000, J. Immunol. Methods. 239:153-166). The M13 variable regions are cloned into vectors containing the constant regions of human IgG (Hieter et al., 1982, J. Biol. Chem. 257:1516-1522) (Kirsch et al., 1982, Science. 216:301-303). Briefly, the VL and VH genes encoding the scFv fragments are PCR-amplified using appropriate primers and then cloned in the pLEADER vector, which contains the T cell receptor leader peptide HAVT2O. The $V_L$ and $V_H$ genes fused with the leader peptide are cloned into the expression vectors (Palmiter et al., 1987, Cell. 50:435-443) that contain the sequences for the genomic κL chain (Hieter et al., 1982, J. Biol. Chem. 257:1516-1522) or γH chain C regions (Kirsch et al., 1982, Science. 216:301-303). The integrity of the constructs are assessed by transient transfection of COS cells. Supernatants from these cells are analyzed by ELISA for the presence of antibodies to various VV proteins (such as A33Rt). Stably transfected cell lines are established and used for production of human anti-VV-MAbs. IgG are purified using protein A-Sepharose affinity chromatography and structural integrity are assessed by SDS-PAGE and mass spectrometry. The ability of these antibodies to fix complement are assessed by ELISA (Aguado et al., 1985, J. Clin. Invest. 76:1418-1426).

Characterization of Monoclonal Antibodies

The antibodies (rabbit, mouse, and human) are tested against the appropriate proteins by immunoprecipitation, western blotting, ELISA, IFA and virus neutralization. In addition, the sera is tested against proteins expressed by VV infected cells, which confirms that the antibodies recognize the bona fide VV protein. A variety of methods known in the art can be used to assess epitope mapping of each protein. In formulating the VIG-R cocktail, competing MAbs may not be desired to be included within the same VIG-R cocktail. Thus epitope mapping, in addition to studies of other properties such as virus neutralization, provide valuable information regarding which epitopes of each protein are biologically important and useful for producing a VIG-R cocktail.

MAbs are characterized by methods known in the art and methods disclosed elsewhere herein. For example, MAbs are subdivided into two groups, those that recognize discontinuous epitopes and those that recognize continuous epitopes. MAbs that recognize continuous epitopes of VV proteins are further mapped using synthetic peptides, thereby subdividing these MAbs into smaller groups, each representing a specific epitope. Virus neutralization tests (plus or minus complement) can be used to distinguish these further. For example, two MAbs to gD of HSV recognize the same linear stretch of amino acids (Cohen et al., 1984, J. Virol. 49:102-10), yet one MAb is able to neutralize virus by interfering with receptor binding (Nicola et al., 1998, J. Virol. 72:3595-3601), whereas the other MAb possesses neither of these properties.

MAbs against discontinuous epitopes are mapped and grouped initially by competition studies. Optical biosensor analysis is an efficient method of carrying out these experiments (Krummenacher et al., 2000, J. Virol. 74:10863-10872). That is, the target protein is covalently coupled to a CM5 chip, then the first MAb is added. Once the biosensor signal due to binding of this antibody reaches a plateau (reflecting that this epitope is saturated), a second (test) MAb is added. If the two MAbs compete (i.e. recognize the same or overlapping epitopes) there will be no increase in biosensor signal. If they do not compete (i.e., recognize different epitopes), then this will be seen as an increase in signal. One skilled in the art can construct an antigenic map of the protein and a division of MAbs into epitope groups using the methods described herein as has been performed for B5Rt. The affinity of the MAbs for their respective VV proteins can also be analyzed using the optical biosensor. The results are used to for choose the most appropriate MAbs for a VIG-R cocktail. If there are two MAbs to the same, or overlapping, epitopes that differ only in affinity, one with highest affinity is selected for the cocktail. A similar strategy was used to determine affinities of HSV glycoproteins for their receptors and antibodies (Krummenacher et al., 2000, J. Virol. 74:10863-10872; Rux et al., 2002, Virology 394:324-32; Rux et al., 1998, J. Virol. 72:7091-7098, Willis et al., 1998, J. Virol. 72:5937-5947).

MAbs to discontinuous epitopes are further characterized for their ability to neutralize VV infectivity. For HSV, the MAbs to gD that neutralize virus infectivity inhibit receptor binding, whereas those directed against gH/gL inhibited virus-cell fusion and virus spread (Novotny et al., 1996, Virology. 221:1-13; Peng et al., 1998, J. Virol. 72:6092-6103). One skilled in the art, based upon the present disclosure would recognize that the MAbs for B5R and L1R are neutralizing antibodies, whereas antibodies for A33R may not neutralize. Thus, epitope mapping studies provide important information about the function of these proteins in VV infection and are important in selecting appropriate antibodies for preparing a VIG-R cocktail.

Example 3

Ability of Immune Reagents Against *Vaccinia* Proteins to Protect Mice from Challenge with *Vaccinia* Virus Passive immunotherapy with VIG can control untoward clinical disease progression in the human after VV vaccination. Efficacy of the various immune reagents to act therapeutically can be assessed as described Ramirez et al. (2002, J. Gen. Virol. 83:1059-67). Ramirez et al. teaches that sufficient virus given IP kills Balb/C mice within 3 days. MAb C3 directed against A27R protein was given just prior to (prophylactic regimen) or 1-3 days post-infection (therapeutic regimen) with a lethal dose of VV. Mice that were protected survived longer than 3 days, or completely recovered. This therapeutic can be used to determine the composition of VIG-R. WR strain of VV is used to determine the LD50. Mouse, rabbit and human antibodies to A33R, L1R and B5R are tested for their therapeutic capacity. Any mouse MAbs demonstrating efficacy, are candidates for humanization.

Testing of MAbs

MAbs recognizing L1R are known to neutralize virus and DNA vaccination with L1R (in combination with A33R) was able to protect animals (Hooper et al., 2000, Virology. 266: 329-39). Three MAbs to L1R with the following properties are identified: 1) each neutralizes virus infection by IMV; 2) they recognize different epitopes of L1R; and 3) each has high affinity for L1R. The first experiment is designed to determine the minimum dose of each MAb that affords the greatest protection in the therapeutic model. Each MAbs are tested over a 100-fold range of protein concentrations, using 5 mice per group and a total of 4 groups (0, 1, 10, 100 μg).

The three MAbs are used together, beginning with a mix that represents the minimum protective dose of each MAb determined in the first experiment. The antibodies are tested in three groups of animals (no MAb, full strength MAb mixture and a 1:10 dilution). The concentration of the mixture that works well is combined with similar mixtures representing different epitopes of the other two proteins. The cocktail can contain, preferably 9 to 10 MAbs. A final mouse VIG-R should represent more rather than fewer protein and epitope targets. Preferably, a greater complexity is desired because the human VIG-R can be administered to an "outbred" human population. Selected mouse MAbs are candidates for humanization. Similar experiments are conducted with the human MAbs. In the event that both mouse and human MAbs are to the same or overlapping epitopes for example L1R, then the two MAbs are compared for efficacy.

A similar strategy of choosing MAbs to B5R for the VIG-R mixture is employed since this protein induces neutralizing antibody to EEV. A33R may not stimulate neutralizing antibodies. However, a similar situation was reported for the gH/gL complex of HSV (Browne et al., 1993, J. Gen. Virol. 74:28 13-7; Forrester et al., 1991, Journal of General Virology. 72:369-75). Although gH/gL plays an essential role in virus penetration (Browne et al., 2001, J. Gen. Virol. 82:1419-1422; Muggeridge et al., 2000, Virol.:2017-2027; Pertel et al., 2001, Virology. 279:313-324; Turner et al., 1998, J. Virol. 72:873-875), some attempts by other labs to induce neutralizing antibody to gH/gL were negative (Browne et al., 1993, J. Gen. Virol. 74:28 13-7). In contrast to A33R however, there are MAbs to gH/gL that neutralize infectivity. It was found that the method of gH/gL purification had profound effects on its immunogenicity. Once the correct conditions were established, the purified gH/gL complex stimulated neutralizing antibodies in rabbits and mice and protected mice from a lethal HSV challenge (Peng et al., 1998, J. Virol. 72:65-72).

Non-neutralizing MAbs to A33R are also tested in the mouse model for therapeutic efficacy. It has been observed that a combination of the genes for A33R and L1R worked better as a DNA vaccine than either protein alone (Hooper et al., 2000, Virology. 266:329-39). MAbs that represent different epitopes and have high affinity for A33R are chosen. The efficacy of each MAb can be assessed in the mouse model, and the most appropriate ones are selected for a mixture. One or more A33R MAbs can be added to an optimized L1R mix to determine whether the mixture produces a greater efficacy than the A33R mix alone, thereby mimicking a passive immunization similar to as demonstrate by Hooper et al. (2000, Virology. 266:329-39) with active immunization.

Once the efficacy of the VIG-R mixture in the therapeutic mouse IP-IP model is established, different routes of infection (such as intranasal) and passive immunization (such IM) can be considered. Because dangerous complications from VV vaccination can occur in immunocompromised hosts, MAbs are tested by VV challenge in antibody treated athymic nude mice. These mice specifically lack functional T-helper cells, and do not undergo isotype progression to IgG, and do not induce cytotoxic T-cells. Therefore, they are highly susceptible to VV infection (Flexner et al., 1987, Nature 330: 259-262; Flexner et al., 1990, Vaccine 8:17-22; Karupiah et al., 1990, J. Exp. Med. 172:1495-1503; Karupiah et al., 1990, Cell Biol. 68:325-33; Karupiah et al., 1990, J. Immunol. 144:290-298; Karupiah et al., 1991, J. Immunol. 147:4327-4332; Ramshaw et al., 1987, Nature 329:545-546; Ramshaw et al., 1986, Vaccines Meeting, Lorne, Victoria). Nude mice develop generalized *vaccinia* disease and succumb to an IV or IP dose of virus within a few days after infection. VIG-R may allow the mice to live longer after a VV challenge or clear the infection. VV strain WR grows to higher titers in mouse ovaries than in any other organ (Karupiah et al., 1990, Immunol. Cell Biol. 68:343-6; Karupiah et al., 1990, J. Exp. Med. 172:1495-1503; Karupiah et al., 1990, Cell Biol. 68:325-33; Karupiah et al., 1990, J. Immunol. 144:290-298; Karupiah et al., 1991, J. Immunol. 147:4327-4332; Ramirez et al., 2002, J. Gen. Virol. 83:1059-67). Ramirez et al. (2002, J. Gen. Virol. 83:1059-67) examined viral titers in the ovaries to assess the effect of a therapeutic MAb on virus dissemination. The MAb mixtures of the present invention, can be used to examine virus titers in the ovaries of both normal and/or nude mice.

Example 4

Antigenic Analysis of the *Vaccinia* Virus Envelop Glycoprotein B5R

B5Rt was injected in rabbits to obtain rabbit polyclonals (PAbs). These polyclonals were tested for EEV neutralization as disclosed elsewhere herein. Two different techniques were used for testing the neutralization capability of the antibodies: a plaque reduction assay (assay for virus entry) and a comet-tail inhibition assay (assay for virus spread).

Figure 17A:
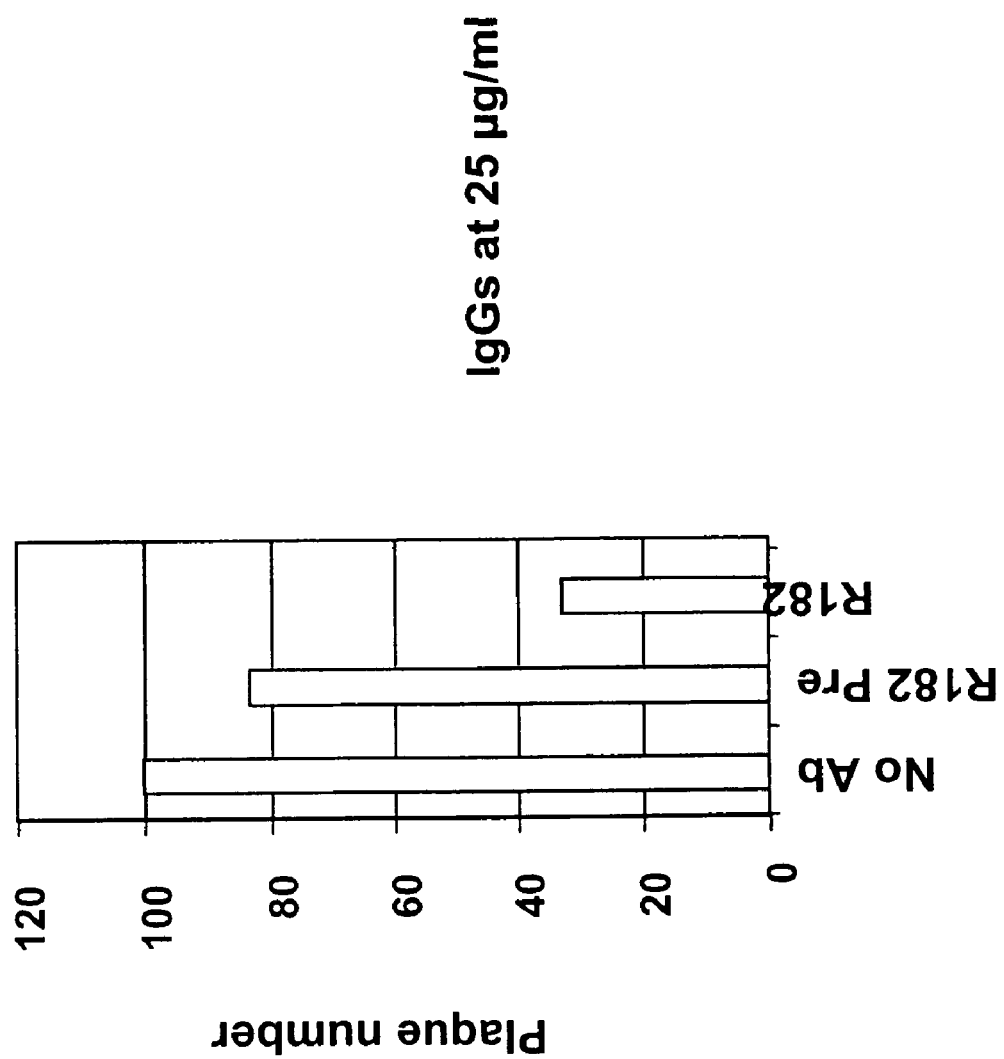
FIGS. 17A-17B, depicts a series of graphs and images depicting the activity of anti-B5Rt in EEV neutralization and passive immunization.

A plaque reduction assay was employed to assess the effect of adding anti-B5R rabbit polyclonal on plaque number. A plaque reduction assay encompasses infecting a monolayer of cells with a preparation of EEV and then counting the plaques. EEV is very fragile and its membranes can lyse, thereby releasing IMV. In order to avoid initial plaque formation by IMV, anti-L1R MAbs and PAbs were added to the preparation. As a negative control, cells were infected with EEV in the absence of an antibody, and the number was normalized to 100. Another negative control involved incubating of EEV with IgGs obtained from rabbit pre-immune sera. It was observed that there was a reduction of about 65% in the number of plaques when EEV was incubated with IgGs purified from the immunized rabbit (FIG. 17A).

Figure 17B:
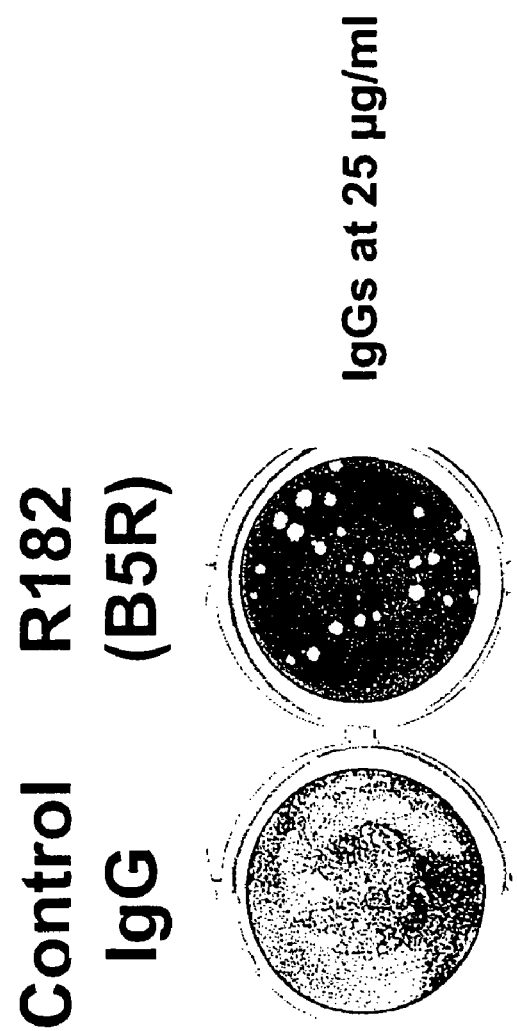

For the comet-tail inhibition assay, a different strain of VV, strain IHDJ, which releases a large amount of EEV that then forms plaques in a cell monolayer that resemble comet-tails, was employed. The comet-tail inhibition assay demonstrated the effect on tail formation when IgG was added to the culture medium. In the negative control, cells were infected with EEV wherein a control IgG was added to the culture medium. Comet-shaped plaques were observed in the negative control. In the sample where the rabbit polyclonal was added to the culture medium, inhibition of tail formation was observed (FIG. 17B). The data disclosed herein demonstrated that the rabbit polyclonal R182 was directed against B5Rt.

Passive protection studies were performed to test the effects of the rabbit antibody R182 in vivo. 5 mg of purified rabbit polyclonal IgG was administered intraperitoneally to naïve mice. After 24 hours the mice were challenged intranasally with $10^6$ pfu of VV. The animals were weighed daily and were sacrificed if they lost 30% of their initial weight. In untreated uninfected animals, no weight loss was detected, whereas unimmunized mice had rapid weight loss and had to be sacrificed by day 7. Animals that had been immunized with polyclonal anti-B5Rt lost weight but started coping by day 8 as demonstrated by weight gain (FIG. 17C).

In summary, the data disclosed herein demonstrate that B5Rt can be expressed in baculovirus, and further, the expressed B5Rt was recognized by VIG, and baculovirus-produced B5R elicited virus-neutralizing antibodies in an animal. The neutralizing antibodies recognized VV B5R and the antibodies passively protected animals against VV infection in an art-recognized passive immunization model.

Mapping B5R Immune Epitopes

Figure 18:
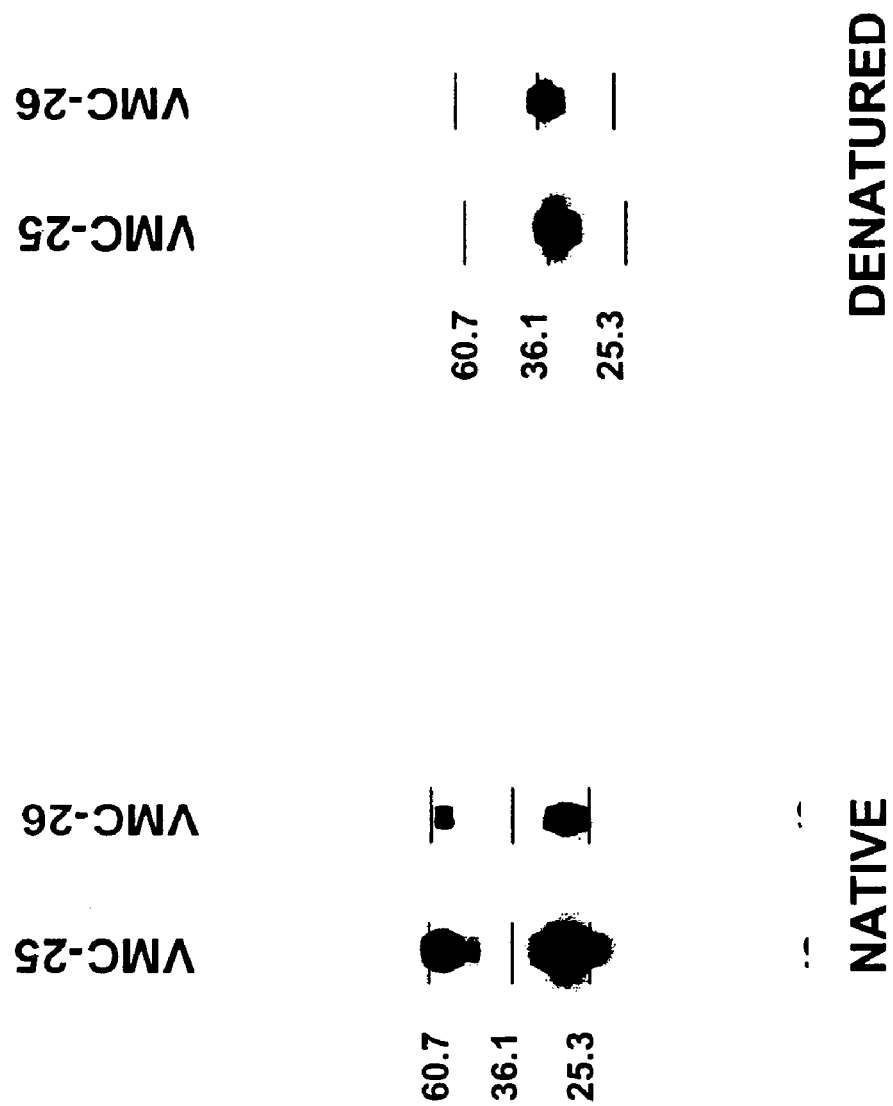
FIG. 18 depicts a series of images of Western blots demonstrating the binding of two of the 26 monoclonal antibodies directed to B5R (i.e., VMC-7 to VMC-33), under native and denaturing conditions.

MAbs against B5Rt were generated and were used to study the structure and function of B5R. Twenty-six (26) MAbs were produced and designated VMC-7 through VMC-33, except there is no VMC-17. The MAbs were tested against B5R using western blot, in native and denaturing conditions (FIG. 18). MAbs were able to recognize the dimer and the monomer of B5R under native conditions. Under denaturing conditions, the MAbs recognized the monomer. These results demonstrate that the MAbs are directed against a linear epitope of B5R.

The biological activity of the MAbs was assayed as described elsewhere herein. For example, the MAbs were tested using the same methods as used with respect to characterization of rabbit polyclonal antibodies. That is, the MAbs were characterized using a plaque reduction assay and a comet tail inhibition assay. The MAbs can also be assessed in passive protection experiments.

Figure 19:
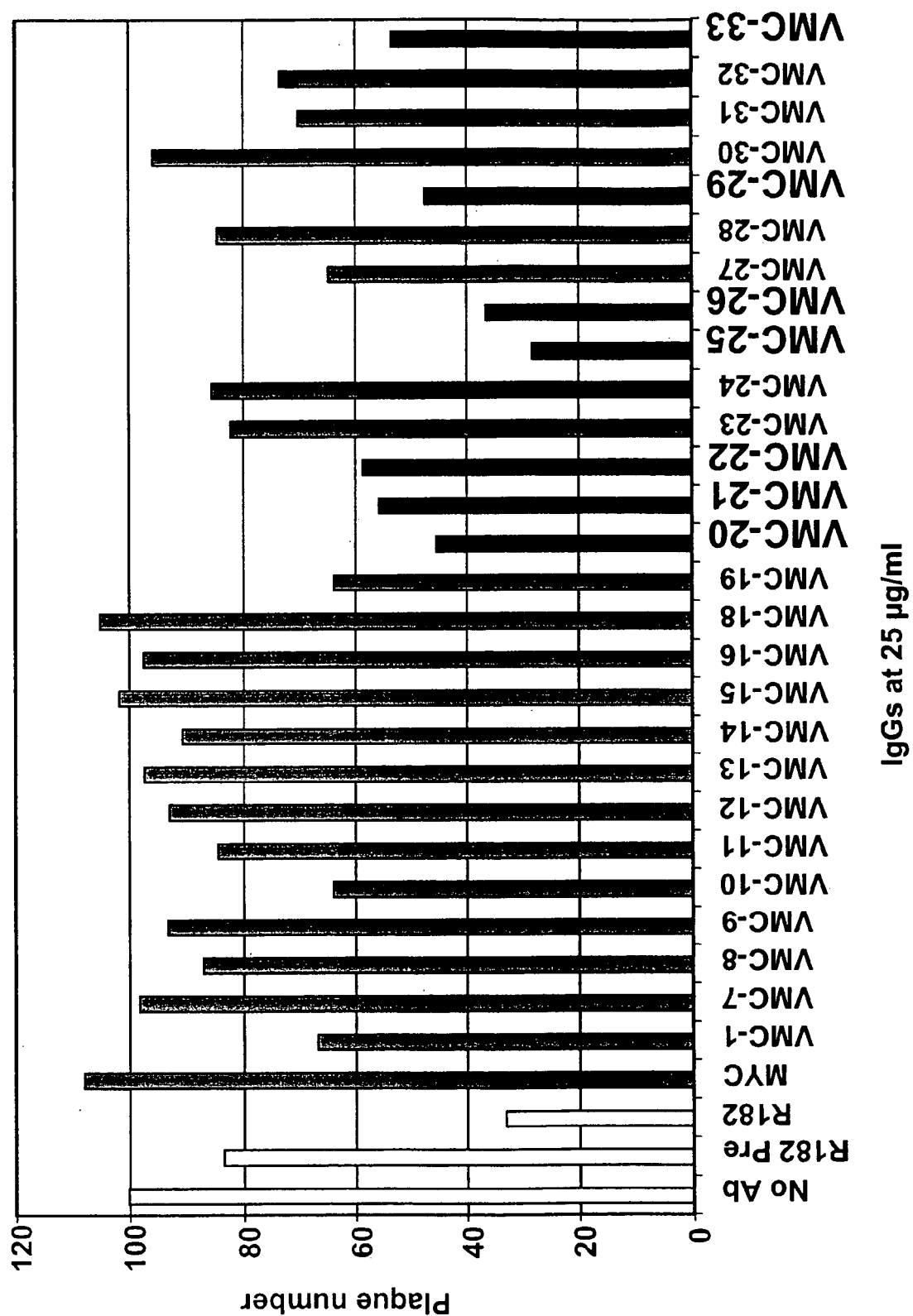
FIG. 19 is a histogram depicting the results of a plaque reduction assay using the 26 anti-B5R monoclonal antibodies. The plaque reduction assay was performed as described elsewhere herein. The negative control was a monoclonal against the MYC protein.

The plaque reduction assay was performed as described elsewhere herein. The negative control was a monoclonal directed against the MYC protein. Several MAbs demonstrated the ability to reduce plaque formation. Control wells to which no IgG was added, and each monoclonal was tested in duplicate. VMC-26 and VMC-27 did not inhibit comet tail formation, but VMC-25 and VMC-29 did. An anti-B5R rat monoclonal was used as a positive control and was observed to have inhibition properties (FIG. 19).

Figure 20:
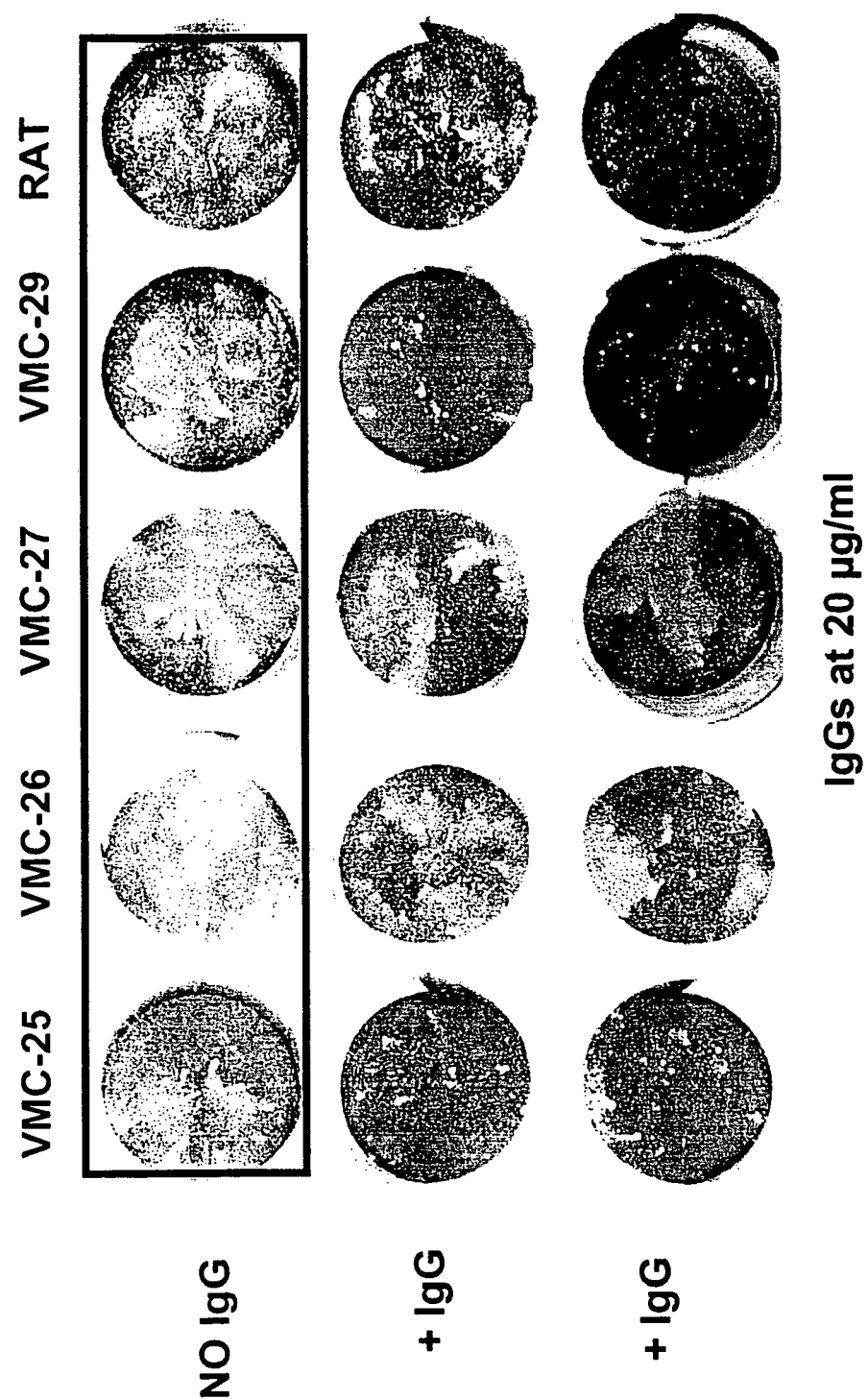
FIG. 20 is a series of images depicting a comet tail inhibition assay using the monoclonals against B5R. On the top row are the control wells, in which no IgG was added. Each of the monoclonals was tested in duplicate. It was observed that VMC-26 and VMC-27 do not inhibit comet tail formation, but VMC-25 and VMC-29 did. A rat anti-B5R monoclonal was also observed to inhibit comet tail formation.

The MAbs were also used in a comet tail inhibition assay (FIG. 20) and that data demonstrated that VMC-25 and VMC- 29 are both biologically active in plaque reduction assays and comet tail inhibition assays (FIG. 21).

To test the biological activity of the MAbs in vivo, mice were injected with VMC-25 and challenged with a lethal dose of *vaccinia* one day later. The mice were weighed daily. The mice that were not immunized lost a substantial amount of weight and had to be sacrificed by day 7 (i.e., the protocol called for sacrificing animals once they had lost approximately 30% of their body weight). Mice that were injected with anti-ovalbumin antibody had the same disease progression as non immunized mice and had to be sacrificed by day 8. Mice that were injected with VMC-25 lost less weight, by day 6 their weight had stabilized, and by day 12 they had resolved the illness (FIG. 22). These results demonstrate that MAbs selected against the baculovirus-expressed B5Rt neutralized EEV in vitro and conferred passive protection in an art-recognized murine model of poxvirus infection.

Epitope Mapping Using Peptides and the BIAcore

Twenty-eight (28) overlapping peptides that spanned the extracellular domain of B5R were produced. Each peptide was 20 amino acids in length and overlapped the contiguous peptide by 10 amino acids.

Figure 23:
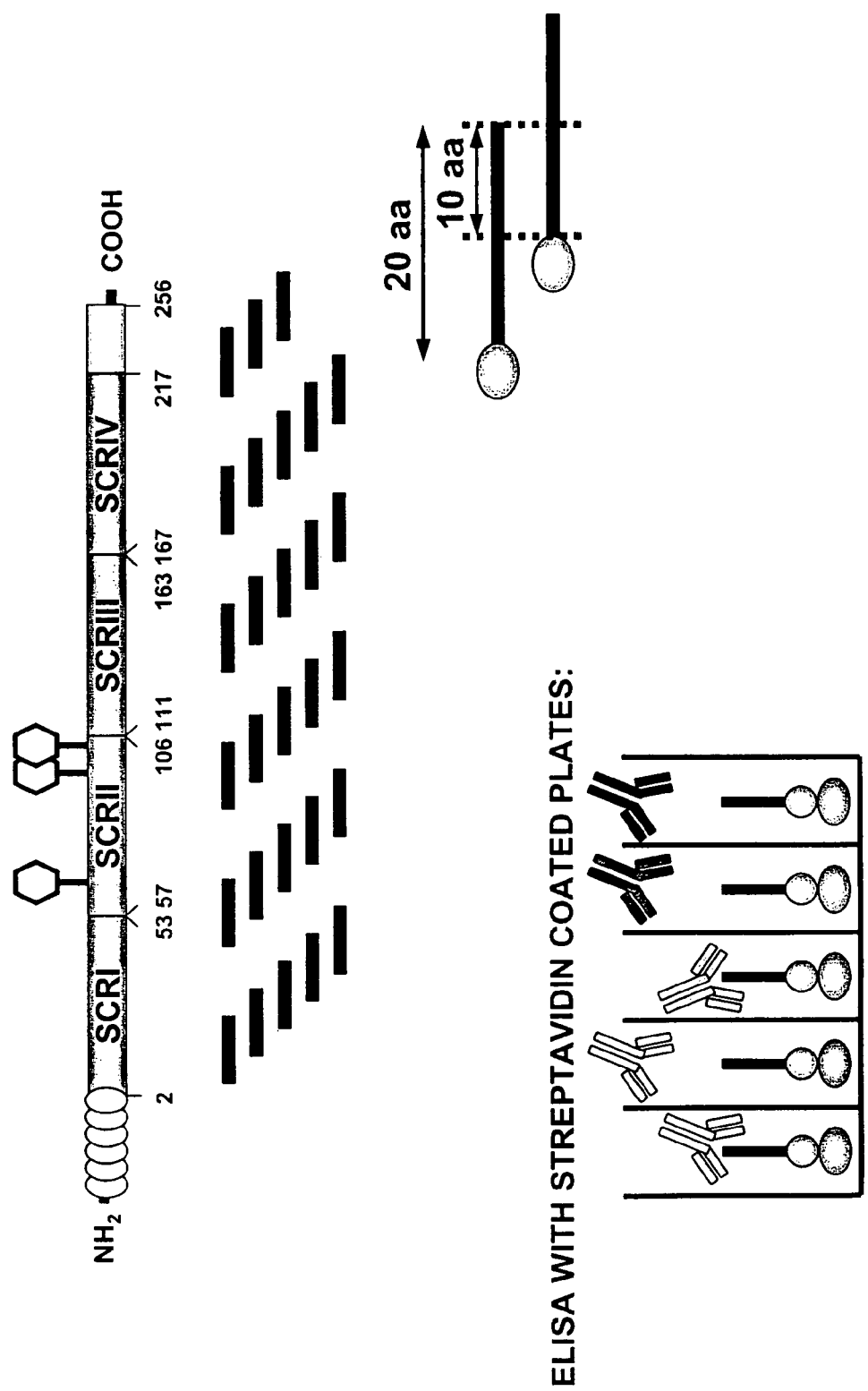
FIG. 23 is a schematic depicting 28 overlapping peptides that spanned the extracellular domain of B5R. Each peptide was 20 amino acids in length and overlapped the contiguous peptide by 10 amino acids. A biotin was included in its N-terminus, which was useful in screening the peptide panel with the MAbs by using streptavidin-coated plates in an ELISA assay.

Biotin was included in the N-terminus of each peptide. Biotin allows for the screening of the peptide panel with the panel of MAbs using streptavidin-coated plates in an ELISA assay (FIG. 23).

Figure 24:
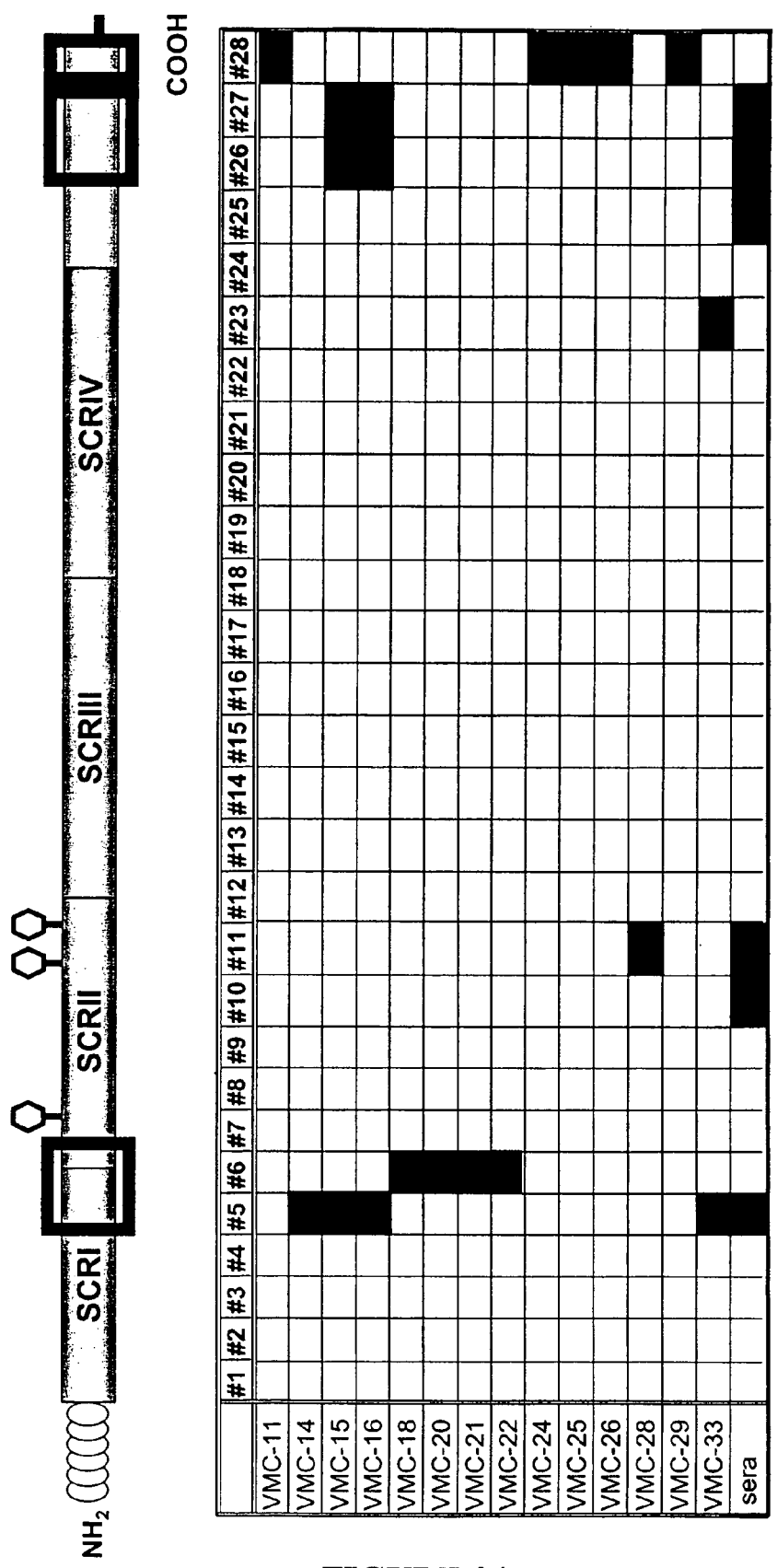
FIG. 24 summarizes the results from the peptide screening. On top is a diagram of the ectodomain of B5R. The table depicts a representative group of MAbs. The table has peptides in its columns and MAbs in each row. The peptides are arranged to depict the spatial representation of the peptides with respect to B5R. Positive binding is depicted with a solid square. It is observed that most of the MAbs recognized the border SCR1-2 and the stalk. It is also observed that no MAbs tested recognized SCR3 and only one recognized SCR4 (VMC-33). The sera obtained from the fusion mouse also recognized peptides from SCR1, SCR2 and the stalk. Some antibodies (VMC-15, VMC-16 and VMC-33) recognized peptides located in both the SCR1-2 and the stalk domains. It is observed that antibodies that were positive in the plaque reduction assay (VMC-20, VMC-21, VMC-22, VMC-25, VMC-29 and VMC-33) was observed to recognize either SCR1-2 or the stalk domain. VMC-25 and VMC-29, the antibodies observed to inhibit comet tail formation, was observed to recognize peptide No. 28.

A diagrammatic representation of the extracellular domain of B5R comprising SCR1, SCRII, SCR III, SCRIV and stalk domains is depicted in FIG. 24. Further, FIG. 24 depicts a representative group of MAbs and peptides, wherein the peptides are arranged in columns and MAbs are organized along each row. It is observed that most of the MAbs recognized the border SCR1-2 and the stalk, as a positive binding is represented by a solid square. It is also observed that no MAbs tested recognized SCR3 and only one recognized SCR4 (VMC-33). The sera obtained from the fusion mouse also recognized peptides from SCR1, SCR2 and the stalk. Some antibodies (VMC-15, VMC-16 and VMC-33) recognized peptides located in both the SCR1-2 and the stalk domains. It is observed that antibodies that were positive in the plaque reduction assay (VMC-20, VMC-21, VMC-22, VMC-25, VMC-29 and VMC-33) was also observed to recognize either SCR1-2 or the stalk domain. VMC-25 and VMC-29, antibodies observed to inhibit comet tail formation, was also observed to recognize peptide number 28, which is located at the stalk.

Several antibodies recognized both the SCR1-2 and the stalk region, thereby suggesting that the N-terminus and the C-terminus of B5R comprise a structural domain. The panel of MAbs was analyzed by BIAcore, which allows for observation of the binding in real time. An anti-His tag antibody was coupled to a chip, and the injection of B5Rt, which is His-tagged, was captured by the anti-His tag antibody by its His-tag, thereby leaving all of the B5Rt oriented in the same direction on the chip.

The binding of B5R was monitored and was observed as an increase in resonance units. If an antibody did not bind to B5R, binding was not observed and the chart depicts slow dissociation of B5R. If an antibody that bound to B5R was injected, the binding was observed as a resultant second increase in resonance units, as depicted in the chart as a circle. The chart demonstrates a clear distinction between the antibodies that bind to B5R and those that do not bind, or that bind at low affinity.

Binding competition assays were performed to analyze whether the MAbs that bound to B5R in BIAcore conditions bound the same epitope. B5R was injected and an increase in resonance units was observed indicative of a positive binding event. In a case were a first MAb was then injected, which binds to B5R, a second increase in resonance unit was observed until the epitope was saturated. In a case of a subsequent injection of another antibody that binds to a different epitope than the first antibody, a third increase in resonance units was observed. However, if the second antibody injected recognized the same or adjacent epitope as the first one, the second antibody was unable to bind because the epitope was already saturated by the first antibody (demonstrated by a straight line). Thus, where a curve is observed, there was no competition between the first and the second antibody, indicating that the antibodies bound different non-competing epitopes. A straight line is indicative of antibodies binding to the same or adjacent epitopes such that there was competition between the antibodies for binding to the same/adjacent domains.

When additional VMC-25 was injected its epitope had been saturated with VMC-25, there was a slight binding which was considered as background (0%). When VMC-25 was injected following several other antibodies, it was observed that VMC-25 was able to bind, indicating that VMC-25 binds to a different epitope than those other antibodies. But when VMC-25 was injected after having saturated B5R with the rat monoclonal, VMC-25 bound weakly (17%), indicating that the rat MAb and VMC-25 bound to the same or adjacent epitopes of B5R. It was observed that VMC-22 did not compete with any MAb.

Binding competition assays were performed with all available antibodies. The antibodies that were injected first are indicated along the top of the table, and the vertical rows indicate the antibodies that were injected after the first MAb. The results are expressed in terms of percentage of binding of the second antibody (FIG. 25).

Where VMC-32 was injected after having injected VMC-19 as the first antibody, VMC-32 was observed to bind only about 2%. Reciprocal inhibition was assessed by injecting VMC-32 as the first antibody followed by injection VMC-19 as the second MAb. The data demonstrated that there was no binding by VMC-19 when it was injected after saturating the epitope by VMC-32. Reciprocal inhibition was also tested with the other competing MAb pairs, and all MAbs competed with each other in a reciprocal manner (FIG. 25).

Using the data obtained in the BIAcore assay, antibodies were grouped in binding competition groups (i.e., antibodies that bind to the same epitope and/or to an adjacent epitope). VMC-19 and VMC-32 are in the same group, and the competition is depicted as a solid line. VMC-22 does not compete with any other antibody. VMC-25 and VMC-29 are in the same group, in that while they do not compete with each other, they are related in that both compete with the rat MAb.

Figure 26:
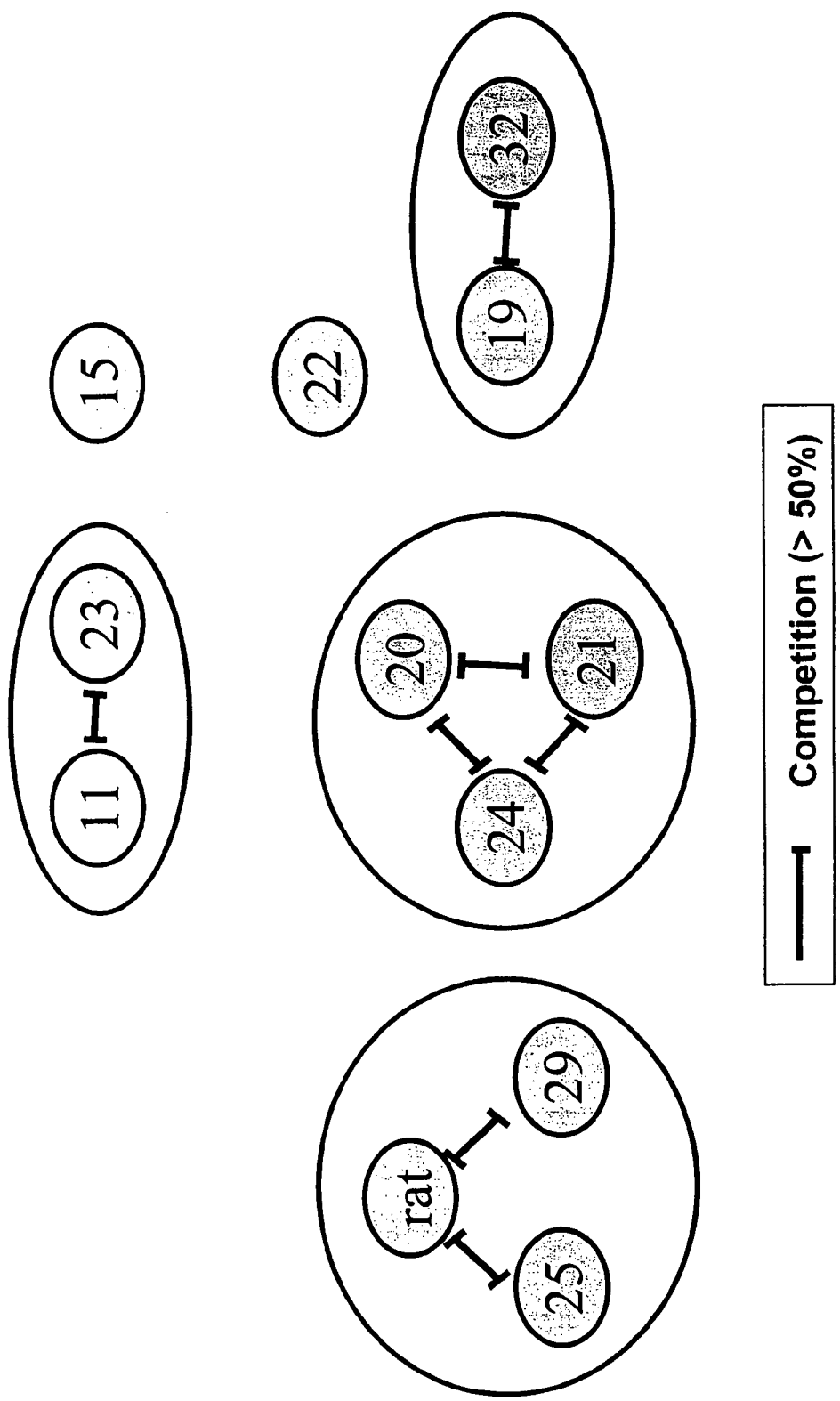
FIG. 26 is a schematic of B5R binding competition groups. VMC-20, VMC-21 and VMC-24 are in the same competitive group because they compete with each other, in a reciprocal manner, but they appear to recognize different peptides.

VMC-20, VMC-21 and VMC-24 are in the same competitive group because they compete with each other, in a reciprocal manner, but they appear to recognize different peptides (FIG. 26). VMC-20 and VMC-21 recognize peptides located in the SCR1-2 region of B5R, whereas VMC-24 recognizes a peptide located in the stalk. Without wishing to be bound by any particular theory, these data, together with the presence of several antibodies that recognize distal epitopes, suggest that there is a structural domain formed by the N-terminus and the C-terminus of B5R.

Figure 27:
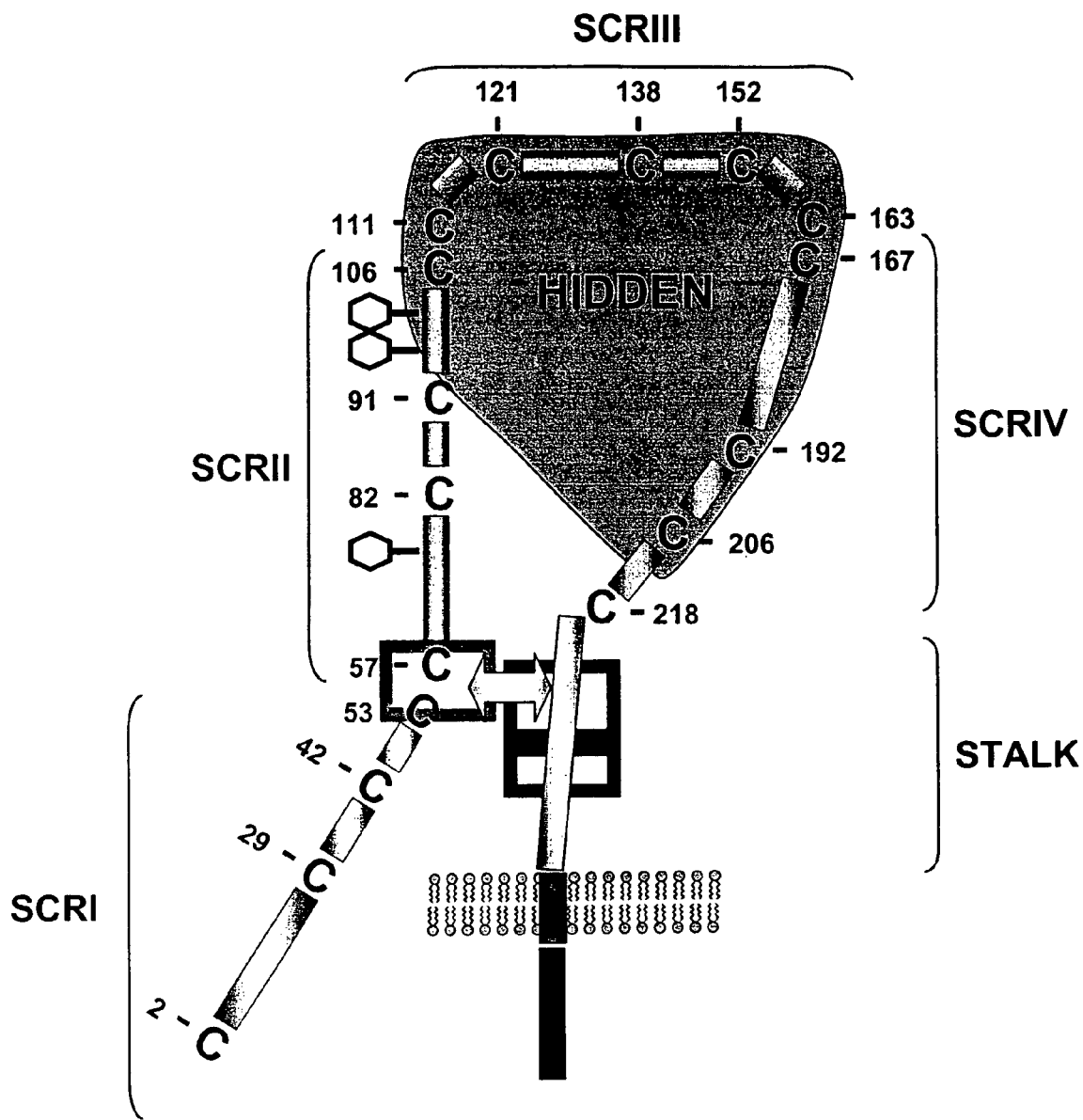
FIG. 27 is a two-dimensional model of B5R. Without wishing to be bound by any particular theory, B5R is depicted as comprising the SCR1-2 and the stalk regions in a spatial proximity, and it is this region that can form the antigenic site of B5R recognized by the MAbs disclosed herein. Analysis of the peptide data further suggests that SCR3 and 4 are hidden from the immune response.

In a two-dimensional model, B5R is depicted as comprising the SCR1-2 and the stalk regions in a spatial proximity, and it is this region that apparently forms the antigenic site of B5R recognized by the MAbs disclosed herein. Analysis of the peptide data further suggests that SCR3 and 4 are hidden from the immune response, as no observable antibody was selected that recognized these regions (FIG. 27).

In sum, the antigenic analysis of B5R disclosed herein demonstrates that the virus neutralizing epitopes correspond to the SCR1-2 region and the stalk. The IgG against SCR2 alone (VMC-28) did not neutralize EEV in vitro. The MAbs as disclosed herein are useful for analyzing the structure of B5R. Also, the epitope mapping data disclosed herein demonstrate that the N-terminus and the C-terminus of B5R form a structural domain that can be either intramolecular or intermolecular (as in dimer interaction). Additionally, no IgGs were observed to recognized SCR3 or 4, suggesting these domains are hidden to the immune system due to their role in dimer interaction. Thus, the MAbs disclosed herein provide powerful tools for, inter alia, analyzing the conformation and immunological properties of potential soluble subunit vaccine candidate peptides of the invention.

Further, the data disclosed herein allow analysis of the mechanism of antibody neutralization of EEV. Moreover, because the MAbs disclosed elsewhere herein against VV B5R also recognize B6R, which is the smallpox homologue, the MAbs can be used to perform protection studies with smallpox virus and to map the (immunologically important) B6R epitopes as demonstrated herein for VV B5R. Further, as discussed elsewhere herein, VIG recognizes the baculovirus-expressed B5Rt such that, using the MAbs and peptides disclosed elsewhere herein, the recognition site(s) of VIG can be mapped to the corresponding peptides as was demonstrated herein for B5R using competition experiments on the BIAcore chip.

With respect to the structure of B5R, truncated forms of B5R (B5Rt) and point mutations can be used to verify the structural model and to identify and map the dimerization domain. Crystallized B5Rt is also useful to verify the conformational model disclosed herein and to identify and characterize the dimerization domain.

The ability of the baculovirus-expressed B5Rt to block virus infection can be assessed using the methods disclosed herein and the effect of the twenty-eight peptides on virus entry can be used to assess the in vivo immunomodulatory function of the various domains.

Example 5

Immunization with Recombinant Proteins Protect Mice Against Lethal Intranasal Infection with Pathogenic *Vaccinia* Virus Groups of ten to twelve 6-week old female Balb/c mice were immunized subcutaneously with 10 μg of recombinant *vaccinia* virus proteins A33Rt, B5Rt or L1R(185t) or with combinations of these proteins. The proteins were prepared with MPL+TDM adjuvant (Sigma-Aldrich, St. Louis, Mo.) diluted in PBS as recommended by the manufacturer. Three booster immunizations were given at three-week intervals. As a positive control, a group of mice received a single percutaneous immunization with the Wyeth (Dryvax) live *vaccinia* virus smallpox vaccine. Another group of mice were unimmunized. Antibody responses (e.g., end point ELISA titers) to the individual recombinant proteins and to a lysate of *vaccinia* virus infected cells, at three weeks following the fourth protein immunization, were obtained (Table 2). The antibody titers to the individual proteins were much higher after recombinant protein immunization than the antibody titers from immunization with VV (Wyeth Dryvax). Of the three proteins, the A33Rt was most immunogenic, whether tested on purified protein or in an infected cell lysate assay.

TABLE 2

| Immunization | Plates coated with: | | | |
|---|---|---|---|---|
|  | A33Rt protein | B5Rt protein | L1R(185t) protein | Infected cell lysate |
| A33R | 1:800,000 | — | — | 1:200,000 |
| B5R | — | 1:200,000 | — | 1:3200 |
| L1R | — | — | 1:100,000 | 1:6400 |
| A33R + B5R | 1:400,000 | 1:100,000 | — | 1:100,000 |
| A33R + L1R | 1:400,000 | — | 1:100,000 | 1:100,000 |
| B5R + L1R | — | 1:100,000 | 1:100,000 | 1:6400 |
| A33R + B5R + L1R | 1:400,000 | 1:50,000 | 1:100,000 | 1:75,000 |
| Vaccinia virus (Wyeth) | 1:12,800 | 1:3200 | 1:12,800 | 1:25,000 |
| Unimmunized | <1:200 | <1:200 | <1:200 | <1:200 |

Neutralizing antibodies to the IMV form of *vaccinia* virus were induced by the L1R(185t) protein alone, or L1R(185t) combined with Wyeth vaccine (Dryvax), but not by either A33Rt or B5Rt protein alone (Table 3).

TABLE 3

| Immunization | Bleed | | | |
|---|---|---|---|---|
|  | 1 | 2 | 3 | 4 |
| L1R(185t) | <100 | 1876 | 12150 | 18250 |
| A33Rt + L1R(185t) | <100 | 585 | 12180 | 14540 |
| B5Rt + L1R(185t) | <100 | 786 | 11533 | 10250 |
| A33Rt + B5Rt + L1R(185t) | <100 | 123 | 6039 | 9595 |
| Vaccinia virus (Wyeth) | 2244 | 8079 | 6924 | 6960 |

Figure 28:
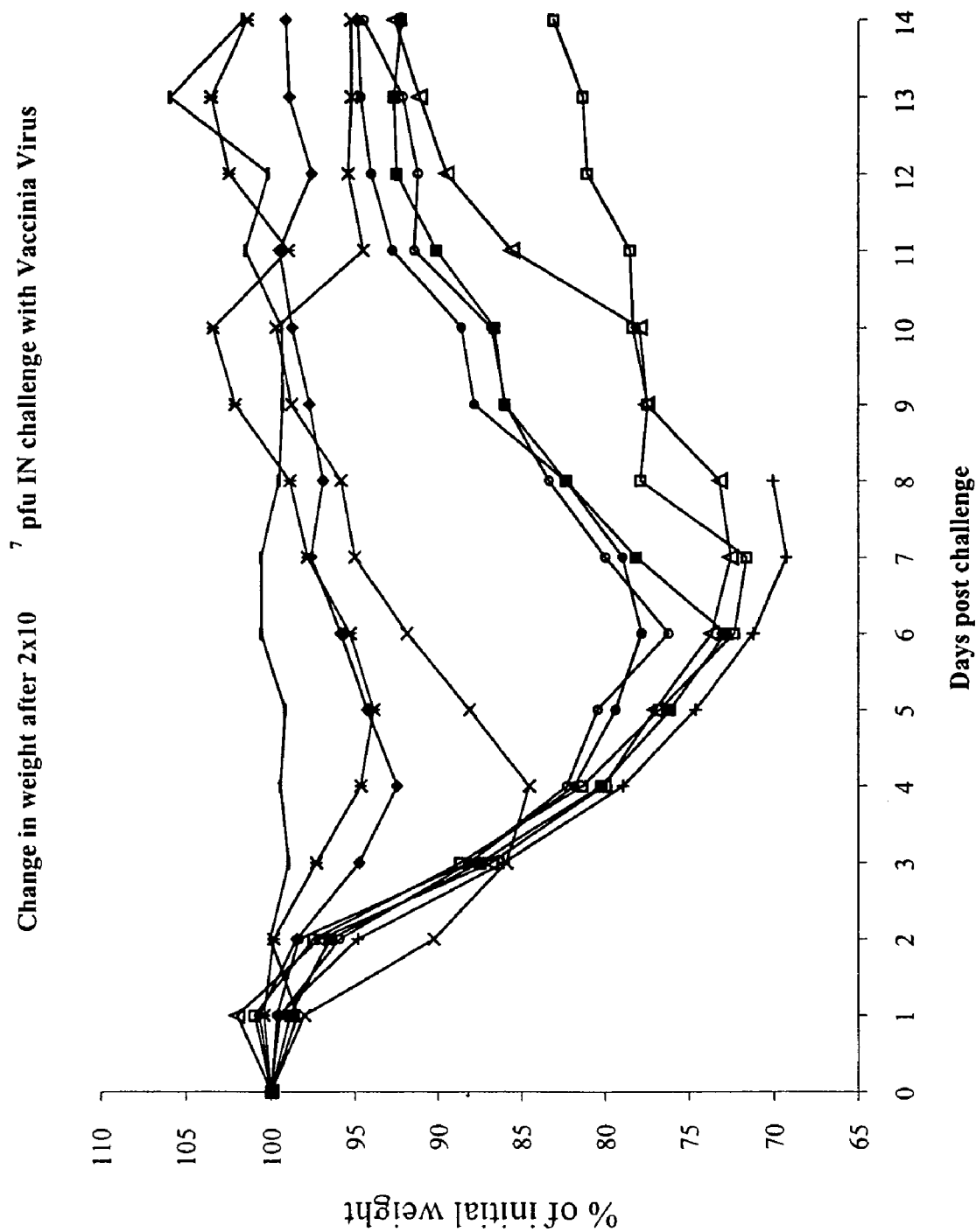
FIG. 28 is a graph depicting results from protein immunization. Mice were challenged intranasally with $2 \times 10^7$ pfu of vaccinia virus Western Reserve (WR), wherein $LD_{50}$ is approximately $10^4$ pfu. The average daily weights were computed as a percentage of the initial weight. Unimmunized mice exhibited rapid weight loss and all had to be sacrificed by eight days after challenge. The immunized mice had varying degrees of weight loss but none died. Mice immunized with all three proteins or with the combination of A33R and L1R lost less weight than the group immunized with the Wyeth vaccine strain, whereas mice immunized with single proteins or other combinations exhibited greater weight loss.

At three weeks after the fourth protein immunization, the mice were challenged intranasally with $2 \times 10^7$ pfu of *vaccinia* virus Western Reserve (WR), wherein $LD_{50}$ is approximately $10^4$ pfu. The animals were weighed daily and were sacrificed if they lost about 30% of their initial weight, according to NIH guidelines. The average daily weights were computed as a percentage of the initial weight. Unimmunized mice exhibited rapid weight loss and all had to be sacrificed by eight days after challenge (FIG. 28). The immunized mice had varying degrees of weight loss but none died. Mice immunized with all three proteins or with the combination of A33Rt and L1R (185t) lost less weight than the group immunized with the Wyeth vaccine strain, whereas mice immunized with single proteins or other combinations exhibited greater weight loss.

Example 6

Figure 29:
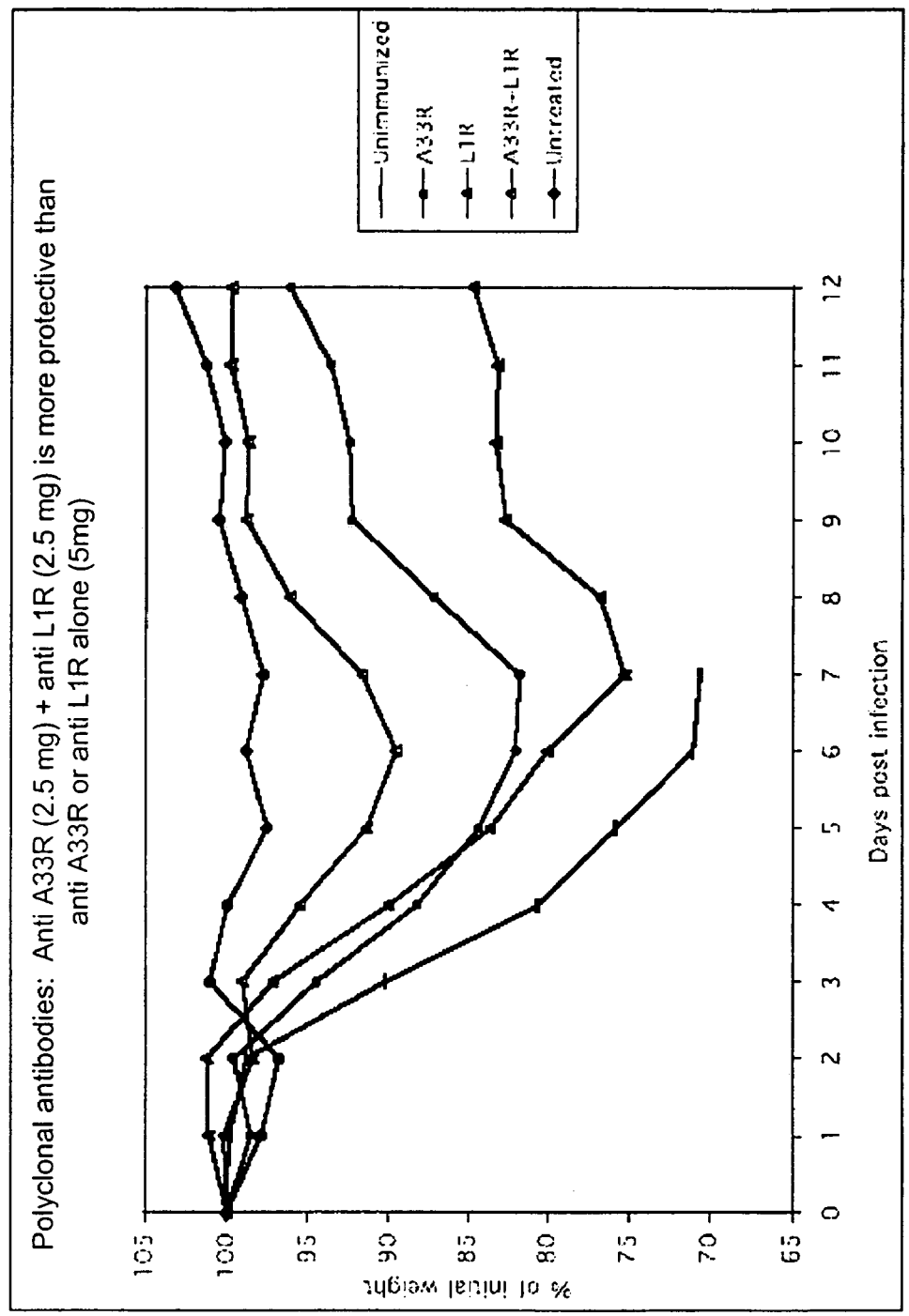
FIG. 29 is a graph demonstrating that passive immunization using polyclonal antibodies directed to A33Rt and/or L1R(185t) protects mice against a lethal intranasal infection with pathogenic vaccinia virus. The results are expressed as the average daily weight as a percentage of the initial animal weight. All of the control mice died whereas the immunized mice demonstrated varying degrees of weight loss. One mouse out of four died in the groups receiving antibody to just A33Rt or L1R(185t). All animals receiving combinations of antibodies were all protected and none were sacrificed or died. Animals receiving anti-A33Rt and anti-L1R(185t) antibodies lost less weight than those receiving only anti-A33Rt or anti-L1R(185t) antibodies.
Figure 30:
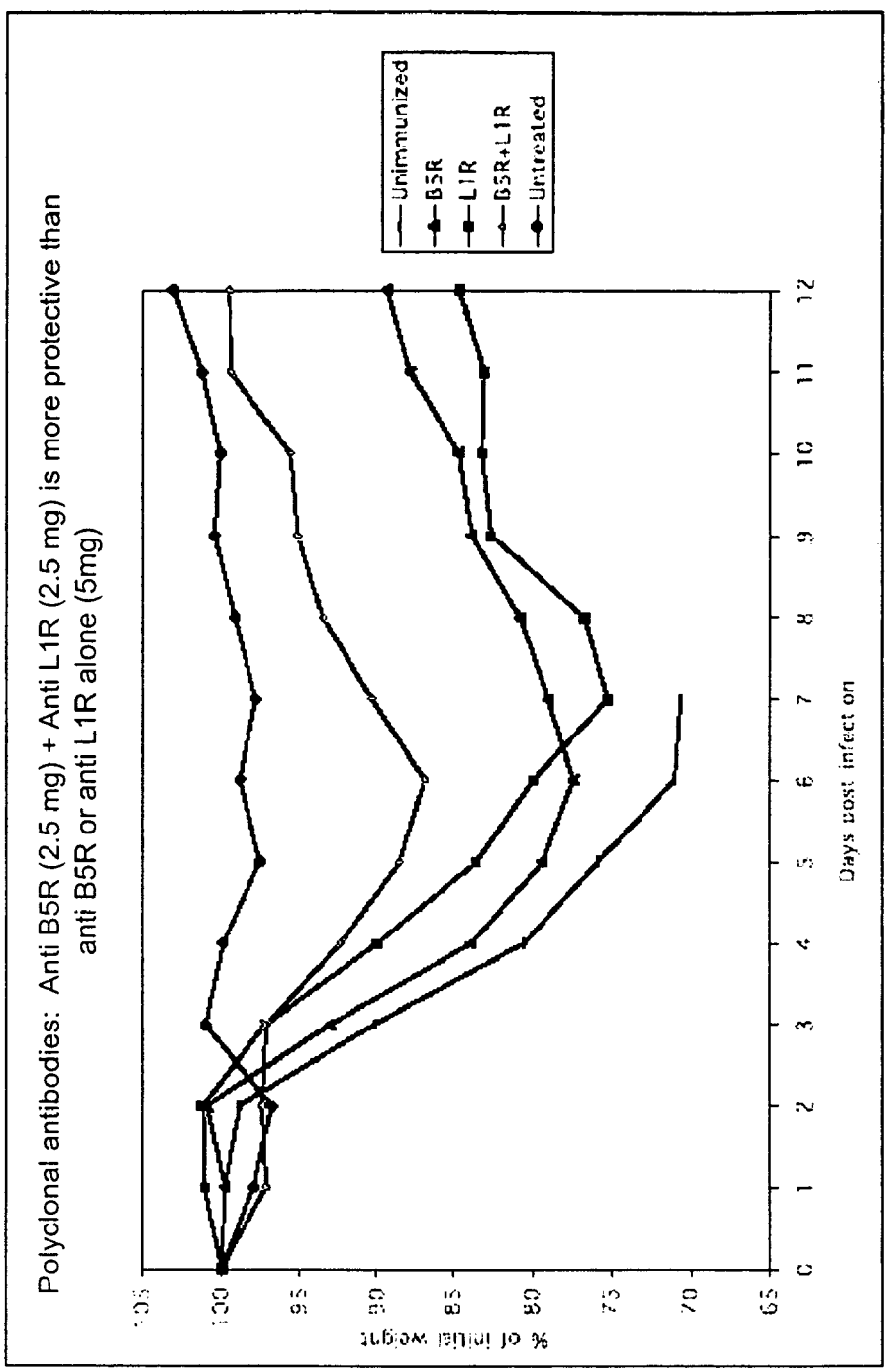
FIG. 30 is a graph demonstrating that passive immunization using polyclonal antibodies directed to B5Rt and/or L1R (185t) protects mice against a lethal intranasal infection with pathogenic vaccinia virus. Animals receiving anti-B5Rt and anti-L1R(185t) antibodies lost less weight than those receiving only anti-B5Rt or anti-L1R(185t) antibodies.
Figure 32:
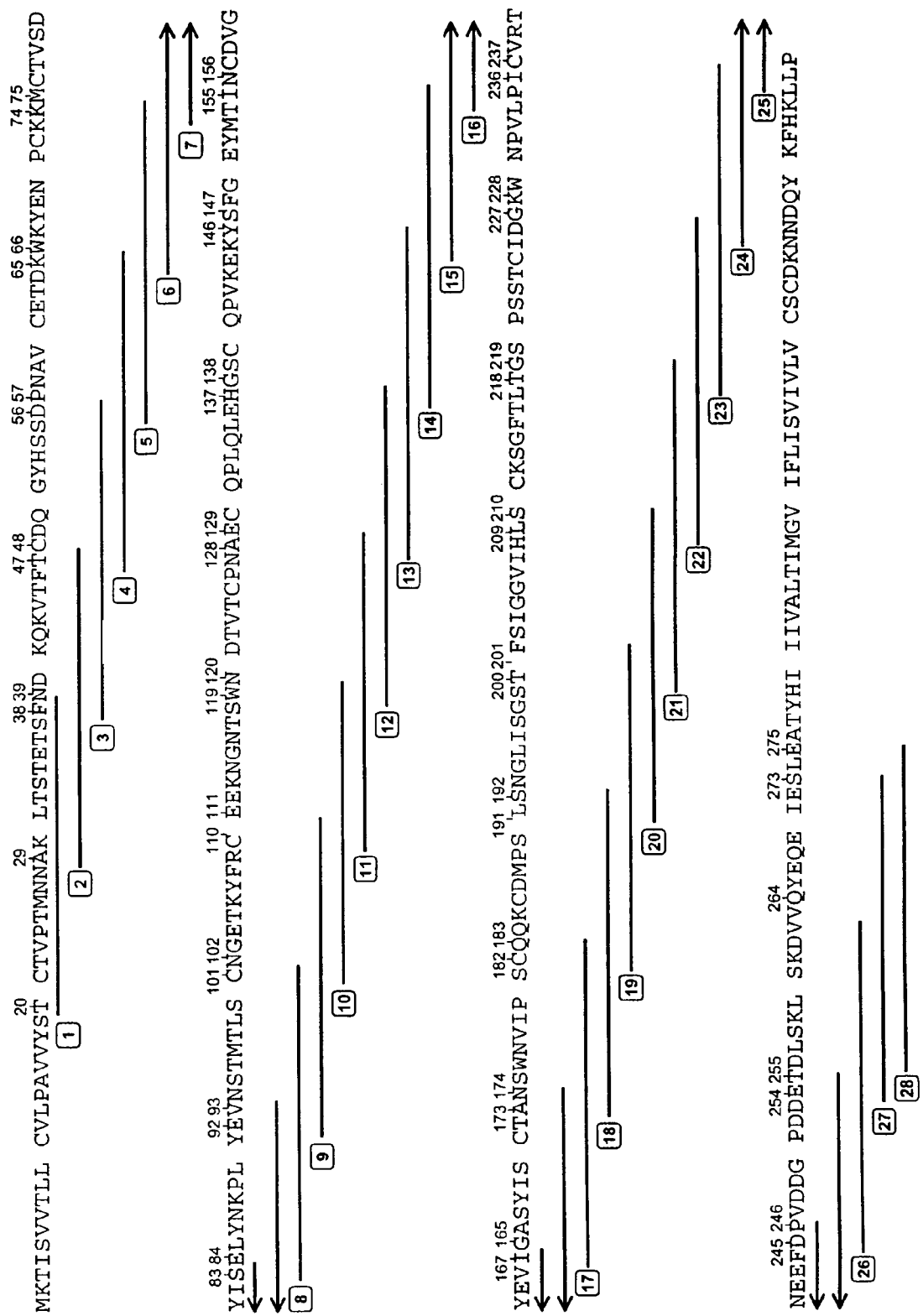
FIG. 32 is a schematic diagram depicting B5R WR Q01227 (SEQ ID NO. 41) and 28 overlapping peptides that spanned the extracellular domain of B5R. The amino acid sequence of B5R WR Q01227 corresponding to SEQ ID NO. 41 and each corresponding peptide and the range for which each peptide spans the extracellular domain of B5R are shown.

Passive Immunization Protects Mice Against a Lethal Intranasal Infection with Pathogenic *Vaccinia* Virus PAbs Five mg of purified rabbit polyclonal antibodies (IgG) against A33Rt, B5Rt or L1R(185t), or combinations of these antibodies, were administered intraperitoneally to 14-week-old naive mice. The antibodies were prepared from rabbits immunized with purified L1R(185t) (IMV protein), A33Rt (EEV protein), or B5Rt (EEV protein). As a negative control, a group of mice received 5 mg of IgG against the herpes simplex virus glycoprotein D. After 24 hours, a serum sample was taken from each mouse to verify the predicted antibody titer by ELISA and the mice were challenged intranasally with $1 \times 10^6$ pfu of *vaccinia* virus Western Reserve (10 $LD_{50}$). The animals were weighed daily and were sacrificed if they lost about 30% of their initial weight. The results are expressed as the average daily weight as a percentage of the initial animal weight. All of the control mice died whereas the immunized mice demonstrated varying degrees of weight loss. One mouse out of four died in the groups receiving antibody to just A33Rt or L1R(185t). All animals receiving combinations of antibodies were all protected and none were sacrificed or died. Animals receiving anti-A33Rt and anti-L1R(185t) antibodies lost less weight than those receiving only anti-A33Rt or anti-L1R(185t) antibodies (FIG. 29). In addition, animals receiving anti-B5Rt and anti-L1R(185t) antibodies lost less weight than those receiving only anti-B5Rt or anti-L1R(185t) antibodies (FIG. 30).

MAbs

Corresponding results were obtained using MAbs in that 14-week-old naive mice received intraperitoneal injections of 100 μg of purified mouse MAb against A33Rt, L1R(185t), or rat MAb against B5R. The mice were challenged as disclosed above for rabbit PAbs. The unimmunized animals and animals receiving an irrelevant MAb to ovalbumin all died, whereas the immunized animals lived, although they all suffered transient weight loss.

Figure 31:
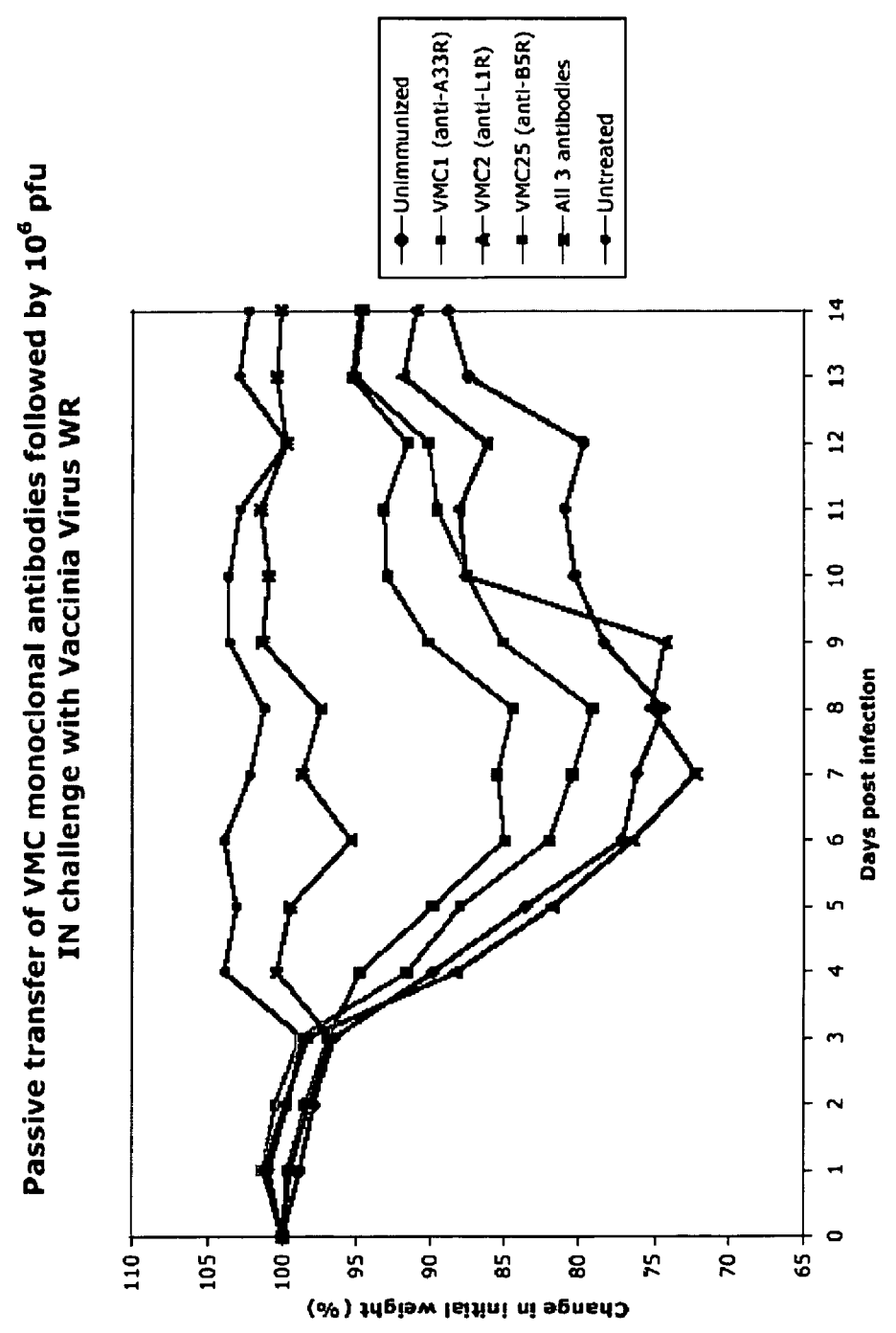

Mice that received 200 μg of individual MAb suffered less weight loss after challenge than those that received 100 μg. However, mice receiving 100 μg of MAb to A33Rt (termed VMC1) plus 100 μg of MAb to L1R(185t) lost less weight than those receiving 200 μg of A33Rt or L1R(185t) MAb separately. Similarly, mice that received 100 μg of MAb to B5Rt and 100 μg of MAb to L1R(185t) (one of which was designated VMC2) were better protected than mice receiving 200 μg of the individual MAb. In contrast, the combination of A33Rt and B5Rt MAbs did not confer greater protection than 200 μg of each MAb alone (FIG. 31). These data demonstrate that the combination of an antibody to the EEV and an antibody to the IMV is preferable, and the combination of MAb to all three proteins is even more preferable.

Example 7

Immunization Using A33Rt, B5Rt and L1R(185T) Proteins in Primates

The data disclosed herein demonstrate immunization of cynomologous monkey using the subunit vaccine polypeptides of the invention. More specifically, monkeys were immunized with 100 μg of each of A33Rt, B5Rt or L1R (185t).

TABLE 4

| week | Animal # | A33R | B5R | L1R | IMV | Lysate |
|------|----------|------|-----|-----|-----|--------|
| 0    | 26       | 1:400 | 1:800 | 1:400 | <1:400 | 1:800 |
|      | 30       | 1:400 | 1:200 | 1:400 | <1:400 | 1:800 |
|      | 770      | 1:800 | 1:800 | 1:800 | 1:400 | 1:800 |
|      | 974      | 1:1600 | 1:1600 | 1:800 | 1:400 | 1:800 |
| 10   | 26       | 1:400 | 1:800 | 1:400 | 1:400 | 1:800 |
|      | 30       | 1:200,000 | 1:25,000 | 1:100.000 | 1:12,800 | 1:25,000 |
|      | 770      | 1:200,000 | 1:200,000 | 1:50,000 | 1:12,800 | 1:50,000 |
|      | 974      | 1:200,000 | 1:400,000 | 1:50,000 | 1:12,800 | 1:50,000 |

Monkey 26 is an unimmunized control. Other three monkeys received 100 micrograms of each protein (L1, A33, B5) with QS21 adjuvant at week 0, 4 and 8. Endpoint ELISA titers shown at Table 4 were determined with sera obtained at two weeks after the third immunization. The ELISA plates contained recombinant A33Rt, B5Rt, L1R(185t) protein, purified *vaccinia* virions (IMV), or a lysate of *vaccinia* virus infected cells. The data disclosed herein demonstrate that the recombinant peptides of the invention readily elicit an immune response in primates, further supporting that they are useful novel antigens for the development of poxvirus therapeutics.

While this invention has been disclosed with reference to specific embodiments, it is apparent that other embodiments and variations of this invention may be devised by others skilled in the art without departing from the true spirit and scope of the invention. The appended claims are to be construed to include all such embodiments and equivalent variations.

What is claimed is:

1. An immunogenic composition comprising two soluble truncated mammalian poxvirus envelope proteins and a pharmaceutically acceptable carrier, wherein said proteins comprise A33Rt and L1R(185t), wherein said L1R(185t) is not myristoylated.

2. The immunogenic composition of claim 1, wherein said poxvirus is at least one poxvirus selected from the group consisting of *vaccinia* virus and *variola* virus.

3. The immunogenic composition of claim 1, said immunogenic composition further comprising at least one protein selected from the group consisting of A17L, A27L, A34R, A56R, D8L, F9L, F13L, and H3L, or a homologue thereof.

4. The immunogenic composition of claim 1, wherein said A33Rt comprises from amino acid residue number 58 to 185 relative to full-length A33R (SEQ ID NO:35).

5. The immunogenic composition of claim 4, wherein the amino acid sequence of said A33Rt is the sequence of SEQ ID NO:3.

6. The immunogenic composition of claim 1, wherein said L1R(185t) comprises from amino acid residue number 1 to 185 relative to full-length L1R (SEQ ID NO:38).

7. The immunogenic composition of claim 1, wherein the amino acid sequence of said L1R(185t) consists of the sequence of SEQ ID NO: 1.

8. The immunogenic composition of claim 1, wherein said immunogenic composition comprises A33Rt and L1R(185t).

9. The immunogenic composition of claim 8, said immunogenic composition further comprising B5Rt.

10. The immunogenic composition of claim 3, wherein said A17L is A17Lt and comprises from amino acid residue number 80 to 138 relative to full-length A17L.

11. The immunogenic composition of claim 1, said immunogenic composition further comprising at least one *variola* virus homologue protein selected from the group consisting of A36R, B6R, and M1R.

12. A method of inducing an immune response in a human patient against a poxvirus infection comprising administering to said patient an effective amount of the immunogenic composition of claim 1.

13. A method of inducing an immune response in a human patient against a poxvirus infection comprising administering to said patient an effective amount of the immunogenic composition of claim 3.

14. A composition comprising two soluble truncated mammalian poxvirus envelope proteins, wherein said proteins comprise A33Rt and L1R(185t), wherein said L1R(185t) is not myristoylated.

15. The composition of claim 14, wherein said poxvirus is selected from *vaccinia* virus and *variola* virus.

16. The composition of claim 14, said composition further comprising a pharmaceutically acceptable carrier.

17. The composition of claim 14, wherein the amino acid sequence of said A33Rt is the sequence of SEQ ID NO:3 and the amino acid sequence of said L1R(185t) is the sequence of SEQ ID NO: 1.

18. A kit comprising an immunogenic amount of two soluble truncated poxvirus envelope proteins wherein said proteins comprise A33Rt and L1R(185t), wherein said L1R (185t) protein is not myristoylated, said kit further comprising an applicator and an instructional material for the use of said kit.

* * * * *

UNITED STATES PATENT AND TRADEMARK OFFICE
CERTIFICATE OF CORRECTION

PATENT NO. : 7,560,116 B2  
APPLICATION NO. : 11/010979  
DATED : July 14, 2009  
INVENTOR(S) : Gary H. Cohen et al.

It is certified that error appears in the above-identified patent and that said Letters Patent is hereby corrected as shown below:

In the Specification

Please amend Column 1, Lines 17-24 as follows:
-- STATEMENT REGARDING FEDERALLY SPONSORED RESEARCH OR DEVELOPMENT
This invention was made with government support under grant numbers AI002002, AI053404 and AI057168 awarded by the National Institutes of Health. The government has certain rights in the invention. --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*